(12) United States Patent
Loshakove et al.

(10) Patent No.: US 7,063,711 B1
(45) Date of Patent: Jun. 20, 2006

(54) VASCULAR SURGERY

(75) Inventors: Amir Loshakove, Moshav-Bazrs (IL); Ido Kilemnik, Herzelia (IL); Dvir Keren, Petach-Tikva (IL)

(73) Assignee: By-Pass, Inc., Orangeburg, NY (US)

( * ) Notice: Subject to any disclaimer, the term of this patent is extended or adjusted under 35 U.S.C. 154(b) by 0 days.

(21) Appl. No.: 09/936,806

(22) PCT Filed: Dec. 8, 1999

(86) PCT No.: PCT/IL99/00670

§ 371 (c)(1), (2), (4) Date: Sep. 17, 2001

(87) PCT Pub. No.: WO00/56226

PCT Pub. Date: Sep. 28, 2000

Related U.S. Application Data

(63) Continuation-in-part of application No. 09/701,531, filed as application No. PCT/IL99/00284 on May 30, 1999, and a continuation-in-part of application No. 09/701,523, filed as application No. PCT/IL99/00285 on May 30, 1999.

(30) Foreign Application Priority Data

| May 29, 1998 | (IL) | ................................. 124694 |
| Mar. 19, 1999 | (IL) | ................................. 129067 |

(51) Int. Cl.
*A61B 17/00* (2006.01)

(52) U.S. Cl. .................................... 606/153

(58) Field of Classification Search ........... 606/149, 606/153, 167, 216, 170, 184, 185
See application file for complete search history.

(56) References Cited

U.S. PATENT DOCUMENTS

| 1,867,624 A | 7/1932 | Hoffman |
| 2,505,358 A | 4/1950 | Gusberg et al. |
| 2,994,321 A | 8/1961 | Tischler |
| 3,104,666 A | 9/1963 | Hale et al. |
| 3,180,337 A | 4/1965 | Smialowski |
| 3,221,746 A | 12/1965 | Noble |
| 3,519,187 A | 7/1970 | Kapitanov et al. |
| 3,657,744 A | 4/1972 | Ersek |
| 3,776,237 A | 12/1973 | Hill et al. |
| 3,837,345 A | 9/1974 | Matar |
| 3,901,243 A | 8/1975 | Read |

(Continued)

FOREIGN PATENT DOCUMENTS

DE  297 13 335  11/1997

(Continued)

OTHER PUBLICATIONS

U.S. Appl. No. 60/123,482.*

(Continued)

*Primary Examiner*—Cary E. O'Connor
(74) *Attorney, Agent, or Firm*—Fenster & Company

(57) ABSTRACT

An anastomotic connector for connecting a graft to a target vessel, comprising a thin collar section (104) adapted to engage a portion of the graft; and a separate spike section (124) adapted to mount on said collar section, and comprising a plurality of spikes (126) each of said spikes (126) adapted to transfix said graft. Preferably, the connector comprises at least one locking element for interlocking said spike section (124), and said collar section (104). Preferably the locking element provides a spring action between the two sections.

107 Claims, 54 Drawing Sheets

U.S. PATENT DOCUMENTS

| | | |
|---|---|---|
| 3,908,662 A * | 9/1975 | Razgulov et al. |
| 3,973,570 A | 8/1976 | Razgulov et al. |
| 4,018,228 A | 4/1977 | Goosen |
| 4,214,586 A | 7/1980 | Mericle |
| 4,214,587 A | 7/1980 | Sakura, Jr. |
| 4,216,776 A | 8/1980 | Downie et al. |
| 4,352,358 A | 10/1982 | Angelchik |
| 4,366,819 A | 1/1983 | Kaster |
| 4,368,734 A | 1/1983 | Banko |
| 4,368,736 A | 1/1983 | Kaster |
| 4,523,592 A | 6/1985 | Daniel |
| 4,586,503 A | 5/1986 | Kirsch et al. |
| 4,657,019 A | 4/1987 | Walsh et al. |
| 4,696,300 A | 9/1987 | Anderson |
| 4,696,308 A | 9/1987 | Meller et al. |
| 4,785,809 A | 11/1988 | Weinrib |
| 4,796,627 A | 1/1989 | Tucker |
| 4,846,174 A | 7/1989 | Willard et al. |
| 4,872,874 A | 10/1989 | Taheri |
| 4,917,087 A | 4/1990 | Walsh et al. |
| 4,926,858 A | 5/1990 | Gifford, III et al. |
| 4,930,502 A | 6/1990 | Chen |
| 4,930,674 A | 6/1990 | Barak |
| 4,958,414 A | 9/1990 | Benoit |
| 4,997,439 A | 3/1991 | Chen |
| 5,009,643 A | 4/1991 | Reich et al. |
| 5,035,702 A | 7/1991 | Taheri |
| 5,037,433 A | 8/1991 | Wilk et al. |
| 5,041,082 A | 8/1991 | Shiber |
| 5,129,913 A | 7/1992 | Ruppert |
| 5,141,516 A | 8/1992 | Detweiler |
| 5,192,294 A | 3/1993 | Blake, III |
| 5,197,465 A | 3/1993 | Montgomery |
| 5,201,901 A | 4/1993 | Harada et al. |
| 5,234,447 A | 8/1993 | Kaster et al. |
| 5,234,448 A | 8/1993 | Wholey et al. |
| 5,236,437 A | 8/1993 | Wilk et al. |
| 5,250,058 A | 10/1993 | Miller et al. .......... 606/154 |
| 5,254,127 A | 10/1993 | Wholey et al. |
| 5,275,622 A | 1/1994 | Lazarus et al. |
| 5,284,485 A | 2/1994 | Kammerer et al. |
| 5,292,309 A | 3/1994 | Van Tassel et al. |
| 5,323,765 A | 6/1994 | Brown |
| 5,366,462 A | 11/1994 | Kaster et al. |
| 5,392,979 A | 2/1995 | Green et al. |
| 5,403,333 A | 4/1995 | Kaster et al. |
| 5,403,338 A | 4/1995 | Milo |
| 5,425,739 A | 6/1995 | Jessen |
| 5,441,517 A | 8/1995 | Kensey et al. |
| 5,445,623 A | 8/1995 | Richmond |
| 5,445,632 A | 8/1995 | Blake et al. |
| 5,456,712 A | 10/1995 | Maginot |
| 5,478,353 A | 12/1995 | Yoon |
| 5,484,451 A | 1/1996 | Akopov et al. |
| 5,488,958 A | 2/1996 | Topel et al. |
| D372,310 S | 7/1996 | Hartnett |
| 5,536,251 A | 7/1996 | Evard et al. |
| 5,540,715 A | 7/1996 | Katsaros et al. |
| 5,562,690 A | 10/1996 | Green et al. |
| 5,562,728 A | 10/1996 | Lazarus et al. |
| 5,575,800 A | 11/1996 | Gordon |
| 5,591,178 A | 1/1997 | Green et al. |
| 5,649,946 A | 7/1997 | Bramlet |
| 5,658,282 A | 8/1997 | Daw et al. |
| 5,676,670 A | 10/1997 | Kim |
| 5,676,696 A | 10/1997 | Marcade |
| 5,685,838 A | 11/1997 | Peters |
| 5,690,656 A | 11/1997 | Cope et al. |
| 5,690,662 A | 11/1997 | Chiu et al. |
| 5,695,504 A * | 12/1997 | Gifford, III et al. ........ 606/153 |
| 5,697,943 A * | 12/1997 | Sauer et al. ......... 606/153 |
| 5,702,412 A | 12/1997 | Popov et al. |
| 5,707,380 A | 1/1998 | Hinchliffe et al. |
| 5,709,335 A | 1/1998 | Heck |
| 5,733,308 A | 3/1998 | Daugherty et al. |
| 5,755,778 A | 5/1998 | Kleshinski |
| 5,758,663 A | 6/1998 | Wilk et al. |
| 5,797,920 A | 8/1998 | Kim |
| 5,797,934 A | 8/1998 | Rygaard ................. 606/153 |
| 5,817,111 A | 10/1998 | Riza |
| 5,817,113 A | 10/1998 | Gifford, III et al. |
| 5,823,971 A | 10/1998 | Robinson et al. |
| 5,824,002 A | 10/1998 | Gentelia et al. |
| 5,824,008 A | 10/1998 | Bolduc et al. |
| 5,827,316 A | 10/1998 | Young et al. |
| 5,830,222 A | 11/1998 | Makower |
| 5,833,698 A | 11/1998 | Hinchliffe et al. |
| 5,868,763 A | 2/1999 | Spence et al. |
| 5,893,369 A | 4/1999 | LeMole |
| 5,910,153 A | 6/1999 | Mayenberger |
| 5,910,155 A | 6/1999 | Ratcliff et al. |
| 5,922,000 A | 7/1999 | Chodorow |
| 5,931,842 A | 8/1999 | Goldsteen et al. |
| 5,951,576 A | 9/1999 | Wakabayashi |
| 5,957,938 A | 9/1999 | Zhu et al. |
| 5,957,973 A | 9/1999 | Quiachon et al. |
| 5,968,069 A | 10/1999 | Dusbabek et al. |
| 5,972,014 A | 10/1999 | Nevins |
| 5,976,159 A | 11/1999 | Bolduc et al. |
| 5,976,178 A | 11/1999 | Goldsteen |
| 5,989,278 A | 11/1999 | Mueller |
| 5,989,287 A | 11/1999 | Yang et al. |
| 5,993,468 A | 11/1999 | Rygaard |
| 6,004,330 A | 12/1999 | Middleman et al. |
| 6,004,341 A | 12/1999 | Zhu et al. |
| 6,022,351 A | 2/2000 | Bremer et al. ............... 606/72 |
| 6,022,367 A | 2/2000 | Sherts |
| 6,024,763 A | 2/2000 | Lenker et al. |
| 6,026,814 A | 2/2000 | LaFontaine et al. |
| 6,035,856 A | 3/2000 | LaFontaine et al. |
| 6,036,702 A | 3/2000 | Bachinski et al. |
| 6,071,292 A | 6/2000 | Makower et al. |
| 6,080,176 A | 6/2000 | Young |
| 6,113,612 A | 9/2000 | Swanson et al. |
| 6,152,937 A | 11/2000 | Peterson et al. |
| 6,165,185 A | 12/2000 | Shennib et al. |
| 6,171,319 B1 | 1/2001 | Nobles et al. |
| 6,176,867 B1 | 1/2001 | Wright |
| 6,179,848 B1 * | 1/2001 | Solem ................. 606/153 |
| 6,185,792 B1 | 2/2001 | Nelson et al. |
| 6,186,942 B1 | 2/2001 | Sullivan et al. |
| 6,190,353 B1 | 2/2001 | Makower et al. |
| 6,193,734 B1 | 2/2001 | Bolduc et al. |
| 6,206,912 B1 | 3/2001 | Goldsteen et al. |
| 6,248,117 B1 | 6/2001 | Blatter .................. 606/153 |
| 6,251,116 B1 | 6/2001 | Shennib et al. |
| 6,261,315 B1 | 7/2001 | St. Germain et al. |
| 6,302,905 B1 | 10/2001 | Goldsteen et al. |
| 6,309,416 B1 | 10/2001 | Swanson et al. |
| 6,387,108 B1 | 5/2002 | Taylor et al. |
| 6,391,036 B1 | 5/2002 | Berg et al. |
| 6,391,038 B1 | 5/2002 | Vargas et al. |
| 6,398,797 B1 | 6/2002 | Bombard et al. |
| 6,402,764 B1 | 6/2002 | Hendricksen et al. |
| 6,419,681 B1 | 7/2002 | Vargas et al. |
| 6,428,550 B1 | 8/2002 | Vargas et al. |
| 6,461,320 B1 | 10/2002 | Yencho et al. |
| 6,478,804 B1 | 11/2002 | Vargas et al. |
| 6,485,496 B1 | 11/2002 | Suyker et al. |
| 6,497,710 B1 | 12/2002 | Yencho et al. |
| 6,508,252 B1 | 1/2003 | Berg et al. |
| 6,511,491 B1 * | 1/2003 | Grudem et al. ............ 606/153 |
| 6,514,196 B1 | 2/2003 | Sullivan et al. |
| 6,514,265 B1 | 2/2003 | Ho et al. |

| | | |
|---|---|---|
| 6,517,558 B1 | 2/2003 | Gittings et al. |
| 6,533,812 B1 | 3/2003 | Swanson et al. |
| 6,537,287 B1 | 3/2003 | Yencho et al. |
| 6,537,288 B1 | 3/2003 | Vargas et al. |
| 6,588,643 B1 | 7/2003 | Bolduc et al. |
| 6,632,241 B1 | 10/2003 | Hancock |
| 6,652,541 B1 | 11/2003 | Vargas et al. |
| 2001/0004698 A1 | 6/2001 | Blatter et al. ............... 606/153 |
| 2001/0004699 A1 | 6/2001 | Gittings et al. |
| 2001/0016752 A1 | 8/2001 | Berg et al. |
| 2001/0025643 A1 | 10/2001 | Foley |
| 2001/0047180 A1 | 11/2001 | Grudem et al. |
| 2002/0004663 A1 | 1/2002 | Gittings et al. |
| 2002/0019642 A1 | 2/2002 | Milliman et al. |
| 2002/0022852 A1 | 2/2002 | Dakov |
| 2002/0022857 A1 | 2/2002 | Goldsteen et al. |
| 2002/0082614 A1 | 6/2002 | Logan et al. |
| 2002/0087046 A1 | 7/2002 | Sullivan et al. |
| 2002/0087181 A1 | 7/2002 | Goldsteen et al. |
| 2002/0091398 A1 | 7/2002 | Galdonik et al. |
| 2002/0099394 A1 | 7/2002 | Houser et al. |
| 2002/0108621 A1 | 8/2002 | Berg et al. |
| 2002/0169470 A1 | 11/2002 | Kuhr et al. |
| 2003/0083541 A1 | 5/2003 | Sullivan et al. |
| 2003/0083679 A1 | 5/2003 | Grudem et al. |
| 2003/0093118 A1 | 5/2003 | Ho et al. |

FOREIGN PATENT DOCUMENTS

| | | |
|---|---|---|
| EP | 0 539 237 | 4/1993 |
| EP | 0 916 314 | 5/1999 |
| EP | 1 055 401 | 11/2000 |
| GB | 2 094 212 | 9/1982 |
| IT | 1215699 | 2/1990 |
| WO | WO 89/06515 | 7/1989 |
| WO | WO 89/08433 | 9/1989 |
| WO | WO 95/26170 | 10/1995 |
| WO | WO 96/25886 | 8/1996 |
| WO | WO 96/33673 | 10/1996 |
| WO | WO 97/13463 | 4/1997 |
| WO | WO 97/13471 | 4/1997 |
| WO | WO 97/27898 | 8/1997 |
| WO | WO 97/28749 | 8/1997 |
| WO | WO 97/40754 | 11/1997 |
| WO | WO 98/07399 | 2/1998 |
| WO | WO 98/16161 | 4/1998 |
| WO | WO 98/19629 | 5/1998 |
| WO | WO 98/19634 | 5/1998 |
| WO | WO 98/19635 | 5/1998 |
| WO | WO 98/19636 | 5/1998 |
| WO | WO 98/30152 | 7/1998 |
| WO | WO 98/32412 | 7/1998 |
| WO | WO 98/38922 | 9/1998 |
| WO | WO 98/38939 | 9/1998 |
| WO | WO 98/38941 | 9/1998 |
| WO | WO 98/38942 | 9/1998 |
| WO | WO 98/55027 | 12/1998 |
| WO | WO 98/57591 | 12/1998 |
| WO | WO 98/57592 | 12/1998 |
| WO | WO 99/21491 | 5/1999 |
| WO | WO 99/37218 | 7/1999 |
| WO | WO 99/38441 | 8/1999 |
| WO | WO 99/40851 | 8/1999 |
| WO | WO 99/40868 | 8/1999 |
| WO | WO 99/65409 | 12/1999 |
| WO | WO 00/21436 | 4/2000 |
| WO | WO 00/27311 | 5/2000 |
| WO | WO 00/27312 | 5/2000 |
| WO | WO 00/27313 | 5/2000 |
| WO | WO 00/45886 | 8/2000 |
| WO | WO 00/53104 | 9/2000 |
| WO | WO 00/06349 | 11/2000 |
| WO | WO 00/66007 | 11/2000 |
| WO | WO 00/66009 | 11/2000 |
| WO | WO 00/69343 | 11/2000 |
| WO | WO 00/69346 | 11/2000 |
| WO | WO 00/69364 | 11/2000 |
| WO | WO 00/72764 | 12/2000 |
| WO | WO 00/74579 | 12/2000 |
| WO | WO 01/08566 | 2/2001 |
| WO | WO 01/15607 | 3/2001 |
| WO | WO 01/15609 | 3/2001 |
| WO | WO 01/17440 | 3/2001 |
| WO | WO 01/17441 | 3/2001 |
| WO | WO 01/19259 | 3/2001 |
| WO | WO 01/26562 | 4/2001 |
| WO | WO 01/30444 | 5/2001 |

OTHER PUBLICATIONS

Certified Copy of U.S. Appl. No. 09/324,997, published on Sep 14, 2000, Grudem, J. et al., "Medical Grafting Methods and Apparatus".

Certified Copy of U.S. Appl. No. 60/137,764, published on Dec. 14, 2000, Logan, J. et al., "Mechanical Anastomosis Delivery Apparatus".

Certified Copy of U.S. Appl. No. 09/187,361, published on May 18, 2000, Galdonik, J. A. et al., "Medical Graft Component and Methods of Installing Same".

Certified Copy of U.S. Appl. No. 09/187,364, published on May 18, 2000, Berg, T. A. et al., "Minimally Invasive Revascularization Apparatus and Methods".

Draney, M. et al.; "Coronary Artery Bypass Surgery: Minimally Invasive Techniques"; May 1998; Retrieved from Internet: <http://me210abc.stanford.edu/94-95/projects/Pfizer/Spring/1.html.

Obora, Y. et al,; "Nonsuture Microvascular Anastomosis Using Magnet Rings: Preliminary Report"; Feb. 1978; pp. 117-120; Sur Neurol (U.S.); vol. 9, No. 2.

Östrup, L. T. et al.; "The UNILINK Instrument System for Fast and Safe Microvascular Anastomosis"; pp.521-526; Department of Plastic Surgery, Hand Surgery, and Burns; University Hospital, Sweden; presented in part at the First Scandinavian Seminar on Reconstructive Microsurgery, Sweden, Oct. 1979, and at the Symposium on Microneurovascular Surgery, Denmark, Jan. 1983.

Yachia, D. et al.; "Bio-Fragmentable Anastomosis Ring in Urological Surgery Involving the Gastrointestinal Tract; Early Experiences ans a Historical Review of Mechanical Intestinal Anastomosis"; May 1995 pp. 1426-1428; The Journal of Urology; vol. 153.

US 6,503,260, 01/2003, Schaller et al. (withdrawn)

* cited by examiner

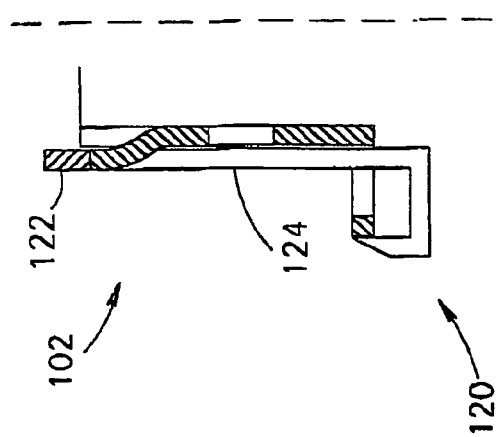
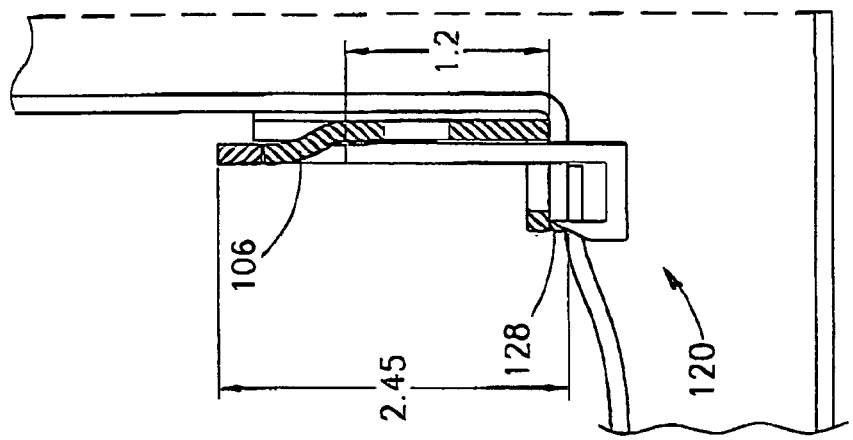
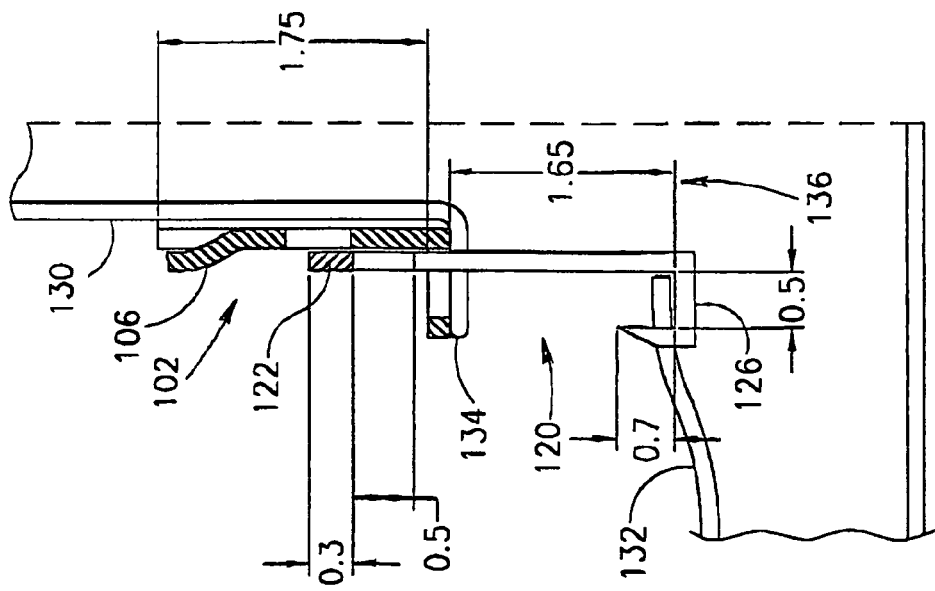
FIG.2E
FIG.2D
FIG.2C

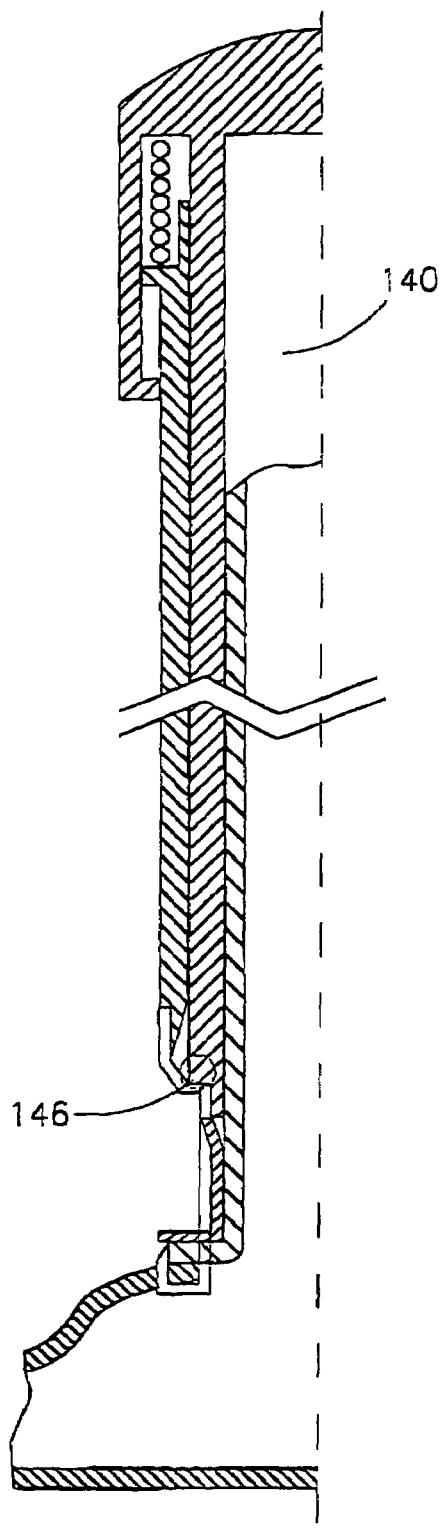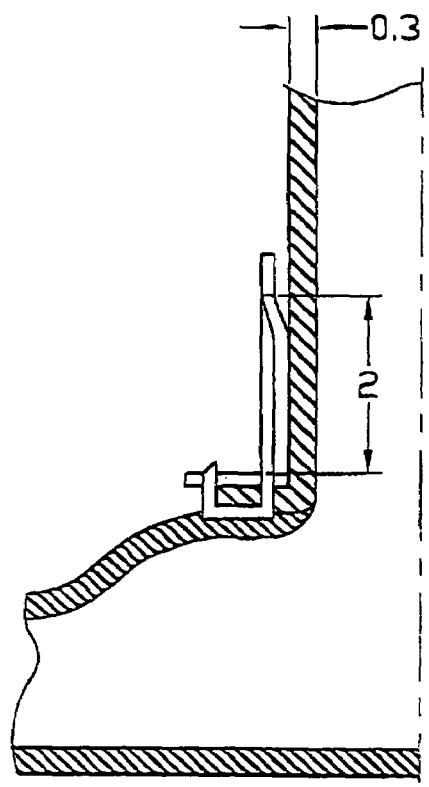
FIG.4C
FIG.4D

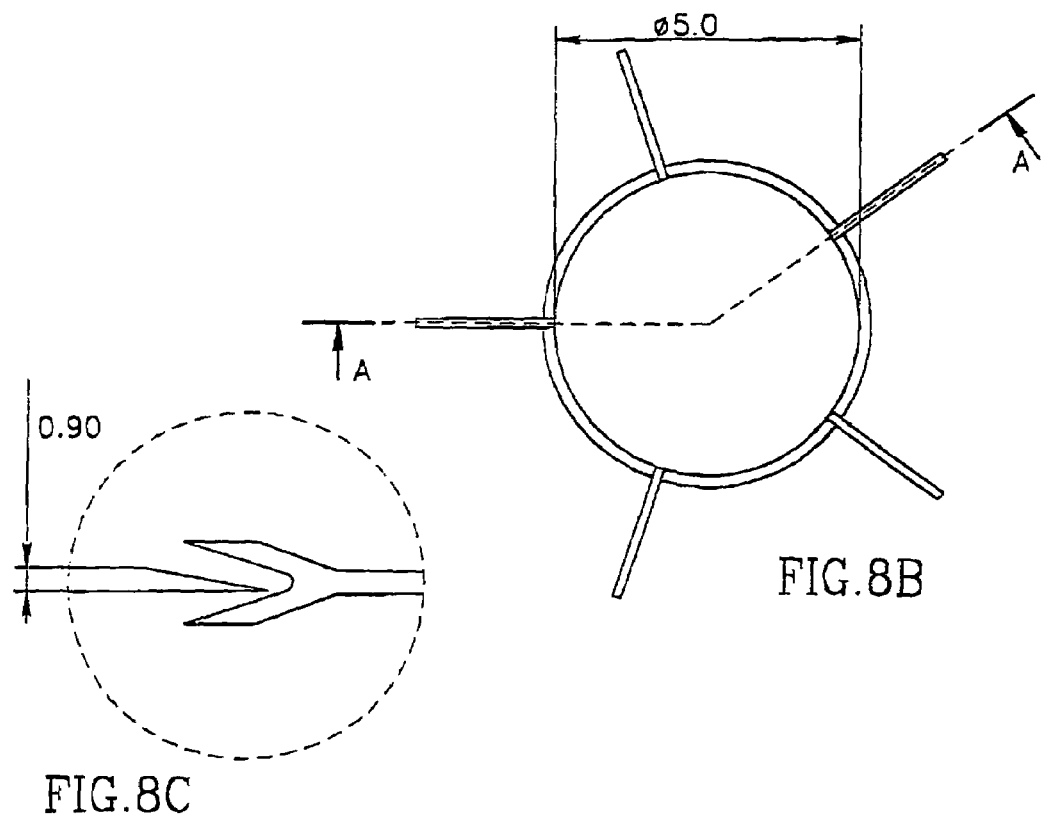
FIG.8B
FIG.8C
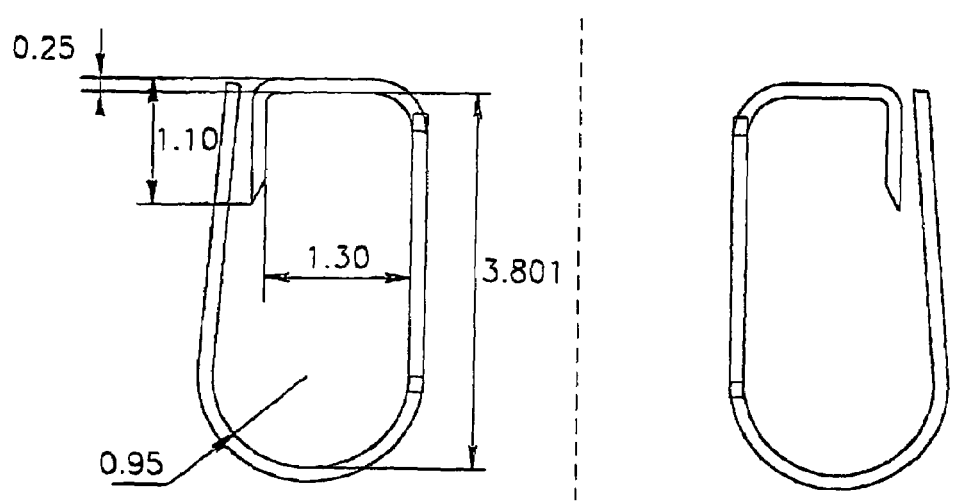
FIG.8D

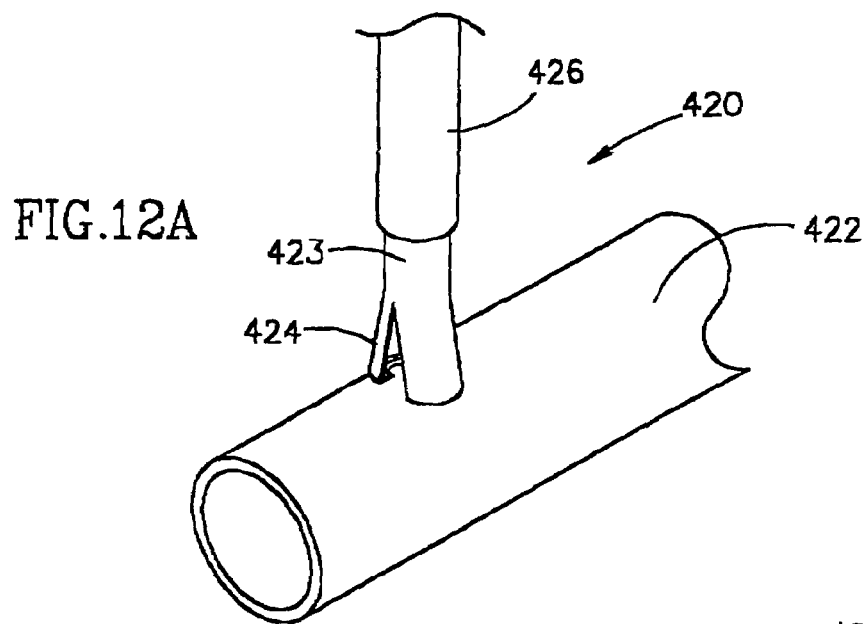
FIG.12A
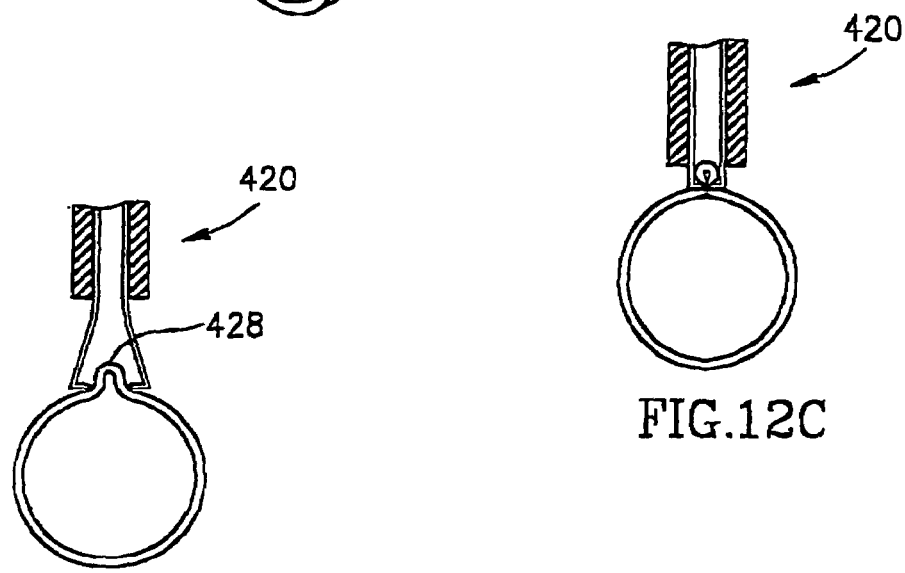
FIG.12B
FIG.12C
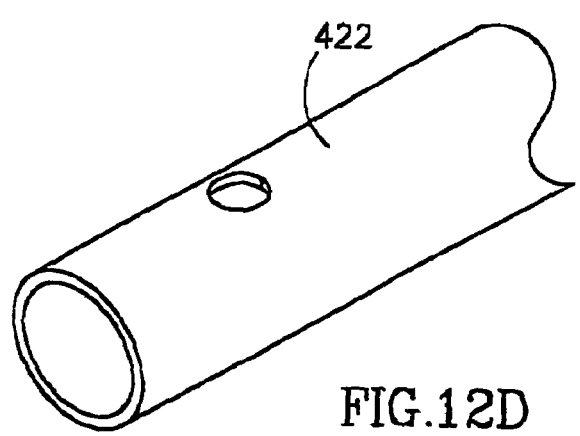
FIG.12D

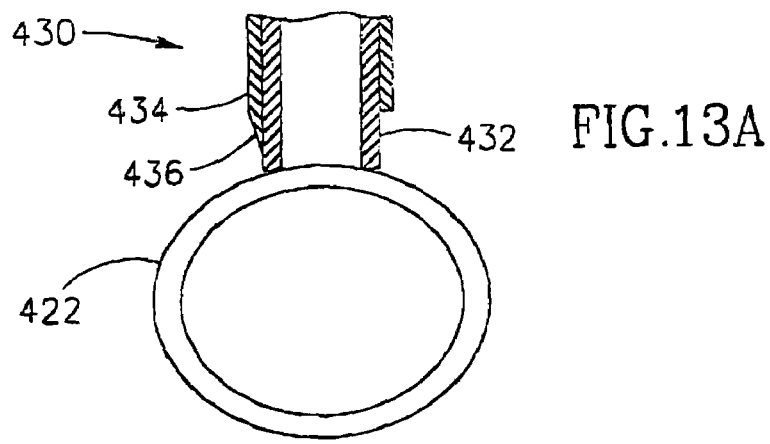
FIG.13A
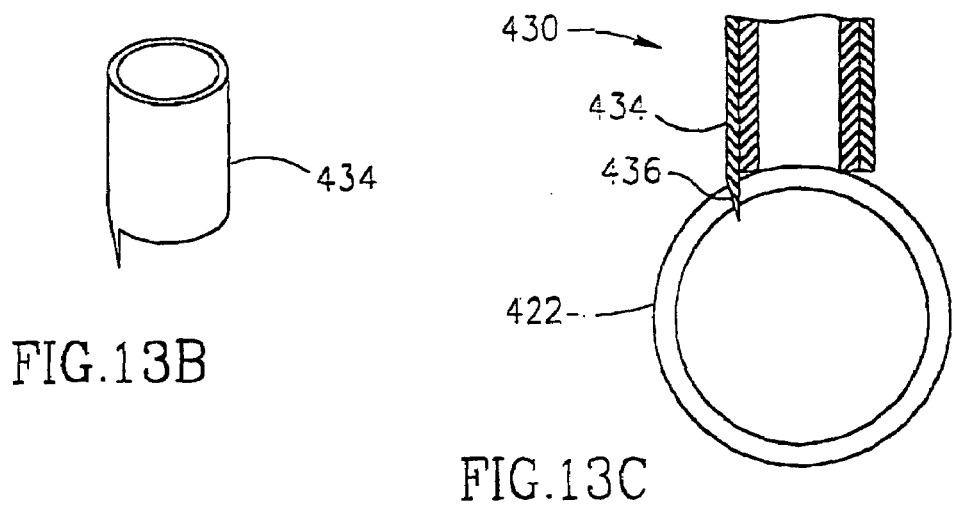
FIG.13B
FIG.13C
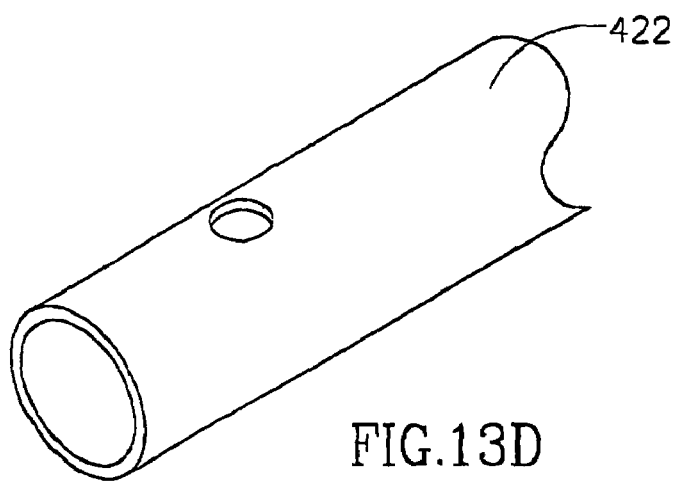
FIG.13D

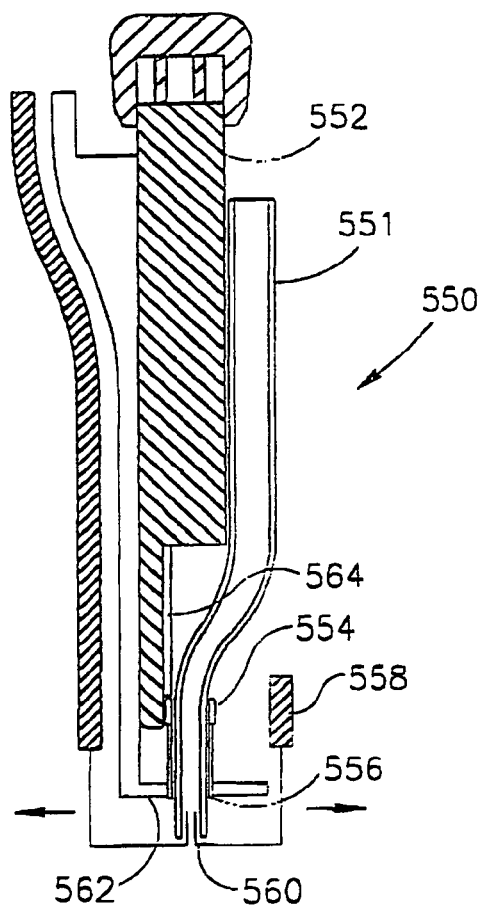
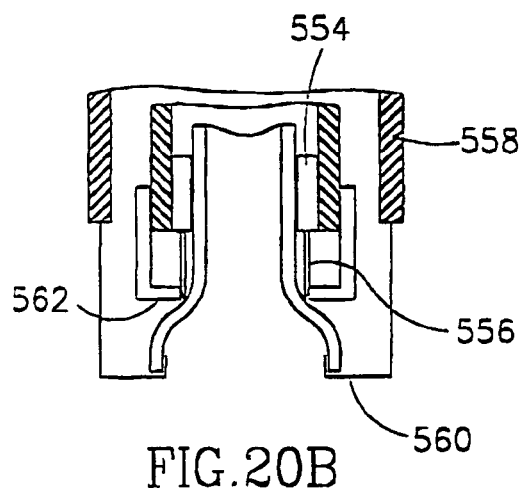
FIG.20A
FIG.20B
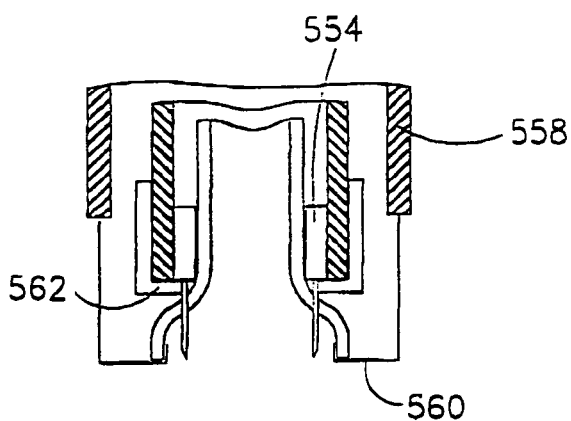
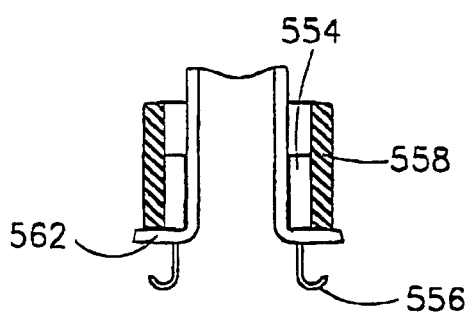
FIG.20C
FIG.20D

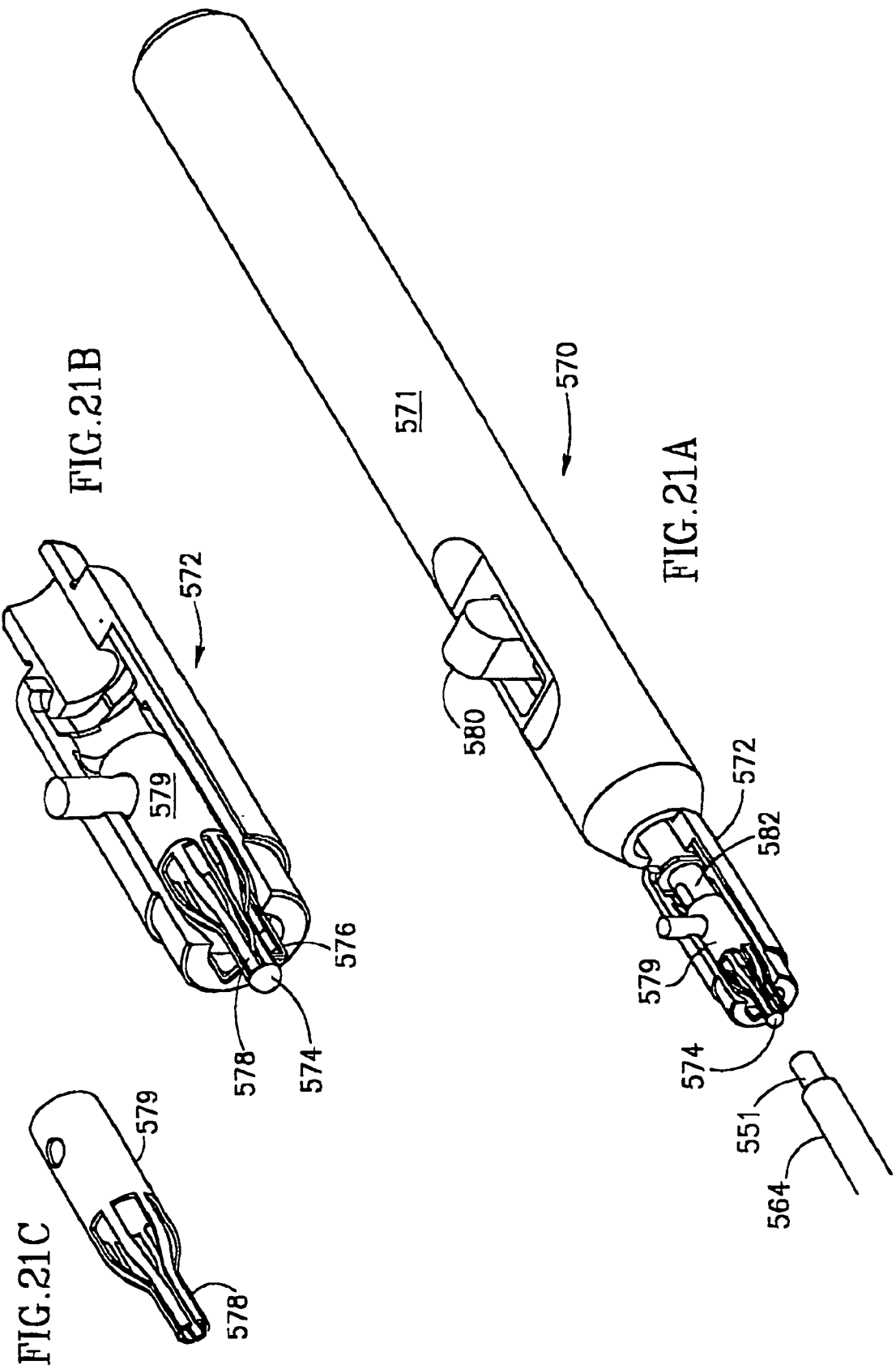

VASCULAR SURGERY

RELATED APPLICATIONS

This application is a national phase filing of PCT/IL99/00670, filed Dec. 8, 1999. This application is a continuation-in-part of PCT application PCT/IL99/00284, filed May 30, 1999, now U.S. application Ser. No. 09/701,531, filed Nov. 28, 2000, and of PCT application PCT/IL99/00285 filed May 30, 1999, now U.S. application Ser. No. 09/701,523, filed Nov. 28, 2000, the disclosures of which are incorporated herein by reference.

FIELD OF THE INVENTION

The present invention relates to performing anastomosis of blood vessels.

BACKGROUND OF THE INVENTION

Connecting two blood vessels, anastomosis, is an important surgical technique for reconstructive, therapeutic and cosmetic surgery. The gold standard of anastomosis is manual suturing of the two blood vessels in a side to side, end to end or end-to-side configuration. Although it is generally desirable to shorten the length of any surgical procedure, this is especially important in coronary bypass surgery, in which a patient is usually attached to a heart-lung machine and his heart is often stopped.

In addition to manual suturing of blood vessels, other methods of attaching two blood vessels are known, including, staples and anastomosis rings. PCT publications WO 97/40754 and WO 97/28749, the disclosures of which are incorporated herein by reference, describe staplers for coronary bypass surgery, wherein a graft is connected on one of its ends to the aorta and at its other end to an occluded coronary artery, distal to the occlusion. In this type of surgery, the anastomosis is sealed by stapling the graft to the aorta, while pressing both aorta and graft against an anvil. In one publication, the anvil is inserted into the aorta for the stapling and then removed, possibly by taking the anvil apart. In the other publication, the end of the graft is everted over a ring-shaped anvil, so that the anvil is outside of the blood vessel at all times.

Recently, bypass surgery has been performed using minimally invasive (key-hole) surgery. In this type of surgery, a small hole is made in the chest, instead of cracking open the ribs, and the mammary arteries (e.g., LIMA, RIMA) are used for bypass grafts. The suturing and/or stapling is performed using tools, for example as described above.

An even less invasive type of surgery requires no opening of the chest at all, rather, one or more catheters are introduced into the blood vessels using a precutaneous approach. PCT publications WO 97/27898, WO 97/13471 and WO 97/13463 and their priority documents, namely U.S. application 60/010,614, 60/005,164, 08/730,327 and 08/730,496, the disclosures of which are incorporated herein by reference and termed the "Transvascular Applications", describe method and apparatus for precutaneous treatment of arterial occlusions. Two main methods are taught in these applications. In one method, a tunnel is excavated within tissue (outside the vessel) from one side of the occlusion to the other side of the occlusion, and a stent or a stent/graft may be placed within the tunnel. In another method, a conveniently located vein or graft is attached to the occluded vessel and two side-to-side anastomosis are created between the occluded vessel and the vein or graft bypassing the occlusion. The distal and proximal portions of the vein are closed in one of a variety of manners. The connection between the vein and the artery may be by welding the two blood vessels, or by using one of a variety of connectors that are suggested. One of the disclosed connectors comprises two springs separated by a short segment of a possibly unstented graft. The springs have the form of an inverted funnel, so that the two blood vessels are urged together. Where there is a spacing between the blood vessels, various techniques and/or devices are suggested for stopping the surrounding tissue from compressing the connection between the vein and the artery. One of the purposes of the various types of connectors is to maintain the two blood vessels near each-other, either in contact or by compressing tissue between them, presumably so no blood will leak from the connection between the connector and the blood vessels.

In a TIPS procedure, a stent is placed into a passage precutaneously forced, opened or excavated between a portal vein and a hepatic vein. As in some of the embodiments described in the previous paragraph, the relative location of the blood vessels is maintained by the existence of relatively solid tissue surrounding and between the two blood vessels. Thus, there is no requirement that each of the connections between an end of the connector and the respective blood vessel to which it is attached, be, of itself, completely leak-proof.

In WWW publication "http://me210abc.stanford.edu/94–95/projects/Pfizer/Spring/1.html", available March 1998, the disclosure of which is incorporated herein by reference, a method is described for reducing the complexity of performing a bypass surgery. In this method, a graft is precutaneously brought to the aorta and pushed out of an incision in the aorta near a site of a bypass surgery. A keyhole opening is made in the chest to bring a tool to suture or staple the graft to the aorta and to the coronary which is to be bypassed.

The attachment of a graft to a coronary vessel is especially problematic, inasmuch as the vessel is typically diseased and, being thin, it is easily damaged.

Many people suffer from blockages of the peripheral blood vessels. A typical treatment procedure in these cases is to perform a bypass of the abdominal aorta, of the femoral artery or perform a femoral-popliteal bypass.

SUMMARY OF THE INVENTION

An aspect of some preferred embodiments of the invention relates to a self-locking anastomosis device comprising a collar portion and a spike portion comprising a plurality of interconnected spikes, both of which portions are preferably formed of a sheet material or a tube material, preferably the same material. In a preferred embodiment of the invention, the spike portion locks against the collar portion so that once the anastomosis device is deployed, it does not open by itself. In a preferred embodiment of the invention, the anastomosis device is formed of two components, a spike section and a collar section. Alternatively, the two sections may be integrated in a single component. In a preferred embodiment of the invention, the lock includes some flexibility, to example to allow relative axial motion of the two sections.

An aspect of some preferred embodiments of the invention relates to an anastomotic connector having a spring element for allowing relative motion between a two vessels connected by the anastomotic connector. In a preferred embodiment of the invention, a plurality of spring elements are provided so that different parts of the vessels have a different amount of relative motion. In a preferred embodiment of the invention, all the springs are referenced to a single collar attached to one of the vessels. However, this is not essential and different springs can be referenced to different ones of the vessels and/or to different portions of the connector. In a preferred embodiment of the invention, the springs allow relative motion between spikes which engage one vessel and the collar which is coupled to a second vessel. Alternatively or additionally to allowing relative motion of significant portions of the vessels, the relative motion may be limited to small parts of the anastomosis connection. In one example, by providing each spike with a spring, differences in the thickness of tissue engaged by the spike are compensated for by the spring. Alternatively or additionally, the spring allow the areas of contact between the vessels to be urged against each other. The spring element may be an explicit spring element, for example formed as part of a spike. Alternatively, the spring may be functionally included in another structure, for example a locking element for interlocking the two parts of a two part anastomotic device.

An aspect of some preferred embodiments of the invention relates to forming holes in small vessels, such as coronary vessels. In a preferred embodiment of the invention, a small hole is formed by first grabbing a small section of a vessel (e.g., a coronary) and then cutting the grabbed section. The grabbing and cutting may be by separate elements of a hole puncher or by a single element. In a preferred embodiment of the invention, the grabbed section has a radius smaller than twice the thickness of the coronary. Alternatively or additionally, after the coronary is grabbed, the grabbing element is retracted from the vessel, so that the grabbed section of the coronary is distanced from the opposite side of the coronary.

An aspect of some embodiments of the invention relates to forming holes in a coronary vessel by cutting along a circumference of a desired hole. In a preferred embodiment of the invention, a rotating cutting device is provided having a central grabber and a cutting edge, preferably in the form of a spike, on its circumference. In a preferred embodiment of the invention, the grabber is a hollow tube for providing vacuum. Alternatively or additionally, the grabber is a mechanical grasper. In use, the grabber grabs the vessel, so that the spike penetrates the vessel wall. The spike-carrying portion is then rotated, so that a section of the vessel wall is cut off.

An aspect of some preferred embodiments of the invention relates to a self-retracting tip for a punch. In a preferred embodiment of the invention, the tip retracts prior to the hold being punched in the blood vessel. Preferably, the punching action is caused by the tip retracting. Optionally, once the tip retracts it cannot easily advance, thereby providing an additional safety feature.

An aspect of some preferred embodiments of the invention, relates to a hole puncher for punching oblique holes in a blood vessel. In a preferred embodiment of the invention, the hole punch comprises two elliptical surfaces, which surfaces are not parallel to each other. Preferably, a small angle, such as 5° is defined between the surfaces. Optionally, at least one of the surfaces is not planar, for example including a protrusion to better engage the blood vessel being punched through.

An aspect of some preferred embodiments of the invention relates to a hole puncher, in which the punching action is achieved by non-axial manipulation of the puncher. Thus, there is less danger of inadvertent advancement of a sharp tip of the punch and causing damage to other parts of the blood vessel or underlying tissue. Preferably, the hole puncher is adapted for key-hole surgery. Alternatively or additionally, the puncher has an axial handle. Alternatively, the puncher has a revolver grip. In a preferred embodiment of the invention, the punching is achieved by squeezing on the handle of the hole-puncher.

An aspect of some preferred embodiments of the invention relates to a set of tools for anastomosis connection, in which the tool surrounds the graft. Once the graft is attached, the tool can be removed from the graft. In some embodiments of the invention, there is a slit in the side of the tool, through which the graft is inserted and/or removed. Alternatively or additionally, the tool can open or be taken apart. Preferably, the tool includes a peg, which, when a portion of the tool is pulled over the peg, splits the tool portion apart. Preferably the tool is pre-split or at least perforated, however this is not essential. Alternatively or additionally to a peg, a knife is provided, which knife rips the tool portion axially. Preferably, the knife and/or peg are stationary and the tool portions moves relative thereto. Alternatively or additionally, the knife or peg are moved. Optionally, the tool includes a rigid portion which prevents the separation of the pre-spilt tool. However, this rigid portion includes an opening, which, once the pre-split tool is retracted to the opening, allow the tool to spilt, so that the graft can be removed from the enclosing tool. Exemplary tools in such a kit are one or more of an anastomosis maker, an graft everter and an anastomosis mounter. These tools may comprise a single tool with different attachments. Alternatively or additionally, the tools are adapted for a keyhole approach. Alternatively or additionally, the tools are adapted for a transvascular or an endoscopic approach.

Alternatively or additionally, the tool is cut open using an external tool, such as a knife. Alternatively or additionally, a rip cord is used to slit open the tool.

An aspect of some preferred embodiments of the invention relates to a method of engaging an anastomosis connector during deployment. In a preferred embodiment of the invention, the connector includes at least one (transaxial) thickening, preferably on a spike. This thickening is preferably used to pull the connector away from the blood vessel, thereby piercing the blood vessel using hooked spikes on the other side of the connector. Alternatively or additionally, the thickening is used to push the connector forwards, into the blood vessel. In a preferred embodiment of the invention, the spike on which the thickening is formed is elastic, super elastic or otherwise moves out of the connector plane when the anastomosis device is employed. Thus, the anastomosis device is disconnected from a deployment tool by allowing or causing the spikes to bend out of an axial engagement by the tool.

An aspect of some preferred embodiments of the invention relates to a method of mounting a spike-including anastomosis device on a graft, without a separate step of everting the graft. In a preferred embodiment of the invention, the graft is transfixed on the spikes in a first configuration of the spikes, while maintaining the graft in a substantially neutral configuration (e.g., uneverted). After the graft is transfixed, the spike configuration is changed, for example rotated outwards, so that the spikes are in a better position to engage a second vessel when the anastomosis is performed. When the graft is advanced towards the second vessel, the graft is preferably everted by the contact. In a preferred embodiment of the invention, the spikes are hooked so as to easily penetrate the graft when they are pointed at the graft and to easily engage the second vessel when they are rotated away from the graft.

An aspect of some preferred embodiments of the invention relates to a method of everting a graft, in which the graft end is rolled up back over the portion of graft adjacent to the graft end. In a preferred embodiment of the invention, the end of the graft is grasped and then pulled back over the graft. Preferably, the graft is enclosed in a tube over which the end is everted. Preferably, free motion between the tube and the graft are allowed. However, the end of the tube serves as a pivot for folding back of the graft. Preferably, the eversion process is mechanical and not directly manual.

An aspect of some preferred embodiments of the invention relates to a method of everting an end of a graft, in which the near end is rolled forward, over the graft, towards the distal end of the graft. In a preferred embodiment of the invention, the graft is mounted on a tube or inside of it and the near end of the graft is pushed, preferably in small increments, towards the distal end of the graft. Preferably, rather than grasping the near end of the graft, the near end is engaged and pushed.

An aspect of some preferred embodiments of the invention relates to a method of shaping a portion of a graft, especially an end, but possibly also a middle of a graft. Preferably, this method is used for simulating the eversion of a graft without everting the graft, by causing an end of the graft to thicken. In a preferred embodiment of the invention, the graft is a mammary artery. In a preferred embodiment of the invention, the graft is thickened at its end by axially compressing the graft end. Preferably, the axial compression utilizes a form inside the graft, to set (increase, decrease or maintain) the graft inner diameter. The compression may be used to form an end that is perpendicular to the axis or the compression may be constrained to form other shapes, such as a saddle shape to match a profile of a coronary, or to form an oblique end. In a preferred embodiment of the invention, the transfixing of the graft thickening by the anastomosis connector assists in maintaining its shape. Alternatively or additionally, the thickening causes some of the intima to be presented along the end if the graft, assisting in performing an intima-to-intima anastomosis connection and/or an adventizia to adventizia connection and/or matching up of other vascular layers. In a preferred embodiment of the invention, the thickened portion is transfixed by spikes of an anastomosis connector along paths parallel to the graft axis.

An aspect of some preferred embodiments of the invention relates to creating an everted graft end having an oblique angle to the graft axis. Direct eversion at an oblique angle may be difficult. In a preferred embodiment of the invention, an anastomotic connector has spikes that are pre-bent so that their tips are at an angle substantially parallel to the surface of the other vessel. Thus, when the graft is partially everted and the spikes are extended out, the tips can easily pierce the side of the graft and assist in completing the eversion.

An aspect of some preferred embodiments of the invention relates to a form of a spike-tip useful in preventing the spike from advancing too deeply. In a preferred embodiment of the invention, the spike tip is split, for example into two or three tines (e.g., like a tuning fork). In a preferred embodiment of the invention, when a graft is pierced by the spike, the spike advances only until the spilt location meets the aorta. Optionally, the spilt defines a wide angle between the tines, to prevent compression of tissue between the tines.

An aspect of some preferred embodiments of the invention relates to a kit for performing bypass procedures in a peripheral (non-coronary) vessel, for example in the leg or the abdominal aorta. In a preferred embodiment of the invention, such a kit includes a graft having an anastomotic connector mounted at each end thereof and a guide for guiding the graft between two anastomosis connection locations. In a preferred embodiment of the invention, the guide comprises a guide wire. Alternatively, the guide is a rigid guide. Alternatively, the guide is a deflectable guide.

An aspect of some preferred embodiments of the invention relates to a method of releasing an elastic or super-elastic device from a constraint, in which removing an upper constraints allows the device to deform and detach itself from protrusions defined on the lower constraint.

An aspect of some preferred embodiments of the invention relates to a self everting anastomosis connector. In a preferred embodiment of the invention, the connector is pre-stressed and forward spikes thereof are inserted into a graft. When the spikes are released, they rotate in a plane perpendicular to the vessel axis, everting the vessel. Alternatively to engaging the vessel by transfixing it with the forward spikes, the connector may include additional crimping elements (e.g., as part of a flange), which crimp the end of the vessel between them and when they are deformed, pull the end of the vessel along, for example to form an eversion. Necrosis at the end of the vessel may be considered insignificant in some embodiments of the invention.

There is thus provided in accordance with a preferred embodiment of the invention, an anastomotic connector for connecting a graft to a target vessel, comprising:

a thin collar section, adapted to engage a portion of the graft; and a separate spike section, adapted to mount on said collar section and comprising a plurality of spikes, each of said spikes adapted to transfix said graft. Preferably, the connector comprises at least one locking element for interlocking said spike section and said collar section. Preferably, said locking element is formed on said collar portion. Preferably, said locking element mates with an aperture defined by said spike section.

In a preferred embodiment of the invention, said locking element provides a spring-action, which action resists relative motion axial between at least part of said spike section and at least part of said collar section, with a force dependent on the range of motion.

In a preferred embodiment of the invention, said spike section comprises a super-elastic material. Alternatively or additionally, said spikes are pre-bent in a hook shape, such that said hook shape is adapted to engage the target vessel. Alternatively or additionally, said collar element comprises a plurality of flange elements proximal to said target vessel. Preferably, said flange elements define apertures for said spike elements to pass through. Alternatively, said flange elements include at least one opening in their perimeter, wide enough for one of said spikes to be brought in through.

In a preferred embodiment of the invention, said collar section defines a cylindrical volume. Alternatively or additionally, said collar section is adapted to form a perpendicular anastomosis. Alternatively, said collar section is adapted to form an oblique anastomosis.

There is also provided in accordance with a preferred embodiment of the invention, an anastomotic connector for connecting a graft to a target vessel, comprising:

a base for engaging said graft;

a plurality of spikes for transfixing said graft and engaging said target vessel; and at least one spring element attached to at least one of said spikes, which spring element couples a connection between said spike and said base. Preferably, said spikes and said base form a single element. Alternatively, said spikes and said base form two separate elements.

In a preferred embodiment of the invention, said spring comprises a flat coil spring. Alternatively or additionally, said spring comprises a leaf spring. Alternatively or additionally, said at least one spring comprises at least two springs in series.

In a preferred embodiment of the invention, each of said spikes has at least one independent associated spring. Alternatively or additionally, said connector is configured for performing an oblique anastomosis. Alternatively or additionally, said connector comprises at least one tab associated with one spike of said spikes, for moving said spike. Preferably, said tab is adapted for retracting said spike. Alternatively or additionally, said tab is adapted for advancing said spike.

There is also provided in accordance with a preferred embodiment of the invention, apparatus for delivering a graft to an anastomosis, comprising:

at least two tube-like elements, each defining an aperture adapted for inserting said graft such that the graft exits through a first end of said tube-like elements;

at least one separator element mounted on at least one of said tube-like elements for splitting the other of said tube like elements, so the graft can be removed through a resulting slot, which slot spans said first end and said aperture. Preferably, said at least one separator comprises a knife which cuts said slit. Alternatively or additionally, said at least one separator comprises a spreader which widens an existing slit in said tube to form said slot.

In a preferred embodiment of the invention, the apparatus comprises an outer tube which prevents said tube from splitting unless it is sufficiently retracted. Alternatively or additionally, said tube-like elements are adapted to carry an anastomotic device between them.

There is also provided in accordance with a preferred embodiment of the invention, a method of removing a graft delivery tool from an enclosed graft, comprising:

splitting apart said tube, to form a slot using a slot-forming element; and removing said graft through said slot. Preferably, said slot-forming element comprises a knife that splits said tube. Alternatively or additionally, said slot-forming element comprises a spreader that widens an existing slit in said tube.

In a preferred embodiment of the invention, the method comprises retracting at least one tube that encloses said graft. Preferably, said retracting urges said tube against a slot forming element.

In a preferred embodiment of the invention, the method comprises moving said slot-forming element relative to said tube, to form said slot.

There is also provided in accordance with a preferred embodiment of the invention, an anastomosis connector comprising:

a ring shaped base having an axis;

at least one plurality of spikes on one side of said ring; and at least one transaxial thickening in at least one of said spikes, distanced from said ring. Preferably, the connector comprises a second plurality of spikes pointing in an opposite direction from said first set of spikes. Alternatively or additionally, said thickening comprises a point where said spike splits into tines. Preferably, said tines are shorter than a thickness of a target blood vessel for which the connector is designed.

In a preferred embodiment of the invention, said at least one plurality of spikes do not apply radial pressure towards or away from said ring, once deployed.

There is also provided in accordance with a preferred embodiment of the invention, a method of containing and releasing an anastomotic connector having a thickening, comprising:

containing said connector between two tubes, said thickening being constrained from axial motion by at least one protrusion defined on at least one of said tubes; and removing at an outer one of said tubes, such that the connector deforms and the thickening is not constrained by said at least one protrusion.

There is also provided in accordance with a preferred embodiment of the invention, a method of performing an anastomosis between a graft and a target vessel, comprising:

inserting an anastomosis connector into the target vessel;

releasing at least one forward spike of said connector;

retracting said connector such that said forward spike engages said target vessel; and completing said anastomosis. Preferably, completing said anastomosis comprises releasing at least one backward spike of said connector to engage said target vessel. Alternatively, completing said anastomosis comprises locking said spike to a part of said connector other than said spike. Alternatively, completing said anastomosis comprises releasing said spike to retract towards to a part of said connector other than said spike.

There is also provided in accordance with a preferred embodiment of the invention, a punch mechanism for punching a hole in a blood vessel, comprising:

a sharp tip adapted for puncturing said blood vessel;

a shaft having said tip at one end thereof;

a first widening element distal to said tip; and a second widening element distal to said first widening element, said first and second widening elements defining a narrowing between them, which narrowing is adapted to contain a punctured blood vessel wall; and a coupling element for coupling retraction of said tip with a relative motion of said widening elements, which relative motion is used to contract said narrowing. Preferably, said tip retracts into said first widening, thereby pulling said first widening element towards said second widening element. Alternatively or additionally, said tip is mounted on a tip-shaft and said tip is retracted by retracting the tip-shaft and wherein said tip shaft is coupled to said shaft, such that after sufficient retraction of said tip shaft, said tip shaft engages said shaft and retracts it.

There is also provided in accordance with a preferred embodiment of the invention, a method of everting a graft, comprising:

grasping said graft between an internal mandrel and an outer tube; and pushing an end of said graft back over said graft. Preferably, the method comprises repeating said pushing a plurality of times to achieve a desired amount of eversion. Alternatively or additionally, pushing said end of said graft comprises everting the end over said outer tube.

There is also provided in accordance with a preferred embodiment of the invention, a graft everter, comprising:

a tip adapted for mounting an end of said graft thereon;

a graft stop adapted for stopping an advance of said graft end over said tip; and a plurality of expanding fingers disposed between said graft stop and said tip, said fingers having an expanded state in which they have an external diameter larger than said tip and larger than said graft and an unexpanded state in which the diameter does not suffice to engage said graft.

There is also provided in accordance with a preferred embodiment of the invention, a method of mounting an anastomosis connector having spikes with tips that bend out of a lumen of said connector, on a graft, comprising:

maintaining said at least some of said spikes in a twisted configuration such that tips of said spikes bend into the lumen;

transfixing said graft on said tips; and changing the configuration of said tips to bend out. Preferably, changing the configuration comprises releasing said spikes.

There is also provided in accordance with a preferred embodiment of the invention, a method of simulating eversion of a graft, comprising:

compressing an end of said graft into a form to provide a thickening of said end; and transfixing said thickening with at least one spike of an anastomosis connector. Preferably, said graft comprises a mammary artery. Alternatively or additionally, said transfixing comprises transfixing along an axis of said graft. Alternatively, said transfixing comprises transfixing oblique to an axis of said graft. Alternatively, said transfixing comprises transfixing perpendicular to an axis of said graft.

In a preferred embodiment of the invention, said form comprises an inner mandrel.

Alternatively or additionally, said form defines, on said graft, a flat end surface for said thickening. Alternatively, said form defines, on said graft, an oblique end surface for said thickening. Alternatively, said form defines, on said graft, an non-planar end surface for said thickening.

There is also provided in accordance with a preferred embodiment of the invention, a method of transfixing a connector on a graft, comprising:

widening a radius of an end of the graft;

advancing at least one spike of said connector, parallel to said graft, such that it transfixes said widened area; and bending at least an end of said spike to form a hook.

There is also provided in accordance with a preferred embodiment of the invention, a kit for a bypass procedure, comprising:

at least one graft having anastomosis connectors mounted on two ends thereof, said graft and said connectors adapted for a peripheral bypass procedure; and at least one guide wire attached to one end of said graft. Preferably, said connectors are embedded in said ends of said graft.

There is also provided in accordance with a preferred embodiment of the invention, an oblique hole punch, comprising:

a shaft;

a first non-circular edge oblique to said shaft at a first angle;

a second non-circular edge oblique to said shaft at a second angle; and means for reducing a gap between said tow edges, so as to cut through vascular tissue placed between them. Preferably, said two angles are different. Alternatively, said two angles are the same.

There is also provided in accordance with a preferred embodiment of the invention, a penetrating punch for punching holes in a blood vessel during a keyhole procedure, comprising:

a tip for puncturing said vessel;

a rigid handle, adapted for keyhole surgery and coupled to said tip, for controlling a spatial position of said tip;

two surfaces for receiving the walls of the vessel surrounding said puncture; and means for bring said surfaces together for punching said hole. Preferably, said tip is smooth. Alternatively, said tip is axially grooved.

There is also provided in accordance with a preferred embodiment of the invention, a method of heat-treating an anastomosis connector, comprising:

fitting a cut connector into a mold;

fixing said mold to bend both forward and backwards spikes of said connector into a desired configuration; and heat-treating said fixed connector, thereby training it to said configuration.

BRIEF DESCRIPTION OF THE DRAWINGS

The invention will be more clearly understood by reference to the following description of preferred embodiments thereof in conjunction with the figures, wherein identical structures, elements or parts which appear in more than one figure are labeled with the same numeral in all the figures in which they appear, in which:

FIGS. 2A–2F schematically illustrate the operation of the device of FIGS. 1A–1D, in accordance with a preferred embodiment of the invention;

FIGS. 4A–4D illustrate a method of retracting a ring portion of the anastomosis device of FIGS. 1A–1D, in accordance with a preferred embodiment of the invention;

FIG. 8B is a top view of the connector of FIG. 8A, in a resting state;

FIG. 8C is an enlargement showing the meeting of two spikes from opposing sides of the connector;

FIG. 8D is a view through line A—A of FIG. 8B, showing the relative placement of the spikes from two sides of the anastomosis device, in a resting state;

FIGS. 12A–12D illustrate a process of using a grab-and-cut punch, in accordance with a preferred embodiment of the invention;

FIGS. 13A–13D illustrate a process of using a rotating spike hole puncher, in accordance with a preferred embodiment of the invention;

FIGS. 20A–20D illustrate a connector mounting method in accordance with a preferred embodiment of the invention;

FIGS. 21A–21E illustrate a graft everter, in accordance with a preferred embodiment of the invention;

DETAILED DESCRIPTION OF PREFERRED EMBODIMENTS

Performing an anastomosis connection with a coronary vessel may be a first or a second step of performing a bypass between an aorta and the vessel or it may be a single anastomosis step in a longer process, for example when connecting a LIMA or a RIMA to a coronary using a side-to-end anastomosis connection. In some cases this anastomosis connection is problematic for example for one or more of the following reasons:

(a) The coronary vessels and especially diseased ones have a very weak structure and are difficult to handle and stretch.

(b) At the end of the procedure, and in some embodiments, for substantially all of the procedure, the tools used for performing the anastomosis are all outside the graft and the coronary.

(c) It is generally not desirable that the anastomotic connector be long (in an axial dimension), as a minimal intra-body profile is desired.

(d) It is generally desired to manipulate the blood vessels, especially the coronaries, as little as possible. It is thus useful if darning of the blood vessels is avoided.

Two Part Anastomosis Connector Device

Figure 1A:
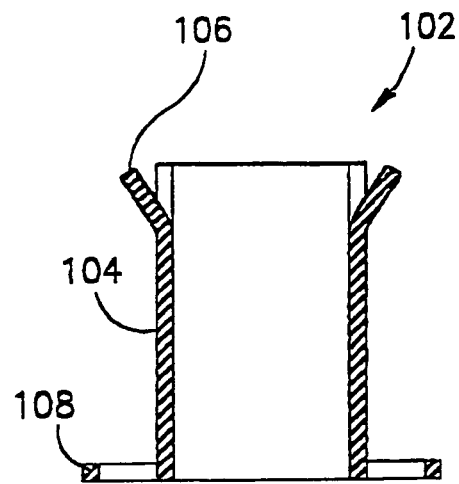
FIGS. 1A–1D schematically illustrate two parts of a two part anastomotic device of a preferred embodiment of the present invention, in isometric-perspective and in cut-through views.
Figure 1B:
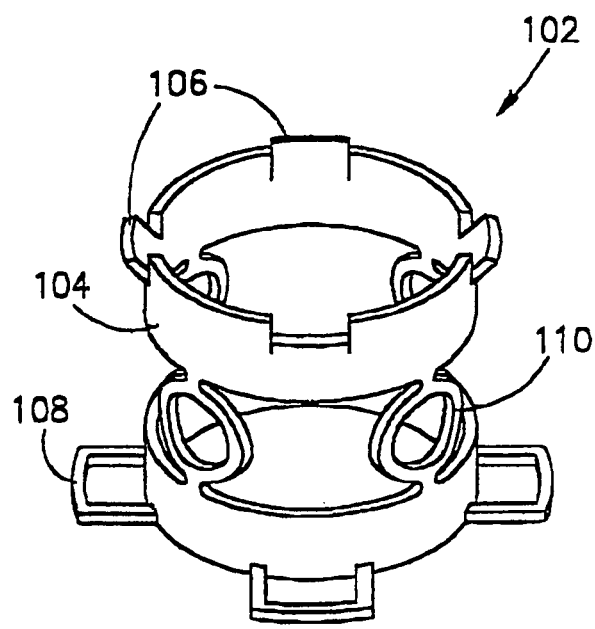

FIGS. 1A–1D schematically illustrate two parts of a two part anastomotic device 100 of a preferred embodiment of the present invention, in isometric-perspective and in cut-through views. FIGS. 1A and 1B illustrate a ring portion 102, preferably formed of a tubular element 104. Optionally, a plurality of apertures 110 are formed in the tubular element. Alternatively or additionally, the tubular element may be formed of a mesh or another construction that is naturally open. Thus, the total amount of foreign material in the body is preferably reduced. Optionally, tubular element 104 can radially expand or contract, for example plastically, elastically, super-elastically or using shape-memory. Another possibly advantage of using a mesh element is that the anastomosis device is more flexible and can accommodate variations in tissue geometry and can even deform over time, for example if the vessels enlarge.

A plurality of flange elements 108 are preferably provided around the circumference of tubular element 104. Preferably, each of these flange elements has an aperture defined in it and are used to hold a spike element (described below). Alternatively or additionally, these flange elements function as a flange over which a blood vessel is everted and/or otherwise attached to. Optionally, the flange elements of the tubular element include barbs to engage an everted blood vessel. Alternatively or additionally, the flange elements serve to stiffen the tube element so that it does not collapse radially.

Thus, the graft is engaged by tubular element 104. In some cases, the engagement is by contact, in others, a mechanical coupling is provided, for example, friction, using barbs on element 104, using glue, or as a result of eversion over the flange.

A plurality of locking elements 106 are preferably provided on tubular element 104, for example on an opposite side from the flange elements, to lock the spike elements in place when anastomosis device 100 is deployed. In a preferred embodiment of the invention, the locking elements are elongate, so that their length provides some elasticity with respect to the locking. Thus, some relative elastic motion of the spikes and the tubular element is possible even after locking. Alternatively, other types of axial motion allowing mechanisms may be provided, for example making the spikes axially elastic (with respect to the forces expected in the anastomosis connection).

An elastic locking device is preferably achieved by providing or placing the locking elements distal from the flange of tubular element 104. However, in other embodiments, for example if the locking elements themselves include springs or are comprises of an elastic material, the locking elements may be near the flange or even on the flange. Additionally, the locking elements can be at or near the flange for other reasons, for example, if no elastic motion is desired.

Figure 1C:
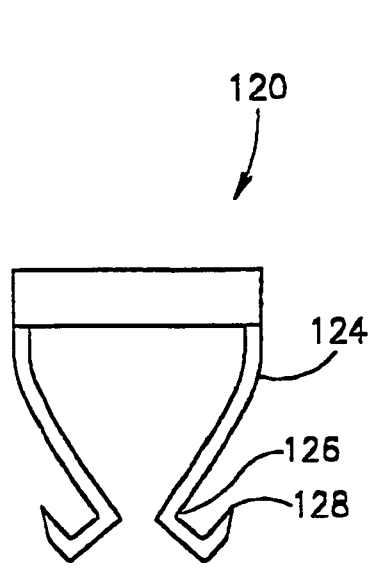
Figure 1D:
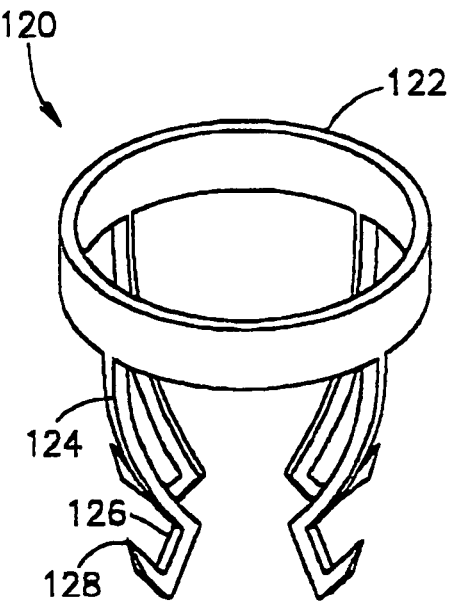

FIGS. 1C and 1D illustrate a spike-portion 120, preferably formed of a ring 122 having a plurality of spikes 124 attached thereto. In a preferred embodiment of the invention, the diameter of the ring is slightly greater than that of tubular element 104. It is noted however, that in some preferred embodiments of the invention one or both of ring portion 102 and spike portion 120 are radially expandable. In a preferred embodiment of the invention, spike portion 120 is mounted on ring portion 102 by inserting each of spikes 124 through a flange element 108 while sliding ring 122 over tube element 104. In some implementations, flange elements 108 are open ended, rather than closed, as shown.

In a preferred embodiment of the invention, when anastomosis device 100 is assembled, the spikes are pushed through the apertures of closed flange elements. Alternatively, the spikes may be slid in through an opening. In another embodiment, the openings are on the sides of the flange elements and spike portion 120 is mounted onto ring portion 102 by rotating the spike portion 120 so that the spikes enter the flange elements through the openings.

Ring 122 is preferably relatively rigid. However, in some embodiments, where ring 122 is not required to maintain its shape, but mainly assist in retracting spikes 124, the ring may be made more flexible. It should be noted that ring 122 may be open, however, it is preferably a closed ring. Preferably, locking elements 106 (FIGS. 1A, 1B) operate by engaging ring 122, once it is retracted over them.

In an alternative embodiment, ring 122 is sine-shaped, with the spikes connected to parts of the sine distal from the flange. Thus, when the ring relaxes, it retracts the spikes.

Spikes 124 may be of many different designs. However, in a preferred embodiment of the invention, the spikes are curved inwards towards their ends and have a bent end 126, with a sharp tip 128. In some embodiments, especially as described below, spikes 124 may include a twist. The curve of the spikes is preferably super-elastic, in that the spikes are pre-formed to be bend and are maintained in a straightened configuration during at least part of the deployment process. However, elastic, plastic, shape memory and other mechanical types of bending may also be practiced in preferred embodiments of the invention.

Figure 2B:
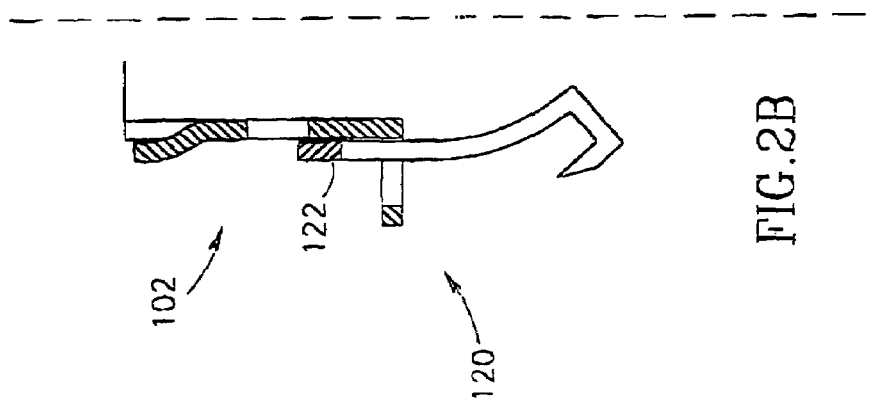
Figure 2A:
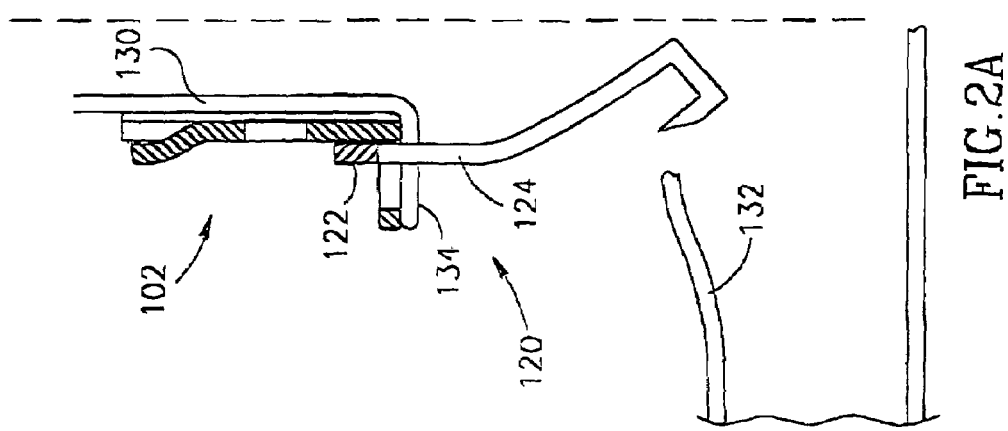
Figure 2F:
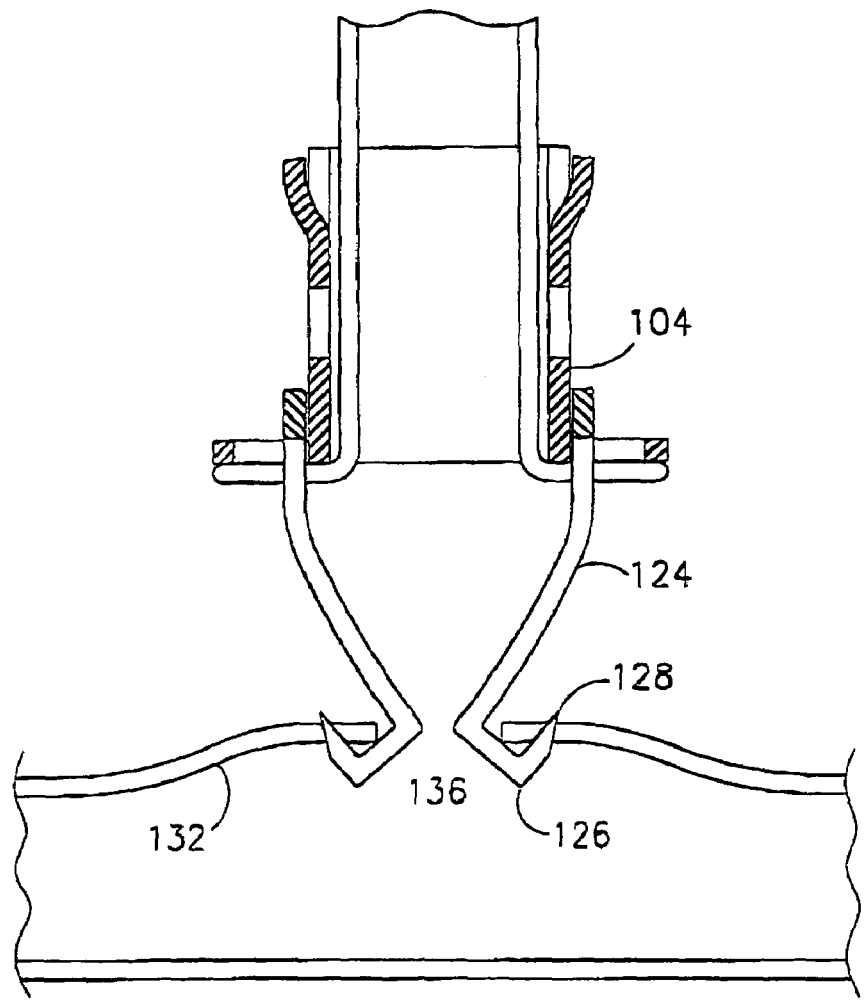

FIGS. 2A–2F schematically illustrate the operation of anastomosis device 100, shown in a side cross-sectional view. FIG. 2A shows anastomosis device 100 after it is mounted on a graft 130, such that a spike 124 transfixes a partially everted portion 134 of the graft (e.g., everted less than 180°). In this embodiment, the spikes are curved in, such that when ring 122 is retracted, as shown in FIG. 2B, the spikes are straightened by the ring portion 102, preferably by flange elements 108. After they are straightened or during the straightening process a target vessel 132 is preferably transfixed by tips 128 of the spikes. Alternatively, as shown in FIG. 2F, the spike tips transfix vessel 132 even before the spikes are unbent. In some embodiments, the spikes flare out as well, for example to widen the opening and/or to otherwise geometrically mold the connection between the blood vessels.

The effect of strengthening the spikes is achieved, in some embodiments by relative motion of the two connector parts. In some embodiments, this motion includes retraction of the spikes relative to vessel 132. Alternatively, the spikes are maintained in a fixed position in space relative to vessel 132 or even advanced.

FIG. 2C illustrates an alternative to FIG. 2A, in which the spikes are not bent inwards. An opening 136 in the target vessel may be widened during the insertion of the spikes or the spikes may be bent inwards, for example by an enclosing tube. Other methods of bending the spikes may also be used, for example, using torsion forces, or by temperature treating shape-memory formed spikes. Alternatively, bent end 126 may be sharp enough to transfix the target vessel when the spikes are advanced. Optionally, tip 128 is compressed against spike 124, so bent end 126 has a smaller profile.

In a preferred embodiment of the invention, vessel 132 is perfused, for example using blood, saline solution, possibly through its lumen and possibly through opening 136, so that the walls of vessel 132 are separated.

Once ring 122 is retracted sufficiently, locking elements 106 preferably engage the ring and/or the spikes, locking them in place. FIG. 2D shows a final state in which spike tips 128 contact or lock against the bottom of the flange elements or into the flange elements. FIG. 2E shows a final state in which spike tips 128 contact or lock against the side of flange elements. Possibly, the spike tips neither contact nor lock against the flange elements. It is noted that by controlling the configuration of the anastomosis device and the eversion, spike tips 128 can be made to pierce or to not pierce everted portion 134 of graft 130. Although tips 128 may transfix even everted portion 134, in a preferred embodiment of the invention, tips 128 are not exposed, to prevent them catching on other, nearby, tissue and damaging it. Thus, in some embodiments of the invention, including those described elsewhere herein, when a vessel is transfixed, the piercing of the vessel may be through or it may be part way.

Figure 3A:
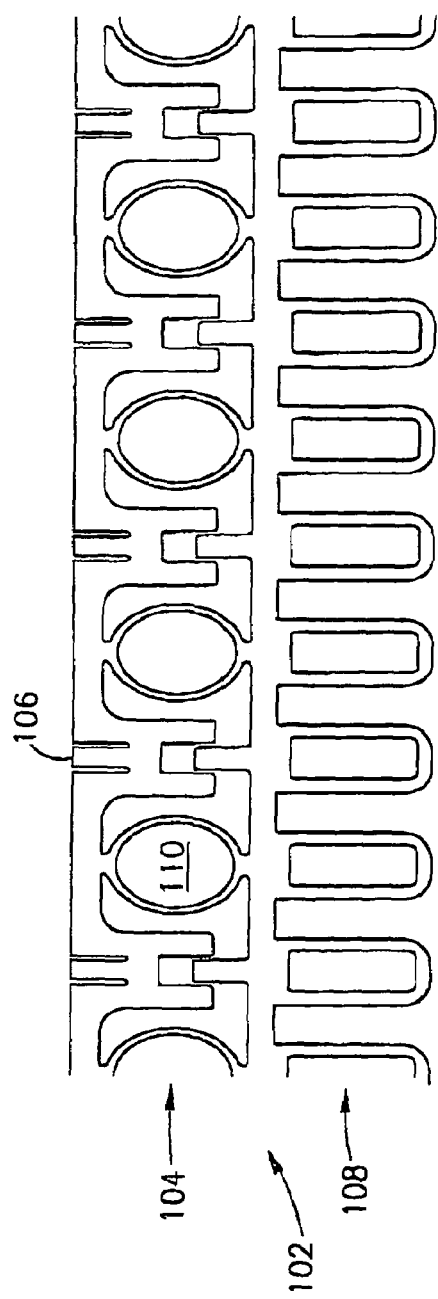
FIGS. 3A and 3B are plan layouts of the two parts of the anastomotic device of FIGS. 1A–1D, in accordance with a preferred embodiment of the invention.

FIG. 3A is a plan layout of ring portion 102, in accordance with a preferred embodiment of the invention.

Figure 3B:
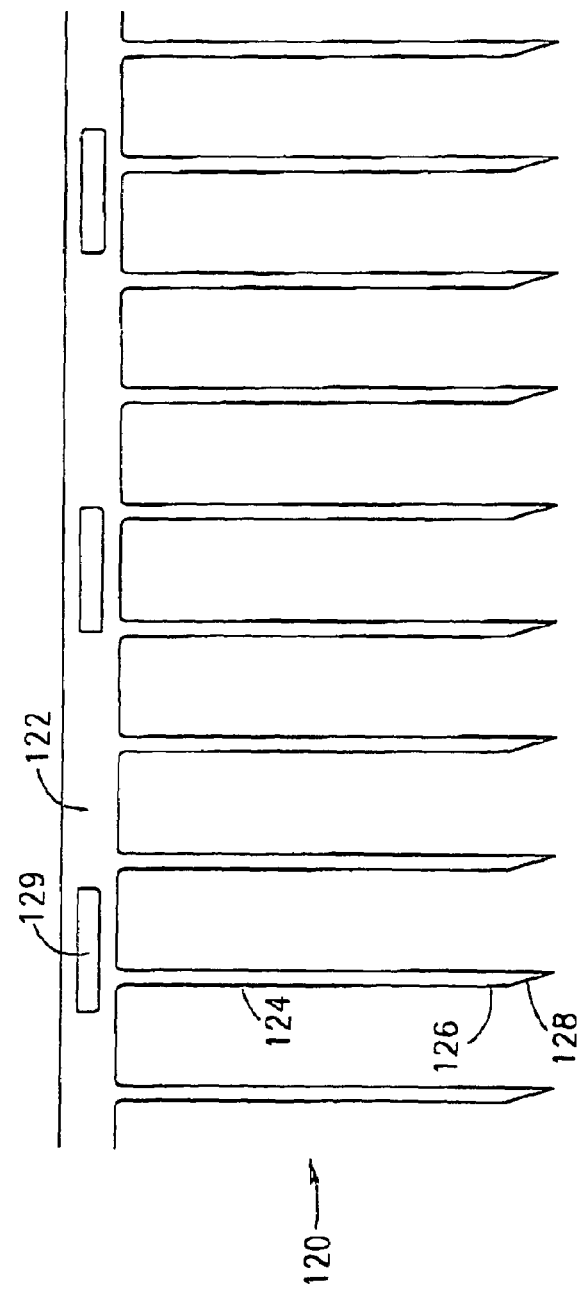

FIG. 3B is a plan layout of spike portion 120, in accordance with a preferred embodiment of the invention. A plurality of optional openings 129 are shown in ring 122.

FIGS. 4A–4D illustrate a method of retracting a ring portion of the anastomosis device of FIGS. 1A–1D, in accordance with a preferred embodiment of the invention. A schematically shown insertion tool 140 preferably includes a ring retractor 142 having a ring engaging portion 144. Ring engaging portion 144 may be designed to engage openings 129. Alternatively or additionally, ring engaging portion 144 may engage ring 122 from its underside. Many variations on ring engaging portion 144 are possible, however, in a preferred embodiment of the invention, engager 144 comprises a plurality of fingers which when retracted away from vessel 132, pull ring 122 along with them. An advantage of these fingers engages openings 129, is that they provide a method of advancing the ring 122.

Figure 4A:
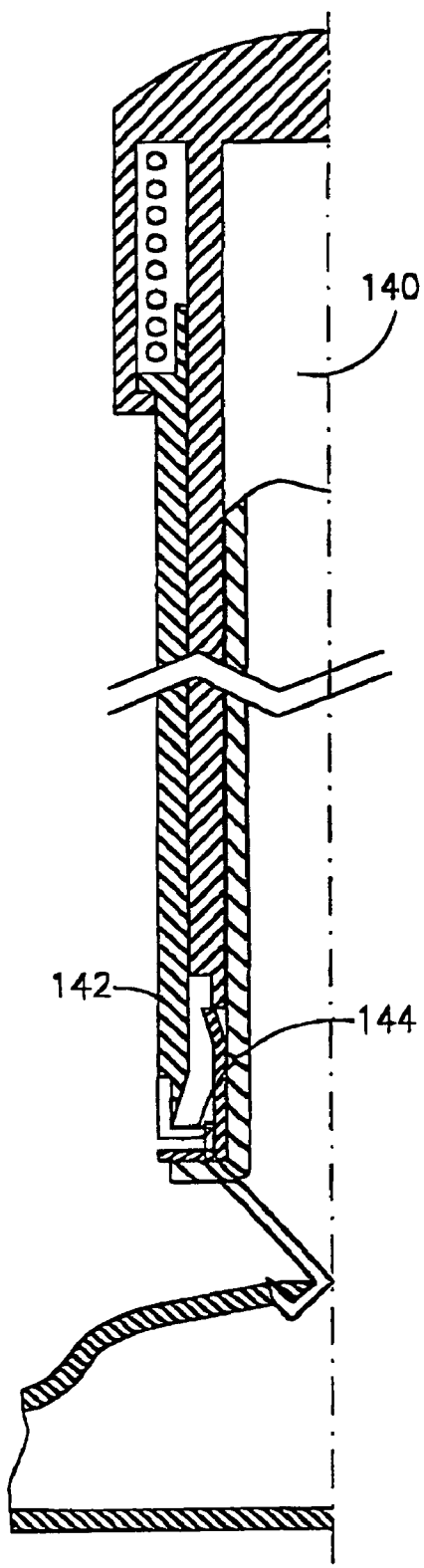
Figure 4B:
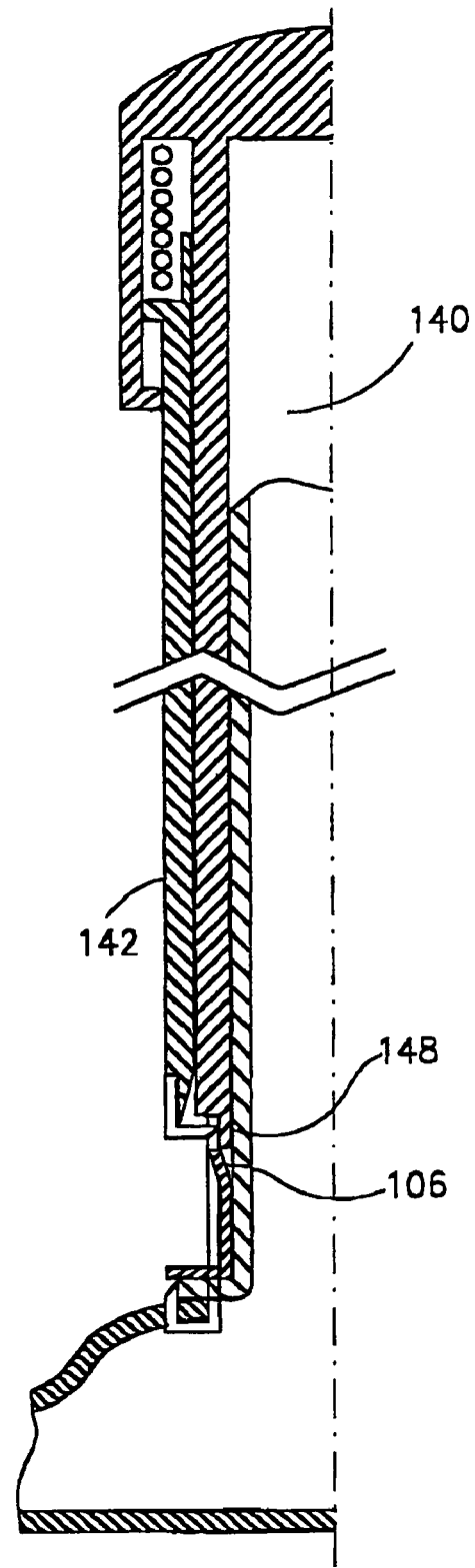

When ring retractor 142 is retracted, for example as shown in FIG. 4B, ring 122 and spikes 124 are also retracted. When the retraction is sufficient ring 122 is engaged by a locking element 106. Optionally, an extension 148 of insertion tool 140 prevents engagement of the locking elements until the extension is retracted, allowing correction of errors. In a preferred embodiment of the invention, locking element 106, when it engages ring 122, disengages the engager 144, for example by pushing the engaging fingers away radially. Alternatively, engager 144 may compress locking elements 106, thereby preventing their operation. Removing the device may include pushing in locking elements 106 and/or advancing the spikes so that they bend inwards. Possibly, it is required to grip vessel 132, so that the spikes retract from it.

As shown in FIG. 4C, in a preferred embodiment of the invention, when retractor 142 is pull beck further, engager 144 is bent out of the way by a protrusion (or thickening) 146 of tool 140. Thus, retracting ring 122, locking the anastomosis device and removing insertion tool 140 can proceed as a single smooth action. FIG. 4D shows the completed anastomosis after insertion tool 140 is removed. As shown, spike 124 typically, but not necessarily, digs into the side vessel, thereby having less exposed surface to the blood flow.

In a preferred embodiment of the invention, tool 140 does not surround the graft vessel from all sides, for example enclosing only 270° thereof. Thus, a slot is defined in the side of tool 140, through which the tool can be removed from the graft, once the anastomosis is completed.

Locking

In a preferred embodiment of the invention, the locking action of locking elements 106 against ring 122 is slightly flexible, to allow some adaptation to variations in local anatomy and especially to avoid applying too much pressure on the blood vessel portions compressed by the anastomosis device. In a preferred embodiment of the invention, the flexibility is set to match a desired range of pressures, for example, not so low that blood will leak and not so high as to cause tissue necrosis. Alternatively or additionally, this flexibility allows adaptation to variations in blood vessel thickness among blood vessels, among patients and/or in a single blood vessel. This flexibility may be provided in many ways, for example, by one or more of making locking elements 106 flexible, by making tubular element 104 flexible, by making spikes 124 axially flexible and/or by making bent area 126 of the spikes flexible. In an exemplary embodiment, the spikes include a spring portion, for example an S curve at their base, which spring portion can vary in length to modify the distance of the spike tip from a locking element or ring 122.

In a preferred embodiment of the invention, spikes 124 and especially the bending area 126 burrow into the "side" blood vessel 132, so that there is practically no contact between the spikes and the blood flow. However, the pressure on the spike is preferably regulated, for example as described above, to prevent necrosis.

Collar Length

Tubular element 104 serves as a collar when anastomosis device 100 is deployed. In some cases, the length of this collar may be a factor in the suitability of the anastomosis device. In a preferred embodiment of the invention, the collar is made as short as possible. alternatively, excess material may be cut off, for example after the anastomosis device is deployed.

It should be noted that an oblique connector (as described below) can have a generally lower profile relative to the blood vessel.

In an alternative embodiment of the invention, tubular element 104 is formed of two rings separated by a spring. Once the anastomosis is completed, the element is released and the collar contacts. Optionally, the contraction of the collar provides the locking function of elements 106, by engaging a portion of the spike between the two rings. Other structures which axially contract, for example a sine-shape, may also be used.

One Piece Anastomosis Device

Figure 5:
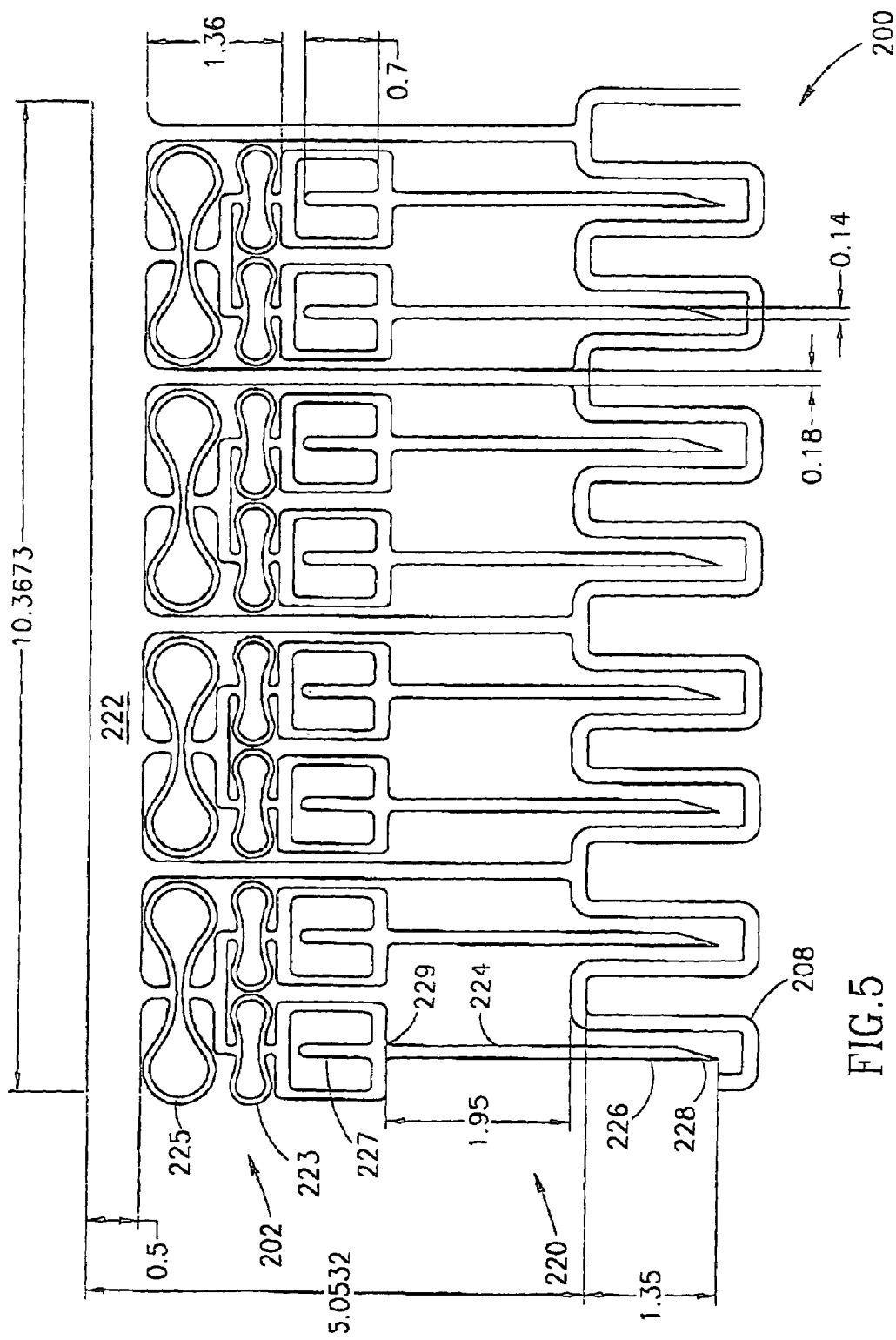
FIG. 5 is a plan layout of a one piece anastomosis device, in accordance with a preferred embodiment of the invention.

FIG. 5 is a plan layout of a one piece anastomosis device 200, in accordance with a preferred embodiment of the invention. A numbering scheme similar to that of FIGS. 3A and 3B has been used to illustrate the similarity between the anastomosis devices. An advantage of a one piece anastomosis device is the reduction or elimination of a need to control the relative orientation of two pieces. Alternatively or additionally, as there is only one piece, it is easier to grasp and is less likely to get lost in the patient's body. Also, as only one piece is provided, locking flanges may be dispensed with and spring action may be provided by dedicated springs 223 and 225. In the exemplary embodiment shown, springs 225 are used for the main retraction of the spikes, and springs 223 provide some flexibility with respect to the exact amount of retraction. In a typical use of the anastomosis device, a spike 224 is advanced by pressing on its associated stud 227. When the stud is released, the springs retract the spike. Optionally, the spike is forcefully retracted by engaging it at point 229, where the spike has a thickening.

In an alternative embodiment, at least one of the two springs 225 and 223 is plastically deformed, rather than elastically deformed.

Although locking is not required in a one-piece device, it may be provided. Optionally, a stop is provided to prevent the spikes from extending too far once they were retracted.

Figure 6B:
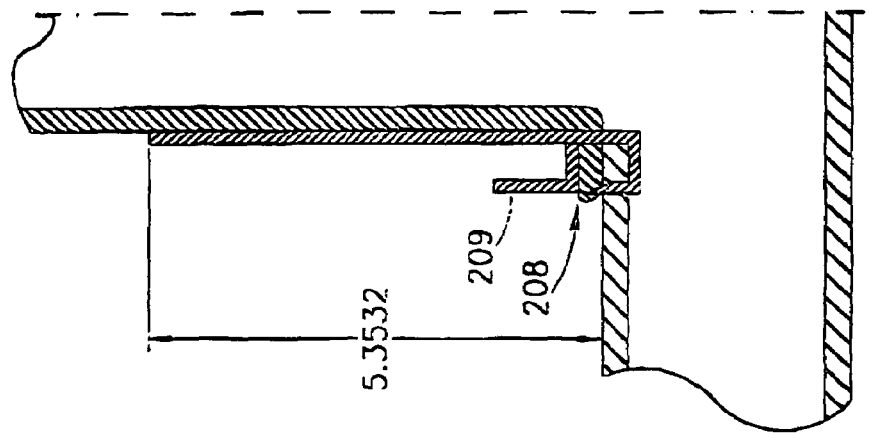
FIGS. 6A and 6B are side cut-through images of an anastomosis area, showing a method of performing an anastomosis using the device of FIG. 5.
Figure 6A:
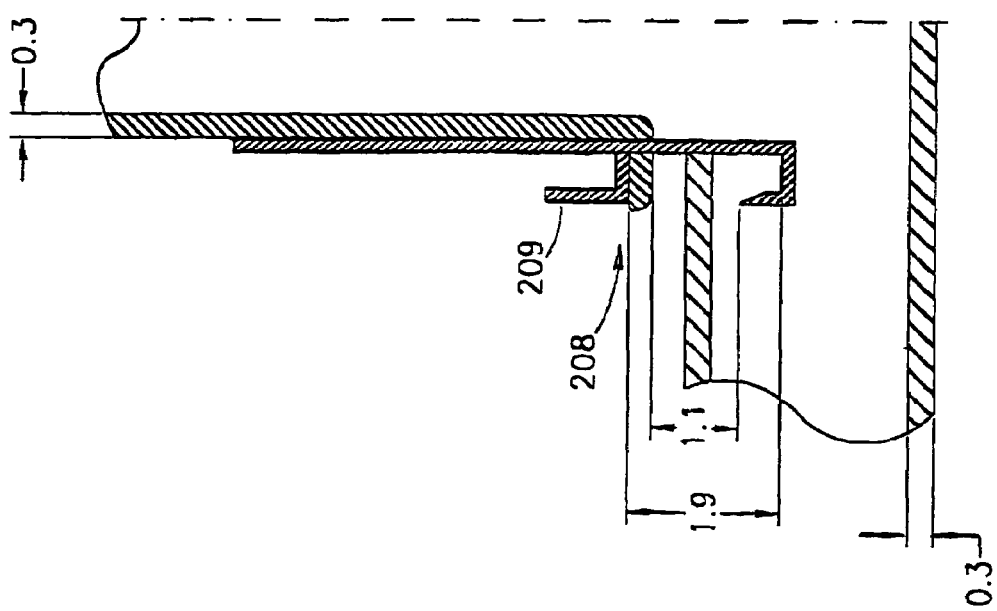

FIGS. 6A and 6B are side cut-through images of an anastomosis area, showing a method of performing an anastomosis using anastomosis device 200. As can be seen from the figures, the process is very similar to that of FIGS. 4A–4F, except that anastomosis device 200 is composed of only one piece and no locking is performed.

In these Figs., flange 208 is shown bent back up in a portion 209. This bending is optional, however, it may, for example, strengthen the anastomosis connection, protect the tips 228 of the spikes from causing damage to nearby body structures and/or allow pinching of vascular tissue by forcing the tissue with the spikes into the aperture of flange 208.

In anastomosis devices 100 and 200, a degree of elasticity with respect to the relative positions of the spikes is preferably allowed, as described above. In an exemplary embodiment, the freedom allowed is between 0.1 and 2 mm, for example about 0.5 mm or about 1.5 mm. The amount of freedom typically depends on the parameters of the anastomosis connections, including the pressures, the blood vessel geometries and the number of spikes used to make the connection.

Anastomosis Device Variations

Figure 7A:
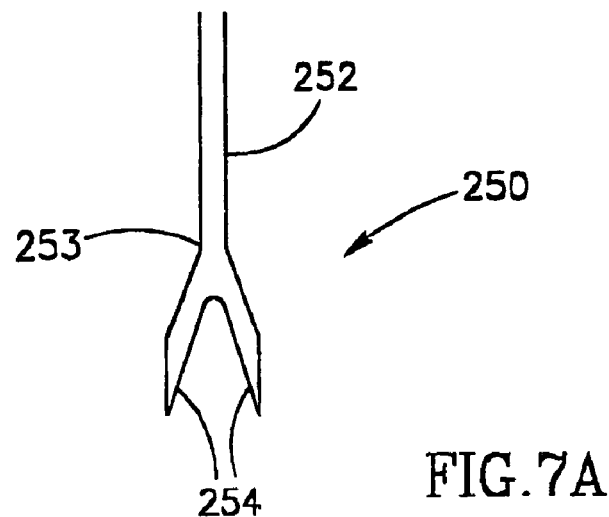
FIG. 7A is a schematic illustration of a splayed spike tip configuration, in accordance with a preferred embodiment of the invention.

FIG. 7A is a schematic illustration of a split spike tip configuration 260, in accordance with a preferred embodiment of the invention. This spike configuration is preferably used for an aortic type anastomotic connector, for example as described in PCT/IL99/00284, the disclosure of which is incorporated herein by reference. However, this type of spike configuration may be used for other anastomotic connectors. In a preferred embodiment of the invention, configuration 260 is used for holding the pierced blood vessel together, for example to prevent dissection, and not for exerting pressure either towards or away from the anastomotic connector. alternatively, the spike may also exert such radial pressure.

At a thickening point 253, a spike 252 splits into two tines 254. Preferably the tines are long enough to penetrate into the aorta (or other "side") vessel, but do not transfix it. Alternatively, they do transfix it. A different number of tines, such as one or three, possibly non-planar, may also be provided. Thickening 253 or the crotch of the split serves as a stop which prevents penetration of the spike to far into the aorta. Alternatively or additionally, as described below, the thickening is also used as an anchor point for manipulating the anastomosis device during deployment.

In a preferred embodiment of the invention, the tines vary in width and/or thickness, to resist retraction of the tines. Such geometric variations may also be provided on the spikes.

Figure 7B:
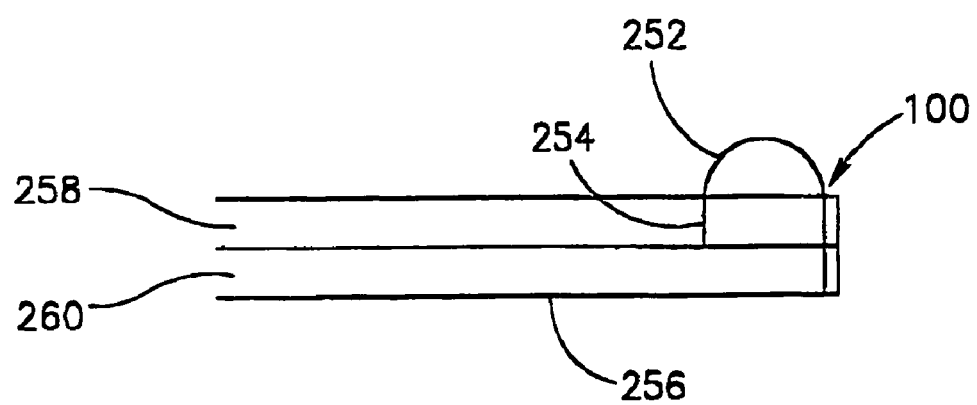
FIG. 7B is a side cut-through view of a connector including the configuration of FIG. 7A, deployed in an aorta, in accordance with a preferred embodiment of the invention.

FIG. 7B is a side cut-through view of a connector including configuration 250, deployed in an aorta 256, in accordance with a preferred embodiment of the invention. As shown, tines 254 hold together two aorta layers 258 and 260 (third, intermediate layer) is not shown.

Alternatively or additionally, a benefit of a fork shaped spike end is in assisting locking between the spikes on opposite sides of the anastomosis connection. To this end, needle-eye shaped tips, enclosing an aperture, rather than open tines, may be used. Alternatively or additionally, the tines (or spike itself) are barbed, to prevent retraction of the spike. Optionally, the spike is barbed along its length, to provide a ratchet mechanism, in which the spike can only advance one way. This can provide a self-tightening anastomotic connection, especially in conjunction with springs, as described above, that allow some relative motion between the spike and the anastomotic connector.

The spike cross-section is preferably that of a smoothed corner rectangle. However, other cross-sections may be used. For example, the cross-section may be triangular (e.g., facing away or towards the bend in the spike), circular oval or rectangular (e.g., with thick or thin side to the bend). Alternatively, the cross-section of the spike is not aligned with the bend direction. In addition, the cross-section may change over the length of the spike. This can be achieved, for example by chemical etching, laser cutting, cold working or twisting of the spike. An advantage of some of these spike cross-sectional configuration is that the provide maximum strength in a desired direction, while providing flexibility in other directions. Alternatively or additionally, the cross-section may better dig into the blood vessel and away from the blood flow. Also, some spike shapes are expected to cause less damage to at least some layers of the blood vessel, while being inserted.

Exemplary Embodiment

Figure 8A:
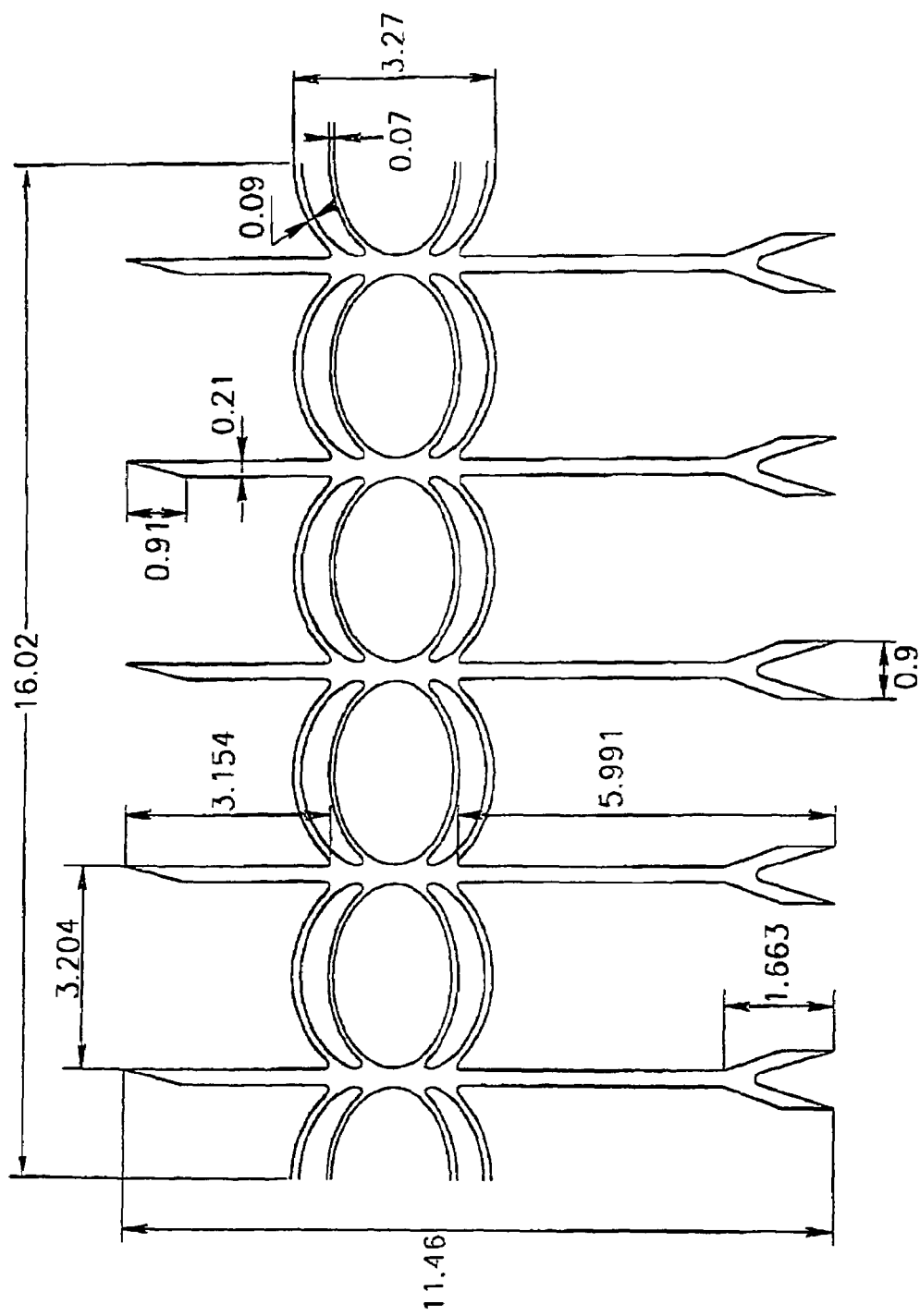
FIG. 8A is a plan layout of an aortic anastomotic connector in accordance with a preferred embodiment of the invention.

FIG. 8A is a plan layout of an aortic anastomotic connector in accordance with a preferred embodiment of the invention.

FIG. 8B is a top view of the connector of FIG. 8A, in a resting state.

FIG. 8C is an enlargement showing the meeting of two spikes from opposing sides of the connector.

FIG. 8D is a view through line A—A of FIG. 8B, showing the relative placement of the spikes from two sides of the anastomosis device, in a resting state.

Figure 9A:
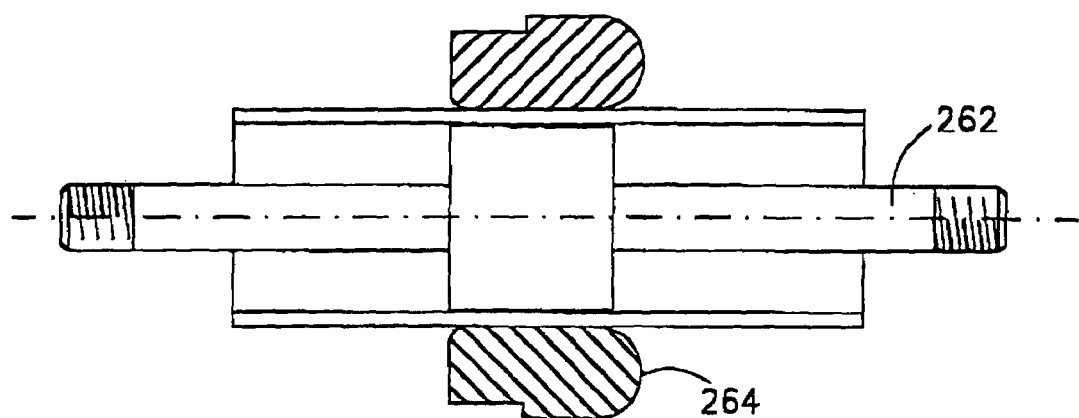
FIGS. 9A and 9B show a mold suitable for training the anastomosis device of FIGS. 8A–8D, in accordance with a preferred embodiment of the invention.
Figure 9B:
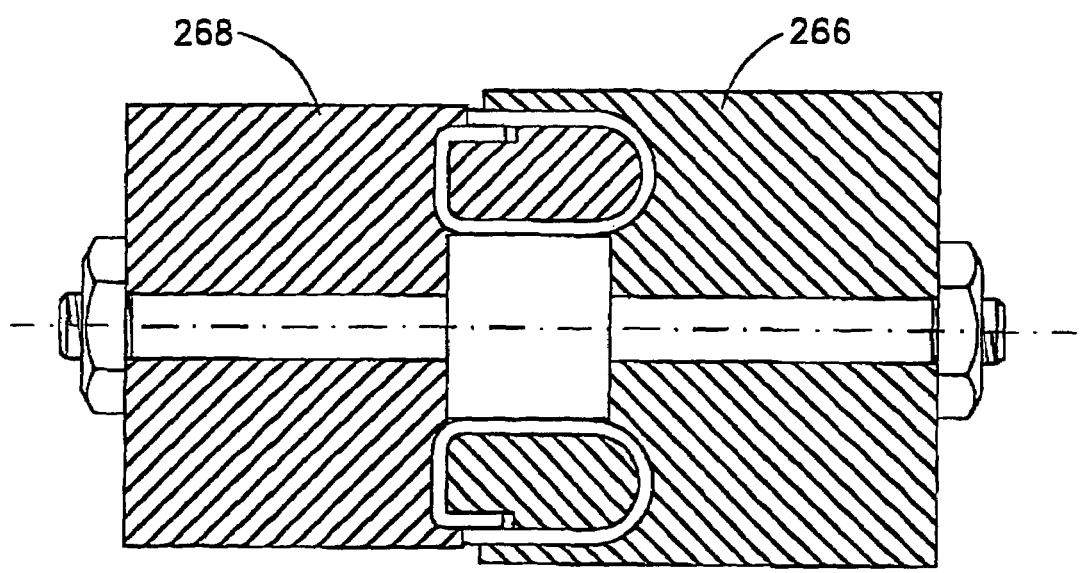

Exemplary measurements are provided on the figures, but they should not be considered limiting on the connector for other embodiments. The connector is preferably made of Nitinol, and is trained to the resting position shown using the molds of FIGS. 9A and 9B.

In an exemplary manufacturing method, a tube is laser cut as shown in FIG. 8A (or a plate is cut and then welded into a tube after being shaped on a mandrel) to form the connector. The tubular connector is preferably mounted on a mandrel 262, preferably an expandable mandrel that engages the connector snugly. Thereafter, the spikes of the connector are bent around a ring mold 264 and surrounded by a two part external mold having parts 266 and 268. The molded connector is then placed into an oven to be heat treated and then preferably quenched, for example in water. Then, the external mold is removed and ring mold 264 is also removed, for example by bending back the spikes. In a preferred embodiment of the invention, only a single heat-treatment is used for training the entire connector.

In an exemplary coronary anastomosis device, the diameter of the metal used for the spikes is between 0.07 and 0.1 mm, similar to the diameter of thread commonly used for bypass suturing. Tubular element 104 may be thicker, for example, 0.3 mm, however this is not essential.

Connector Material

In a preferred embodiment of the invention, the connector is formed of Nitinol, however, other materials may be used, for example stainless steel or a polymer, such as a plastic or a composite material. Possibly, a bio-degradable plastic is used. In some cases, the connector may be formed of two or more different materials, for example, each section of a different material or even a same section of two or more materials.

Alternatively, the connector is formed at least in part from allograft or xenograft materials. For example, ring 122 may be formed of sinew.

The graft is preferably an allograft, for example a mammary artery or a peripheral vein. Alternatively, other graft materials, including synthetic and other types of material known in the art may be used. In some cases, the connector is mounted on the graft outside the body, possibly in a remote location.

Deployment of Anastomosis Connector Device

Figure 10:
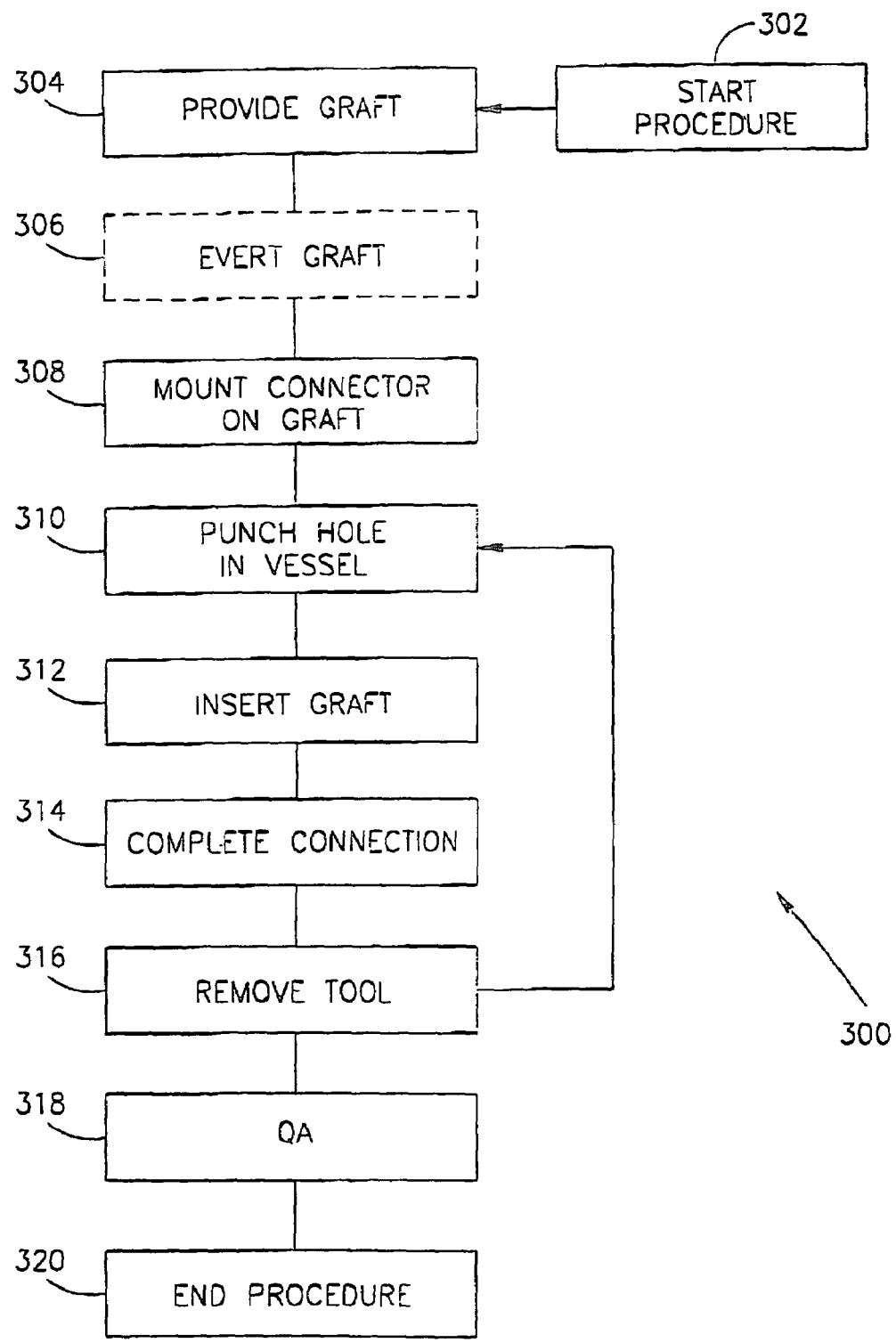
FIG. 10 is a flowchart of an exemplary process of keyhole bypass, in accordance with a preferred embodiment of the invention.

FIG. 10 is a flowchart of an exemplary process 300 of keyhole bypass, in accordance with a preferred embodiment of the invention. Many variations of the procedure can be performed, for example, the graft may be provided through a hole in the chest, through a blood vessel or be harvested in the chest region. In another example, although at least two connections are generally required for the bypass, one or both of the connections may be performed endoscopicly, transvascularly or using open surgery. Further, at least with respect to the connection distal from the coronary, one of the connections may be eliminated, for example if a mammary artery is used. Another type of variation is the time at which the graft is prepared for connection (e.g., when the connector is attached). This preparation can be done inside the body, or in a different country, in a two extreme examples. The time line of the process is also flexible, depending on the types of materials and techniques used. Process 300 is described as a generalized process, although account should be taken of the possible variations.

First, the by pass procedure is started (302). This usually involves opening one or more keyholes in the chest and/or other openings in the body. The heart may or may not be stopped and the vessel to be bypassed to may or may not be blocked.

A graft is provided (304). The graft may be harvested from the patient (e.g., a leg vein) or provided from a package. This may be done before or after the procedure proper has started. In some embodiments, the graft is a semi-connected or a disconnected mammary artery, which may be harvested and/or prepared through the keyholes.

A connector (e.g., 100 or 200) is mounted on the graft (308). Depending on the method used for mounting and for anastomosis, the vessel may be everted (306), before, during or after mounting the anastomotic connector.

Depending on the type of bypass, one, two or more connections between the graft and the patient's vascular system are required. Steps 310–316 describe one such connection.

In step (310) a hole is punched in the target blood vessel. Preferably, the puncher is left in the hole to prevent blood leakage from the punched hole.

The graft with the connector is then inserted in the hole (312). In some embodiments, the connector is partially deformed or allowed to deform into a partially deploy situation, before or after it is inserted.

The connection is then made (314), preferably by completing the deforming of the device, but in some embodiments, by pulling or pushing the device. An extra step of locking the device in the new configuration or of cutting away unnecessary portions of the device (neither steps shown), may optionally be provided.

The tool is then removed (316). In some embodiments, the tool surrounds the graft. The toll may be removed from the other end of the graft. Alternatively, the tool is dismantled. Alternatively, the tool is split apart. Alternatively, the tool is cut away from the blood vessel. Alternatively, the tool does not surround the graft from all sides, while it is in use.

The process of making a connection is repeated as many times as required. In some cases, also steps 304, 306 and/or 308 are repeated as well.

After one or both connections are made, a step of Quality Assurance (QA) 318 is preferably performed, in which the connections are inspected for leaks and/or to assure that the connectors are properly deployed. An exemplary check can be to see if all the spikes are properly deployed and pierce the vessels they are supposed to. The testing may be, for example, visual or radiographic.

The procedure is then completed (320), e.g., closing up the keyholes.

Various tools for performing steps of the above process, in accordance with preferred embodiments of the invention, are now described.

Exemplary Tool Set

Figure 11:
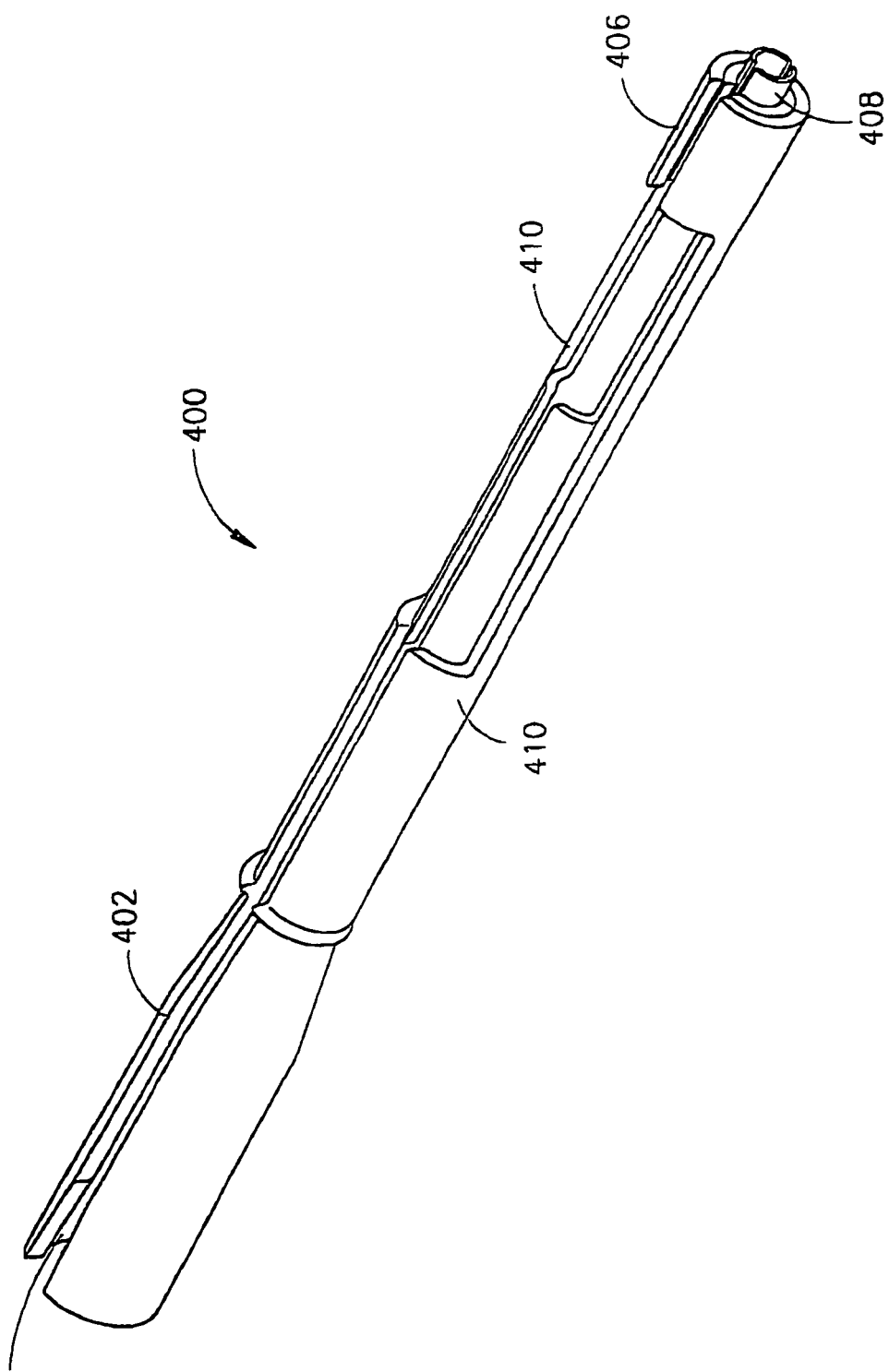
FIG. 11 is a schematic illustration of a scaffold tool, which holds various other tools during a bypass procedure, in accordance with a preferred embodiment of the invention.

FIG. 11 is a schematic illustration of a scaffold tool 400, which holds various other tools during a bypass procedure, in accordance with a preferred embodiment of the invention.

Tool 400 preferably includes a handle 402 and a shaft 401 extending from the handle.

A particular feature of this embodiment is a slot 404 extending along substantially the entire scaffold 400, which allows substantially free entry and exit of a graft vessel, although, as described below, it is sufficient for the slot to be present at the distal tip of the tool. A tip 408 of the tool is preferably formed so that it can fit inside a hole punched in a blood vessel during the anastomosis connection. An area 406, at the end of tool 400 preferably has high sides (e.g., it has a nearly complete circumference, except for a graft removal slot), to aid in maintaining the configuration of tools inserted inside scaffold 400, as will be explained below. In addition, area 406 serves as a stop which prevents unlimited insertion of tool 400 into a blood vessel. An area 410 has lower sides than area 406, to allow such inserted tools to split apart and free an enclosed graft as described below. Other configurations can also be used.

Tip 408 is preferably mounted on an extension which is separate from scaffold 400, and is retracted from it when it is time to remove the tools from the graft or during the deployment of the anastomosis connector. However, tip 408 is preferably present starting before the hold punching operation (at which point it is pushed into the punched hole) until after some or all the other tools are removed and the anastomosis completed.

Scaffolding tool 400 preferably includes alignment slots (not shown), to properly align tools inserted into it.

Tip 408 is preferably made of plastic, however, it may be made of metal. The rest of tool 400 is preferably formed of rigid plastic, as known in the art. Tool 400 may be disposable. Alternatively, it may be sterilized and reused, for example using sterilization methods known in the art.

In a preferred embodiment of the invention, tools which are inserted into scaffold 400 are mechanically split apart when they are retracted, if they enclose the graft. Thus, the graft can be removed from the tool. Alternatively or additionally, to mechanical splitting, the tools may be cut with a knife, possible one which forms a part of scaffold 400 or of the inserted tool. The inserted tool is preferably pre-formed with a slit (or two) to facilitate removal. Alternatively, most of the tool is open, for example formed like a bar, with only a ring at the tip to enclose the blood vessel. The tool may be damaged by the removal process so that it can only be used once. Alternatively, it is only plastically or elastically deformed, so that it can be bent back into shape, sterilized and reused.

Hole Punchers

When punching a hole in a blood vessel, several issues arise, some or all of which are preferably addressed by preferred embodiments of the invention:

(a) Avoiding a double puncture, in which the opposite side of the vessel is punctured.

(b) Avoiding inadvertent damage to the blood vessel caused by the movement of the punch.

(c) Avoiding loss of blood through the punched hole.

(d) Definite removal of the excised portion.

In a preferred embodiment of the invention, a punching operation consists generally of two steps:

(i) making a puncture in the target vessel using a tool; and (ii) punching a portion out of the blood vessel wall using the tool.

In a preferred embodiment of the invention, the motion of the punching tool, for step (i) and/or for step (ii) is achieved without axial motion of tool 400. Thus, minimizing the risk of double puncturing (a) and/or the risk of inadvertent damage (b).

Grab and Cut Punch

A first type of punching element is shown in FIGS. 12A–12D, as a hole puncher 420. As with the other tools described herein, hole puncher 420 may be designed for use with a scaffold tool 400, or for use as a stand-alone tool. In some embodiments of the invention, after the hole is punched tool 400 is brought (typically forcefully) over a portion of the punch which remains in the punched hole to prevent leakage and/or to guide in tip 408.

Hole puncher 420 comprises a tube 423 which splits into two (or more) flaring out tongues 424. Alternatively, the entire tube may be split. A sleeve 426 is provided so that when tube 423 is retracted, the tongues are brought together.

In FIG. 12A, a portion of a vessel 422 is engaged by the tongues, by pressing against the vessel.

In FIG. 12B, the tube is retracted a small amount and the tongues grasp a portion 428 of vessel 422. Preferably, as shown, tongues 424 have a cutting edge formed on their inner surface, mounted on a perpendicular section.

In FIG. 12C, tube 423 is further retracted, thereby cutting out portion 428.

The resulting vessel 422 with a punched hole is shown in FIG. 12D.

An advantage of some embodiments of this hole puncher is that by suitably setting the aperture defined by tongues 424, the puncher can avoid engaging both sides of the blood vessel at a same time. Alternatively to the engaging elements cutting the blood vessel, a separate cutter (not shown) may be used to cut the engaged portion 428.

Rotating Punch

FIGS. 13A–13D illustrate a process of using a rotating spike hole punch 430, in accordance with a preferred embodiment of the invention. Punch 430 preferably comprises an inner grasping element 432, preferably a vacuum tube and an external cutting element 434, preferably including at least one spike 436. FIG. 13B is a perspective view of external cutting element 434.

As shown in FIG. 13A, grasping element 432 is brought in contact with vessel 422 and engages it, for example using vacuum or using an internal grasper (not shown). Preferably, once vessel 422 is engaged, grasping element 432 is slightly retracted, to avoid inadvertently damaging the other side of vessel 422 while the hole is formed.

In FIG. 13C, cutting element 434 is advanced towards vessel 422, so that spike 436 penetrates it. By rotating the element 434, spike 436 cuts a round hole in vessel 422. Spike 436 is preferably straight and is slightly longer or the same length as the wall of vessel 422 is thick. Alternatively, other spike lengths or geometries may be used. In a particular implementation, spike 436 is sickle shaped and is inserted into vessel 422 using a rotational motion.

FIG. 13D shows vessel 422 with the resulting punched hole.

Anvil Punch

FIGS. 14A–14E illustrate a process of using an anvil hole puncher 440, in accordance with a preferred embodiment of the invention.

Figure 14A:
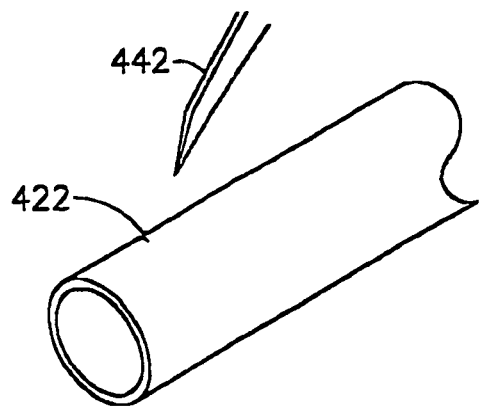
FIGS. 14A–14E illustrate a process of using an anvil hole puncher, in accordance with a preferred embodiment of the invention.
Figure 14B:
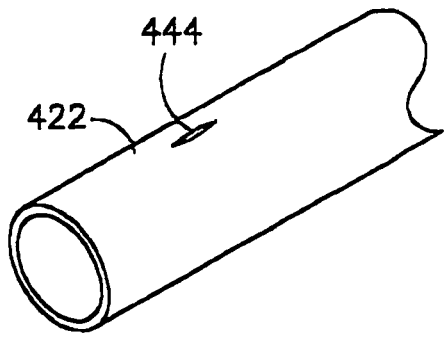

As shown in FIG. 14A and in FIG. 14B, a sharp edge 442 is used to form a slit 444 in vessel 422.

Figure 14C:
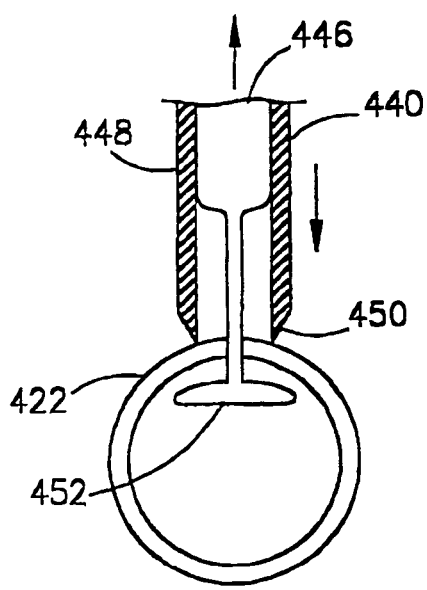
Figure 14D:
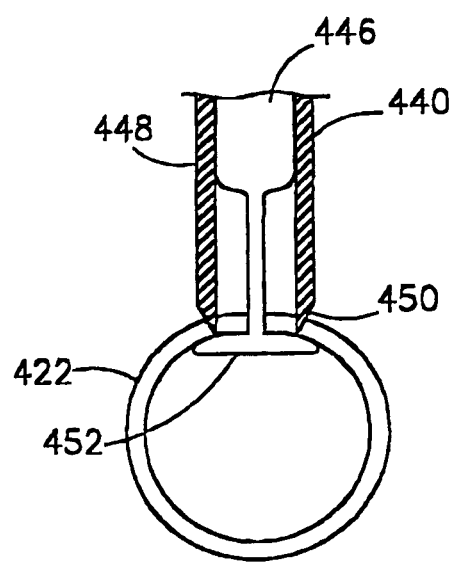
Figure 14E:
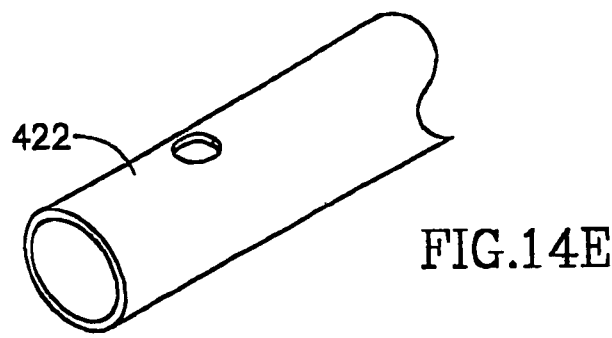

As shown in FIG. 14C, anvil hole puncher 440 comprises an inner element 446 having an anvil 452 formed at its end and an outer element 448 having cutting edges 450 formed at its end. Alternatively or additionally, the cutting edges and the anvil may trade places or only cutting edges may be used. Anvil 452 is inserted into vessel 422 through hole 444. Then, as shown in FIG. 14D, the anvil is retracted until vessel 422 is cut between anvil 452 and cutters 450. FIG. 14E shows the resulting punched hole.

Avoiding Blood Loss and Other Variations

In order to avoid blood loss, an enclosing tube (not shown, but could be tip 408) is preferably inserted into the punched hole. The enclosing tube preferably has a valve through which the punch is inserted and when the punch is removed, the valve seals and no blood leaks out.

The enclosing tube may be pushed into the hole. Alternatively or additionally, the tube may be screwed into the hole, for example by defining a thread on the tube's outside.

Alternatively or additionally, blood loss may be avoiding by perfusing vessel 422 with saline solution instead of or in addition to allowing blood flow. This preferably serves a purpose of preventing vessel 422 from collapsing, if it is weak or serves a purpose of clearing away blood. Such saline flow may also be provided through the hole puncher itself. An additional advantage of perfusing vessel 422 is that the side that is being worked on (punching, device connection) is thus distanced from the other side of the vessel, reducing the probability of damage to the other side of the vessel.

Integrated Hole Punch

FIGS. 15A–15D illustrate a hole puncher 460 designed to be inserted in scaffold tool 400, in accordance with a preferred embodiment of the invention. puncher 460 comprises a shaft 462 having at a distal end thereof a handle 464, for operating the punch and at the other end, a sharp tip 466 for piercing the blood vessel to be punched. Distal tip 466, the shaft defines a narrowing 468, into which the pierced blood vessel is guided, for example by pushing tip 466 forward, or by a back-angle (not shown) on tip 466. Distal of narrowing 468, is an anvil 470. Optionally, anvil 470 has an external angle, to assist in moving the punched blood vessel form the punch to tip 408 (of scaffold 400).

Figure 15A:
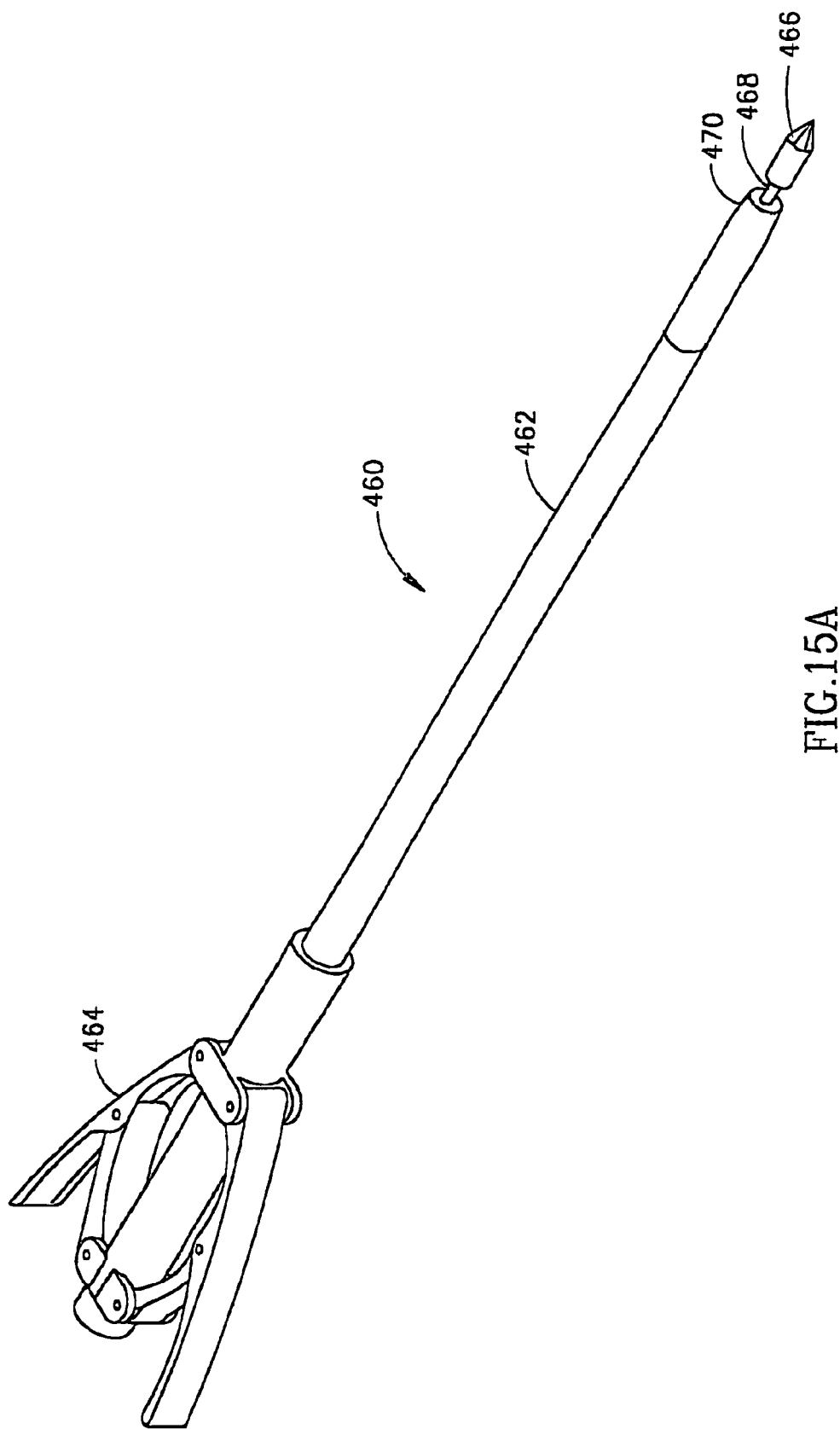
FIGS. 15A–15D illustrate a hole puncher designed to be inserted in the scaffold tool of FIG. 11, and its use in accordance with a preferred embodiment of the invention.
Figure 15B:
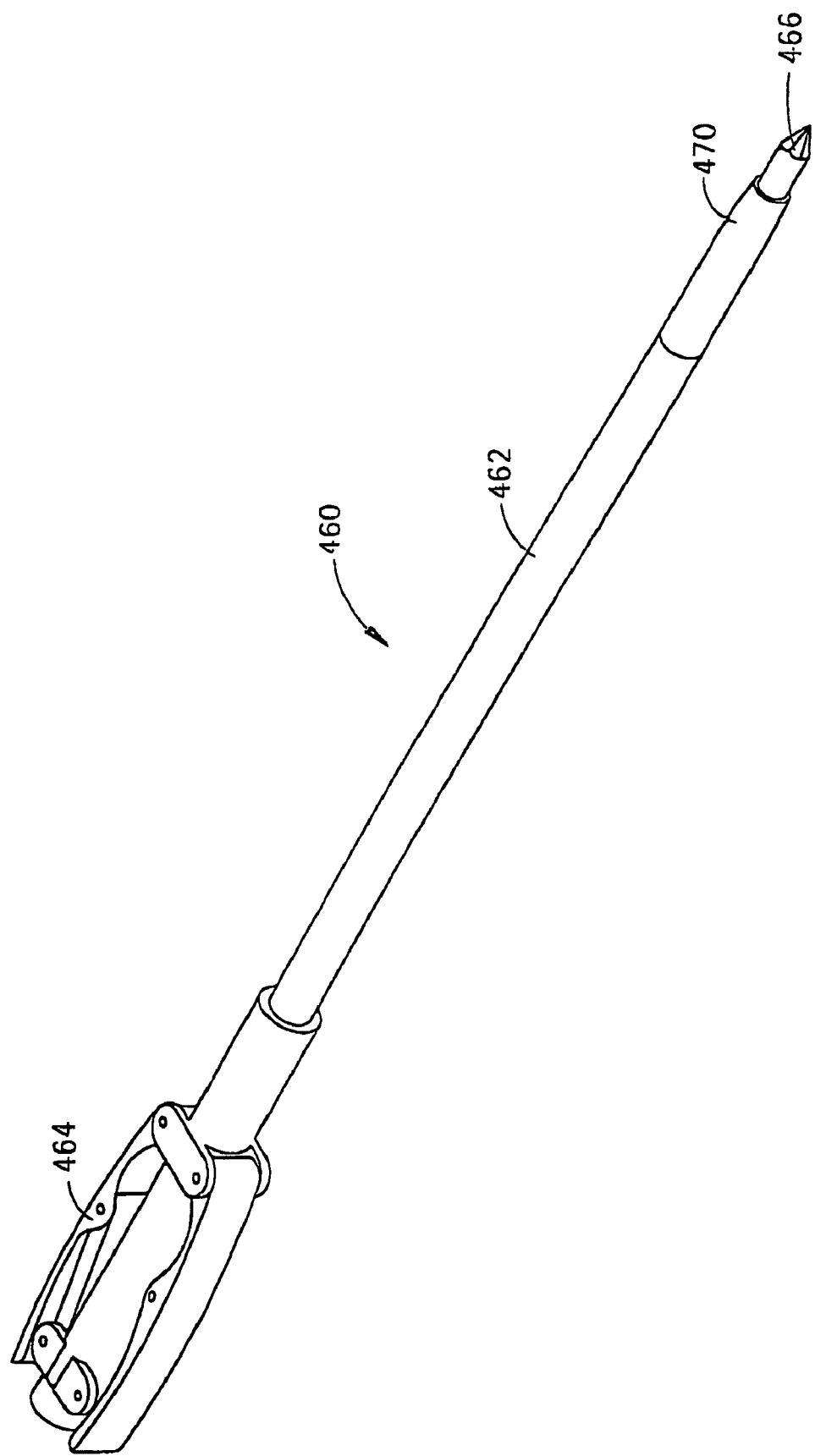

When the punch is operated, as shown in FIG. 15B, tip 466 is retracted relative to anvil 470, thereby punching a hole in the blood vessel.

Figure 15C:
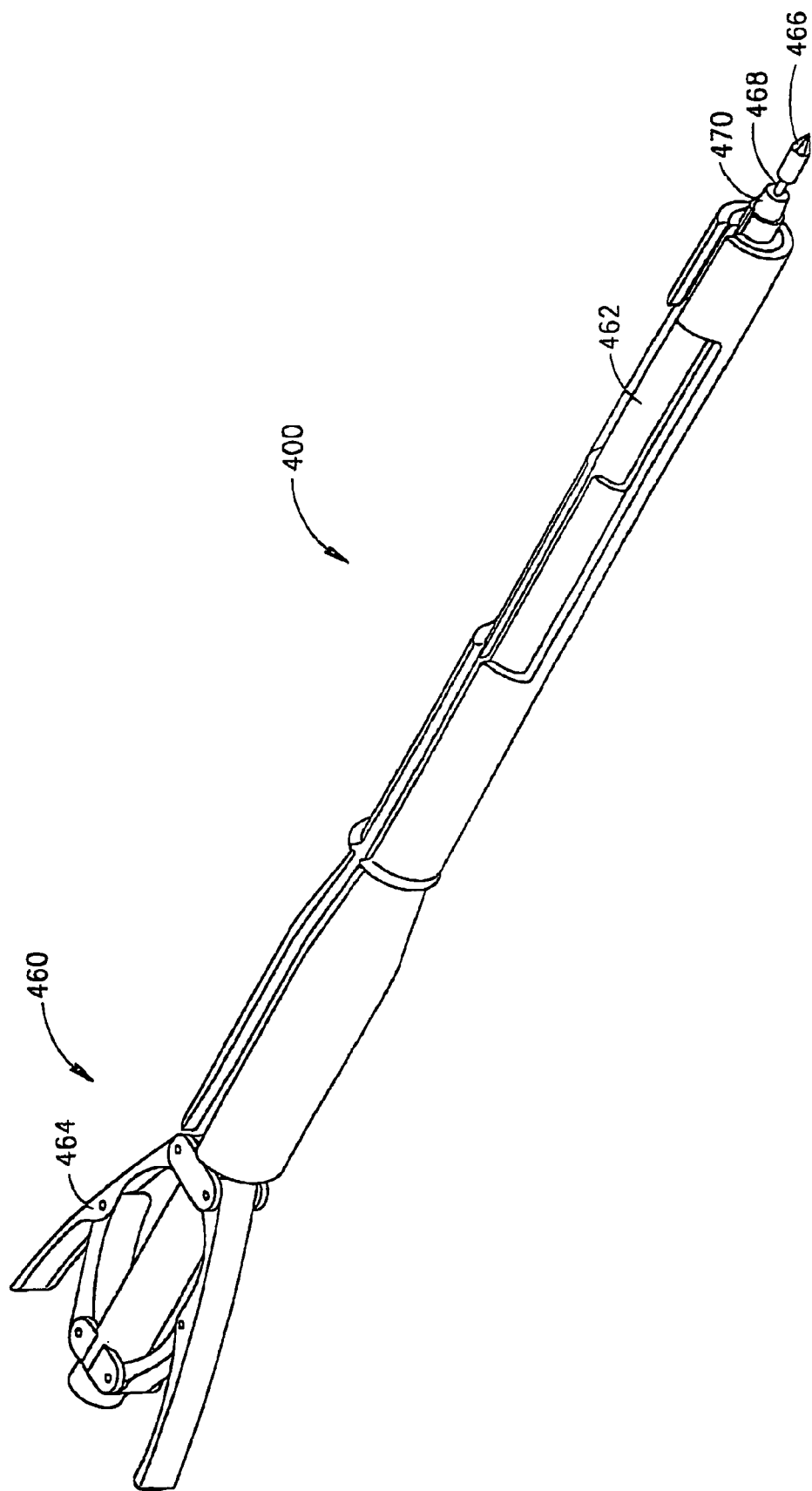

FIG. 15C shows punch 460 inserted in a scaffold 400.

Figure 15D:
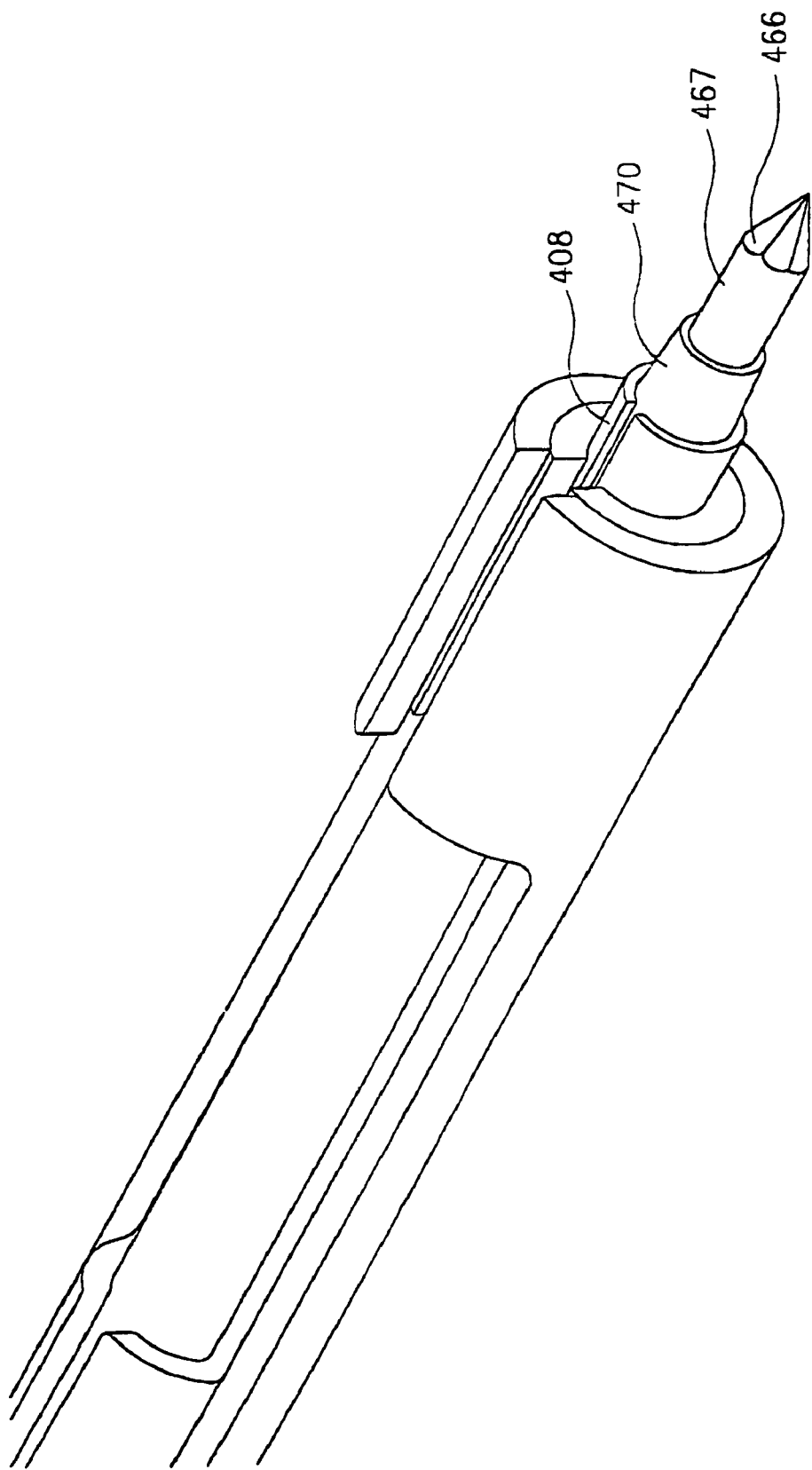

FIG. 15D is an enlargement of the proximal end of punch 460, inserted in scaffold 400, when the punch is operated. In a preferred embodiment of the invention, a fixed diameter area 467 is provided between anvil 470 and tip 466, to prevent the punched blood vessel from slipping off the punch. An incline is preferably provided in anvil 470, to assist in advancing the punched vessel onto tip 408 of scaffold 400.

Figures 16A, 16B:
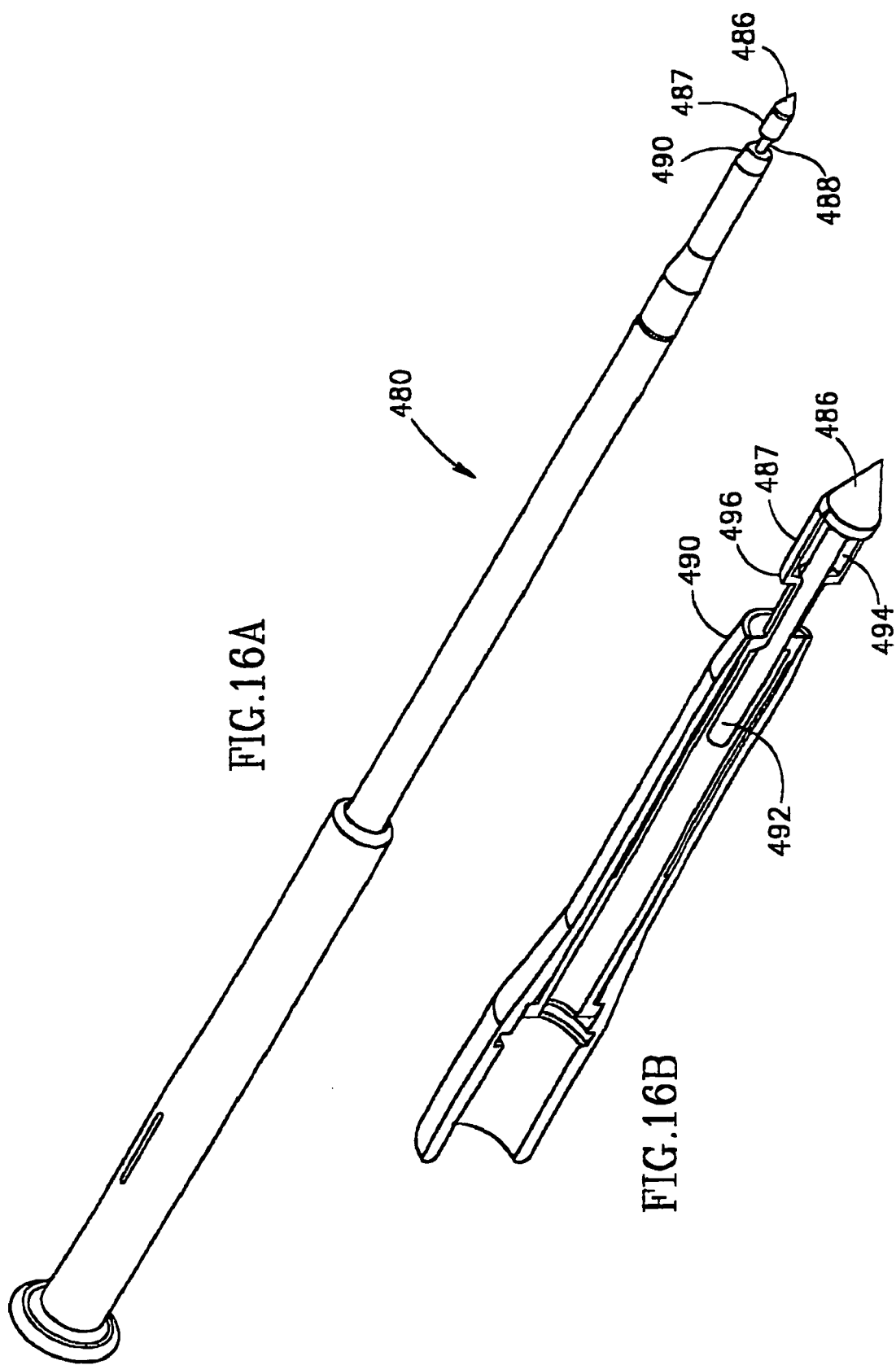
FIGS. 16A and 16B illustrate in perspective view and in perspective cut-open view, respectively, a tip-retracting hole punch, in accordance with a preferred embodiment of the invention.

FIGS. 16A and 16B illustrate in perspective view and in cut-open view, respectively, a tip-retracting hole punch 480, in accordance with a preferred embodiment of the invention. Punch 480 comprises a sharp retracting tip 486, an anvil 490, a narrowing 488 defined between tip 486 and anvil 490, and a cylindrical portion 487 between tip 486 and narrowing 488.

As shown in FIG. 16A, the punching action is caused by retracting tip 486, preferably using a shaft or cable 492 into a hollow 494 formed in cylindrical portion 487. When tip 486 is further retracted, cylinder 487 is pulled back against anvil 490, cutting the blood vessel in narrowing 488 between them using a ridge 496 defined on cylinder 487 and/or anvil 490.

In a preferred embodiment of the invention, scaffold 400 and/or tip 408 include a seal, for example an iris or leaflet seal, through which the punch can be inserted and retracted, while preventing leakage of blood as long as tip 408 is in the punched hole.

Alternative Retracting Tip Mechanism

Figure 17:
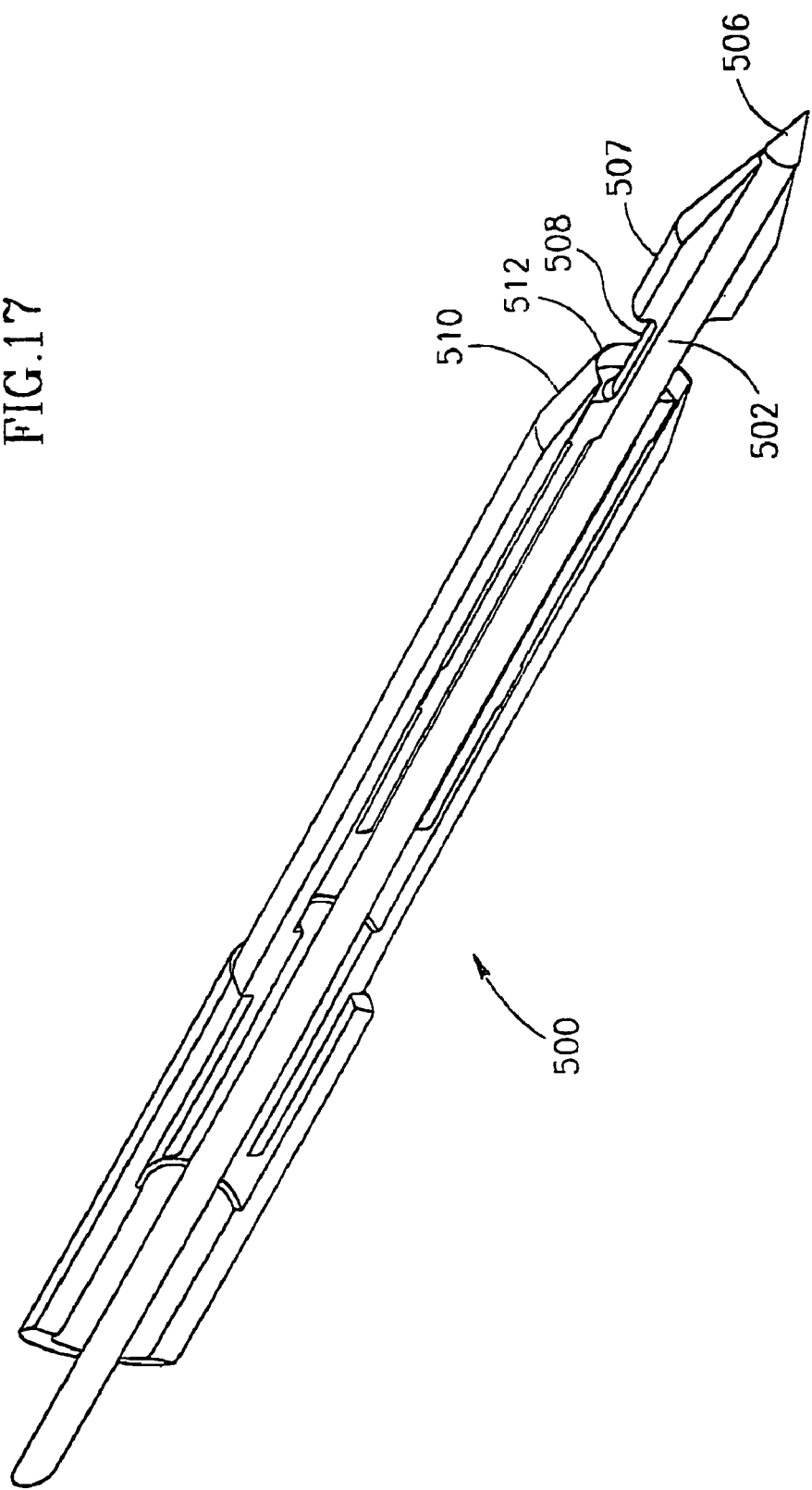
FIG. 17 is a cut-open perspective view of a tip retracting hole punch, in accordance with an alternative preferred embodiment of the invention.

FIG. 17 is a cut-open view of a tip retracting hole punch 500, in accordance with an alternative preferred embodiment of the invention. In this embodiment, the retracting of a tip 506 by a shaft 502 does not pull back a cylindrical portion 507 to cut vessel 422 against a cutting edge 512 of an anvil 510. The motion of tip 506 and of portion 507 may be separate and independent. Alternatively, the two motions may be caused by a single control. Alternatively, a peg or other means at the distal end of shaft 502 couples the motion of shaft 502 to the motion of cylinder 507 and/or anvil 510.

Oblique Hole Puncher

Figure 18:
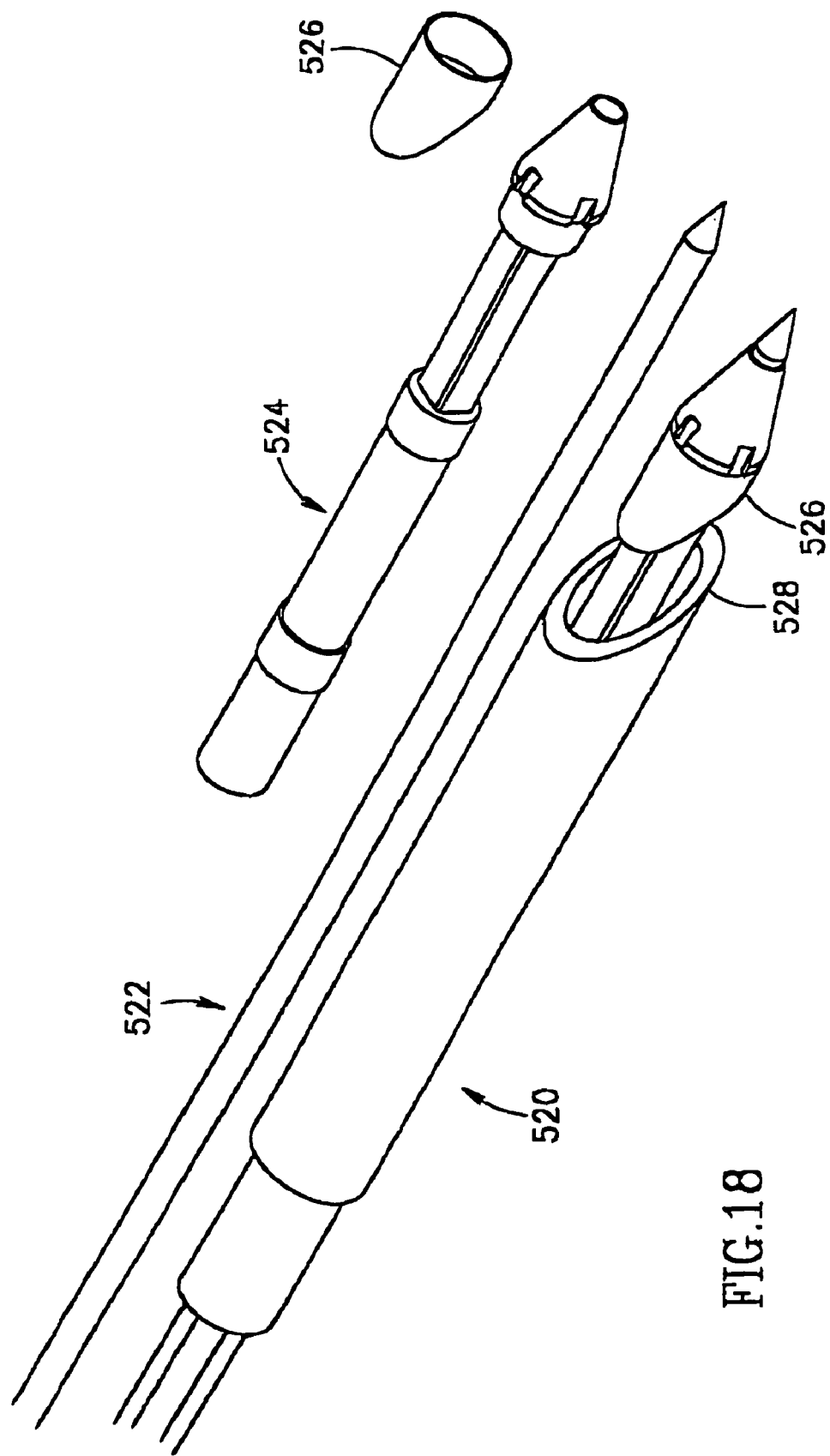
FIG. 18 shows an assembled and a disassembled oblique hole puncher, in accordance with a preferred embodiment of the invention.

FIG. 18 is a showing of an assembled and a taken apart oblique hole puncher 520, which can be used to make holes having a lumen that is not perpendicular to a blood vessel, in accordance with a preferred embodiment of the invention. The form of the hole may be circular, elliptical or other shaped, even polygonal, depending on the shape of the punch elements. Puncher 520 comprises generally of an outer tube 528 having a forward cutting edge, an inner element 524, a retracting tip 522 that fits inside inner element 524 and can be retracted, for example as described above, and a cutting piece 526, which is retracted by inner element 524 against the forward cutting edge, to punch a hole in vessel 422. The location of the cutting edges and the anvils can be varied in other embodiments. Additionally, retracting tip 522 is optional. In a preferred embodiment of the invention, the plane defined by cutting piece 526 is not parallel to the forward cutting edge, although it may be made parallel. Rather, an angular difference of between 5° and 15° and preferably about 5° is provided. For example, for a 45° punch, the forward cutting edge is 45° (on the back of inner element 524) and cutting piece 526 has an angle of 50°. The separation of cutting piece 526 from inner element 524 may allow lower cost machining of the cutting edge and puncturing tip. Alternatively or additionally, by replacing cutting edge 526, different angles of punching can be achieved.

Alternative Oblique Hole Puncher

Figure 19A:
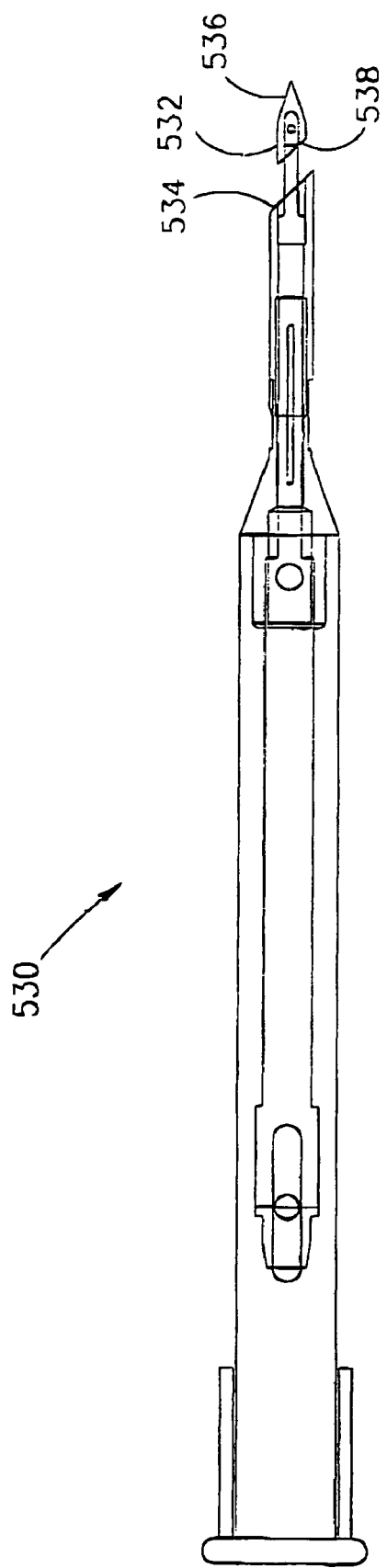
FIG. 19A is a schematic illustration of an alternative oblique hole puncher in accordance with another preferred embodiment of the invention.

FIG. 19A is a schematic illustration of an alternative oblique hole puncher 530 in accordance with another preferred embodiment of the invention. Puncher 530 utilizes a solid tip element 532 having a forward tip 536 and a back cutting face 538. A matching (optionally non-parallel) forward cutting face 534 is provided to cut vessel 422 between them.

Figure 19B:
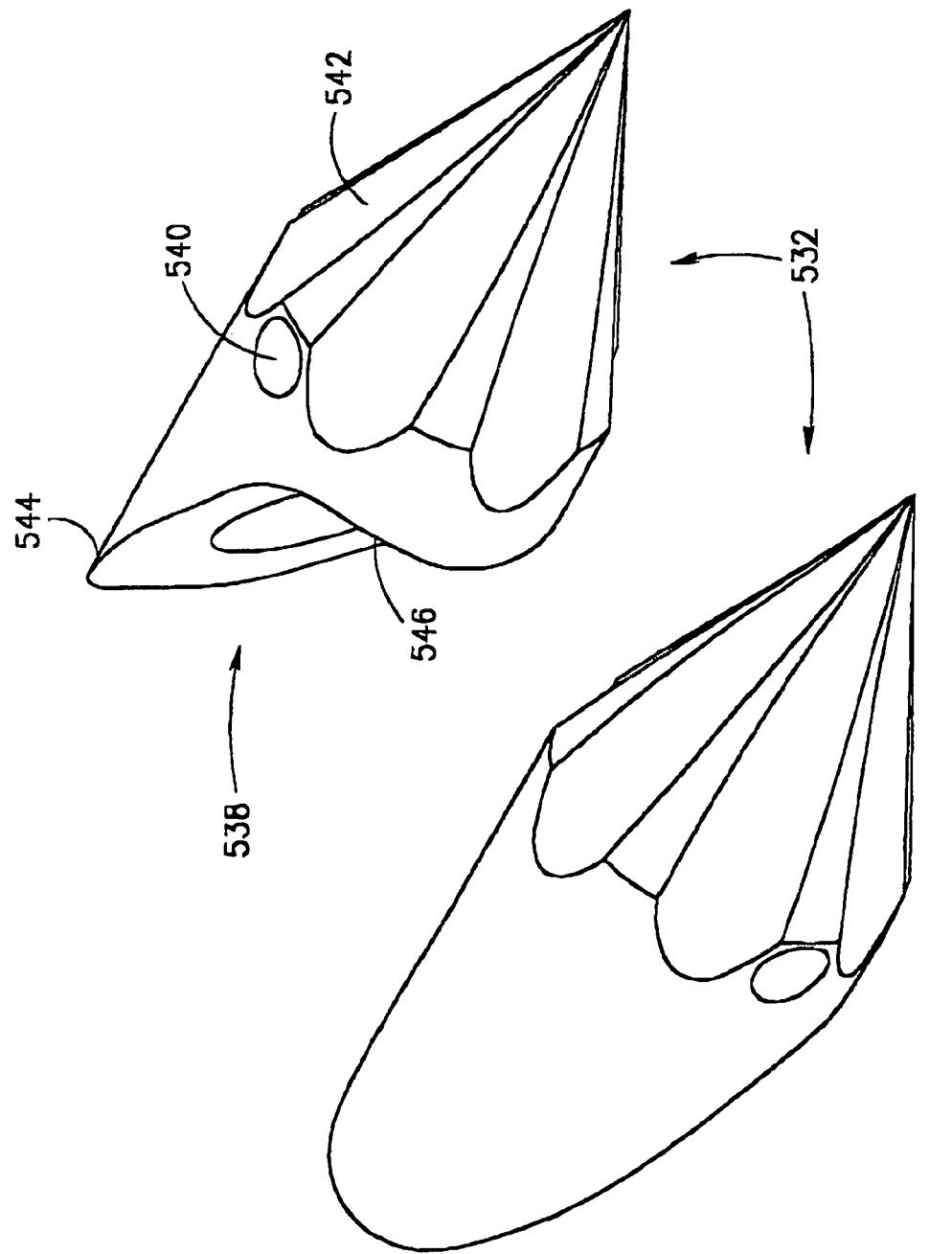
FIG. 19B shows two views of the tip of the puncher of FIG. 19A.

FIG. 19B is a showing of tip element 532, in two views. The embodiment shown here includes a plurality of groves 542 formed in the tip. These groves are not essential, however, they appear to reduce the need to rotate the tip while puncturing the blood vessel. An opening 540 for a pin to attach the tip to a shaft is also preferably provided. Back cutting face 538 preferably includes an inclined portion 544 and a relatively flat portion 546, to assist in holding the blood vessel.

Optionally, rotation of the tip of the puncher is provided by vibrating the tip and/or the rest of the puncher. Alternatively, the rotation may be provided manually.

Mounting the Connector on a Graft

Several methods are available for mounting the anastomosis device on the graft. In many of the embodiments described herein, the device is on the outside of the graft and the graft has an intima-to-intima connection with the blood vessel. Alternatively, in some of the other embodiments, most of the device is outside the graft and the anastomosis connection.

In a preferred embodiment of the invention, the graft is everted over the connector, such that the spikes extend from the graft and the rest of the connector is under or distal the everted portion of the graft. The eversion may be partial (e.g., about 90°) or complete (e.g., about 180°). However, other degrees of eversion can also be utilized. The eversion process itself is usually not easy, since the graft is slippery and small and resists manipulation. An additional problem is that the spikes may be hooked and not suitable for insertion through a graft without causing great damage.

Various solutions for eversion are described herein. In particular, three classes of solutions are generally presented:

(a) Manual (or machine assisted) eversion of the graft. The connector may transfix the graft before during or after the eversion.

(b) Transfixing of the graft by the connector, in which the actual eversion is effected by manipulation of the device and/or by performing the anastomosis.

(c) Avoiding performing an eversion altogether, possibly by simulating the eversion.

One Part Connector Mounter

FIGS. 20A–20D illustrates a transfixing-based eversion method (b), in accordance with a preferred embodiment of the invention. A benefit of the particular embodiment shown in FIGS. 20A–20D is that the eversion device is nearly completely outside the graft, so that one end of the graft may already be connected to the patient.

In FIG. 20A, a graft 551 is inserted inside a vessel holder 552. A connector 554 having a plurality of forward spikes 556 is mounted on a connector holder 564. One or more tip maintainers 562 are preferably provided to keep spikes 556 of connector 554 from bending back to their relaxed position (e.g., in super elastic or elastic devices). The end of graft 551 is engaged by a plurality of lips 560, which are coupled to an expander 558.

In FIG. 20B, expander 558 is expanded, thereby increasing its radius and causing lips 560 to stretch the opening of graft 551. It is noted that the inner radius of lips 560 is preferably the same or greater than the outer radius of spikes 556. Also, other mechanisms to cause lips 560 to increase their inner radius may be used.

In FIG. 20C connector 564 is advanced, thereby causing spikes 556 to transfix the end of graft 551.

In FIG. 20D, the end result is shown, in which a partial eversion is achieved. It is noted that spikes 556, once released from tip maintainers 562, bend. Optionally, lips 560 prevent bending of spikes 556 back into graft 551. The various expanders and tip holders may now be removed.

In an alternative embodiment, the spikes are inserted at an angle to the wall of the graft, thereby providing a partial inversion of the graft and/or maintaining the graft in the configuration caused by the spreading apart of the graft end.

Two Part Graft Everter

FIGS. 21A–21E illustrate a graft everter 570, in accordance with a preferred embodiment of the invention. Graft 551 is inserted in a graft holder 564 possibly having mounted thereon an anastomosis connector) and only its tip protrudes. Holder 564 may be held in one hand and everter 570 in another hand. Alternatively, one or both may be bench mounted and/or coupled to each other. Connector 554 (not shown) may be mounted on holder 564.

Everter 570 comprises a main body 571, including a switch 580 and a head 572.

A detail of head 572 is shown in FIG. 21B. A tip 574, preferably rounded, is provided such that the end of graft 551 can be mounted on it. An expander 579, having a plurality of fingers 578 is used to expand the graft tip, as described below. A plurality of stop-fingers 576 is preferably provided to control the advance of graft 551 over tip 574 and fingers 578. Optionally, but not necessarily, the relative location of stop-fingers 576 and tip 574 can be controlled, for example to control the amount of eversion or to allow a more stable hold on the graft.

FIG. 21C is a detail of expander 579.

Figure 21D:
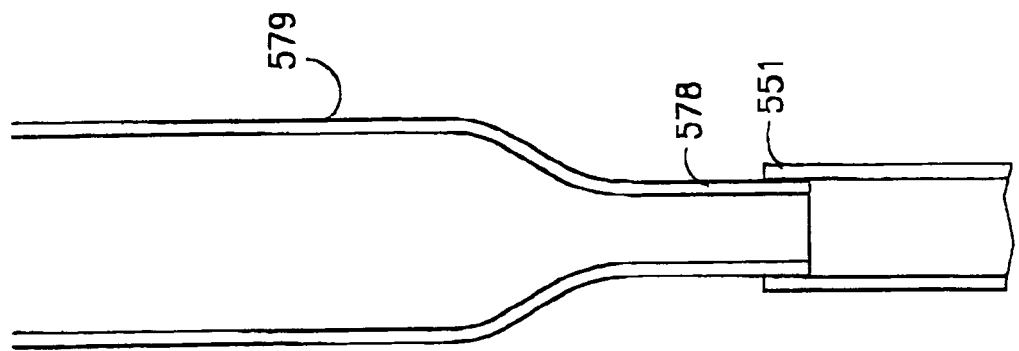

FIG. 21D is a side section through expander 579 showing graft 551 mounted on it.

Figure 21E:
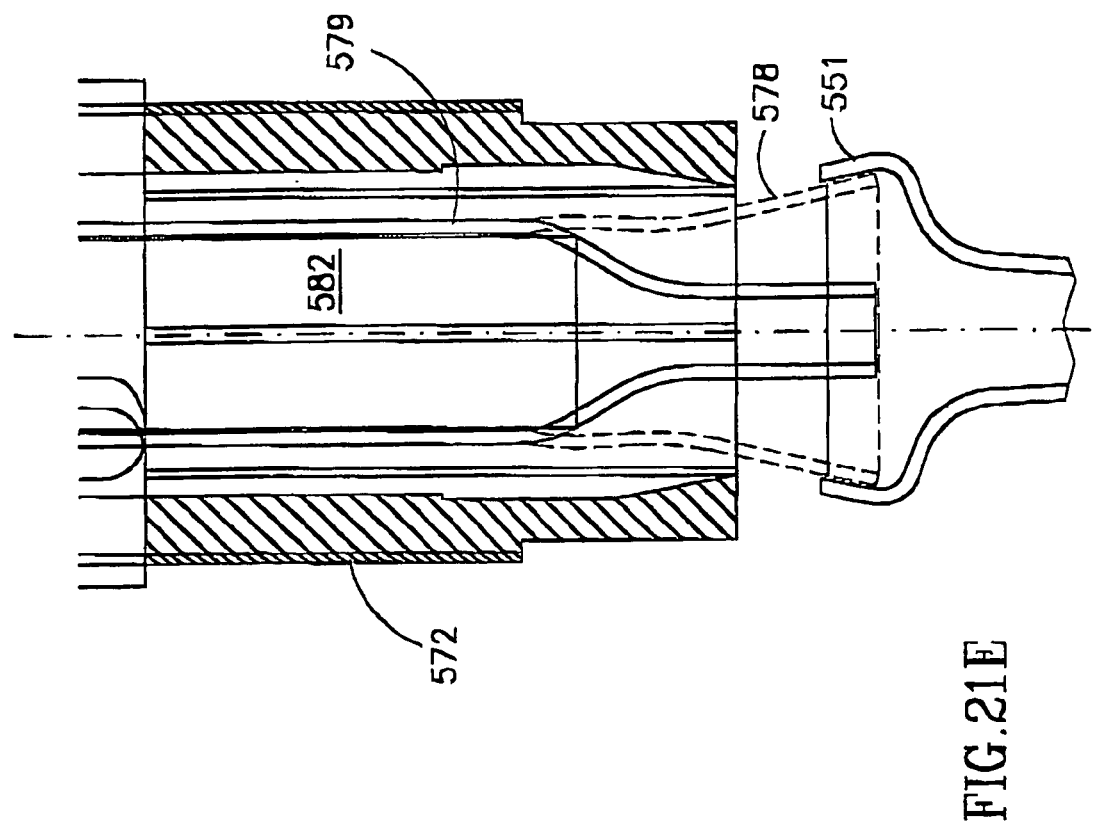

In FIG. 21E, a pin 582 is advanced, causing expander 579 to expand. The vessel is everted by advancing graft holder 564 with graft 551, so that it is inside fingers 578. Possibly, the advancing the graft 551 includes advancing of the anastomosis connector, thereby transfixing the graft. The extent of advancing may be controlled, if required, for example, by the resistance of the graft or by stop-fingers 576. When pin 582 is retracted, fingers 578 move inward and the eversion is complete. Alternatively, pin 582 also advances the tube enclosing expander 579. This tube also serves as a stop to further expansion of fingers 578, trapping the graft between the fingers and the tube. When the tube is advanced, it everts the graft off of fingers 758.

In an alternative embodiment, stop-fingers 579 include small spikes at their tips and are also expanded by pin 582, thus engaging the graft from the inside. A further advance of pin 582 causes the stop-fingers (now everting fingers) to evert the graft off of fingers 578. This motion mimics the manual process of everting using a forceps, except that the graft is only engaged from the inside. Alternatively, the graft is engaged both from inside and from outside.

Alternative Two Part Graft Everter

Figure 22:
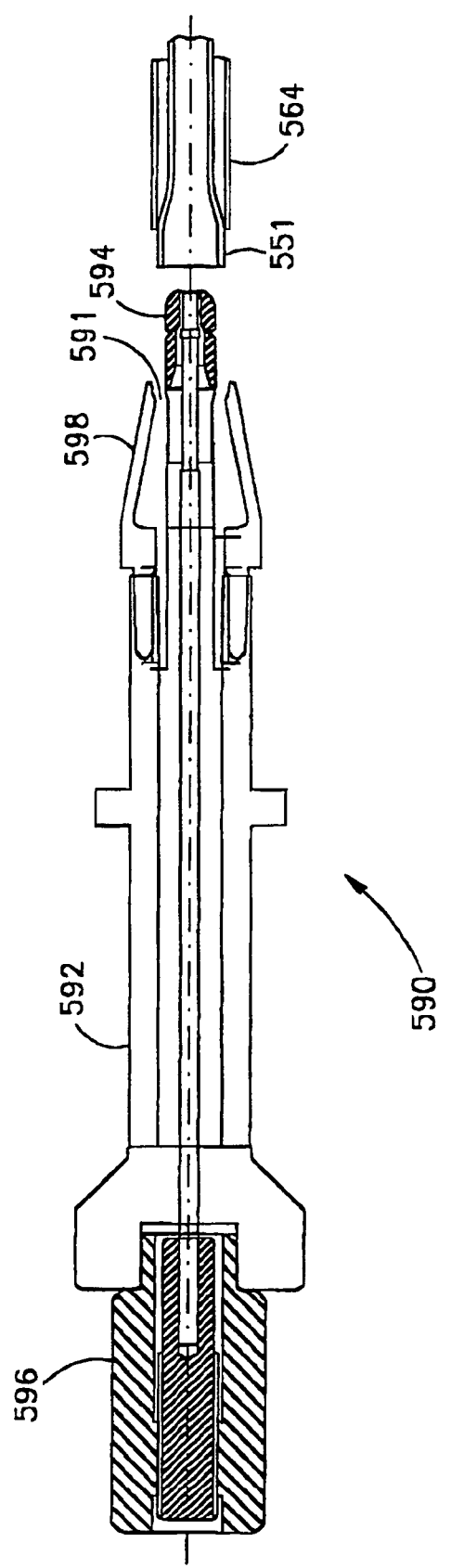
FIG. 22 is a schematic cut-through illustration of an alternative graft everter, in accordance with a preferred embodiment of the invention.

FIG. 22 is a schematic cut-through illustration of an alternative graft everter 590, in accordance with a preferred embodiment of the invention. In everter 590, the graft is engaged by the everter, additionally or alternatively to engaging only the graft tip (as in the embodiment of FIGS. 21A–21E). An expanding tip 594, preferably mounted at the end of a body 592, preferably grasps graft 551 from the inside. Graft 551 may or may not be mounted inside a graft holder 564. Preferably, tip 594 is an expanding silicone tip, which is expanded by a pressure source 596. An exemplary pressure source comprises a rod, which when pressed into a silicon tip 594, it causes it to deform. Alternatively, other expanding or grasping mechanisms may be used.

A plurality of fingers (or a complete ring) 598 is provided, with an engaging edge 591. When a finger 598 is advanced, engaging edge 591 pushes the rim of graft 551 back, thereby everting the graft. The eversion may be by a single advance of the fingers. Alternatively, each such advance rolls the graft back an additional small amount.

Spike Tip Control

In some embodiments of the invention, the spikes of the connector which transfix the everted vessel are in a bent state during the transfixing. However, in some preferred embodiments of the invention, the spikes are bent after the transfixing.

Since the graft need not be living material or even in the body (or at least not in contact with body structures) at the time of transfixing, shape memory materials, such as those that bend when heated, may be used. The heating may be for example, in ambient air of a room or by passing an electric current through the connector. Preferably, only the tip of the spike is shape memory, so that the rest of the spike is rigid enough to be inserted through the graft.

Alternatively, a shield, for example a tube with one finger for each spike, is provided over the connector while it is advanced, to maintain the spike tips in a straight configuration.

Alternatively or additionally, the spikes may be bent after they transfix, for example by plastic deformation. Possibly the spike is heat-treated at the bend point, after transfixing the graft, to "learn" the new configuration.

Twisting Based Transfixing

Figure 23A:
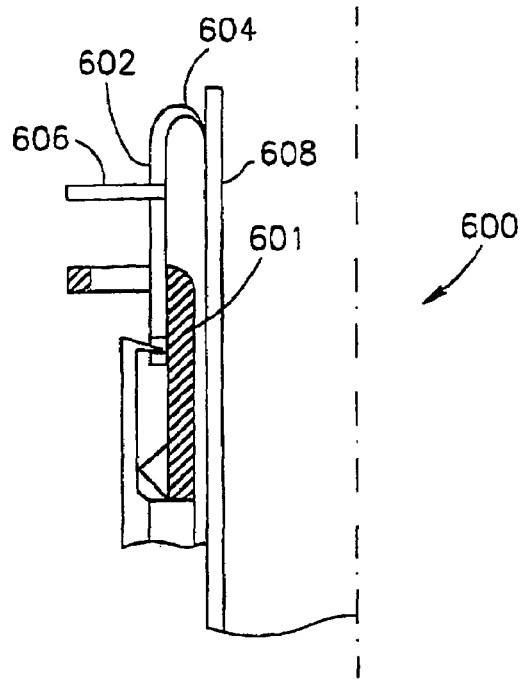
FIGS. 23A–23G illustrate a method of transfixing a blood vessel by twisting spikes of a connector, in accordance with a preferred embodiment of the invention.

FIGS. 23A–23G illustrate a method of transfixing a blood vessel by twisting spikes of a connector, in accordance with a preferred embodiment of the invention. FIG. 23A shows a connector 600 that can be similar to the connector of FIG. 2, except that spikes 602 (only one shown) are bent so that tips 604 (only one shown) point in, rather than out. Connector 600 preferably comprises a spike section 601 and a tubular section 603.

A sleeve 608 is preferably provided to protect an inserted graft 551 (FIG. 23B) from accidentally transfixing on tip 604. In a preferred embodiment of the invention, the resting configuration of tips 604 is out and they are twisted in and maintained in this position by a twist maintainer 606. However, this is not essential. For example, spikes 602 may be plastically twisted after graft 551 is transfixed. It should be noted that plastic deformation is possible also in super elastic devices, for example by over-rotation.

Figure 23B:
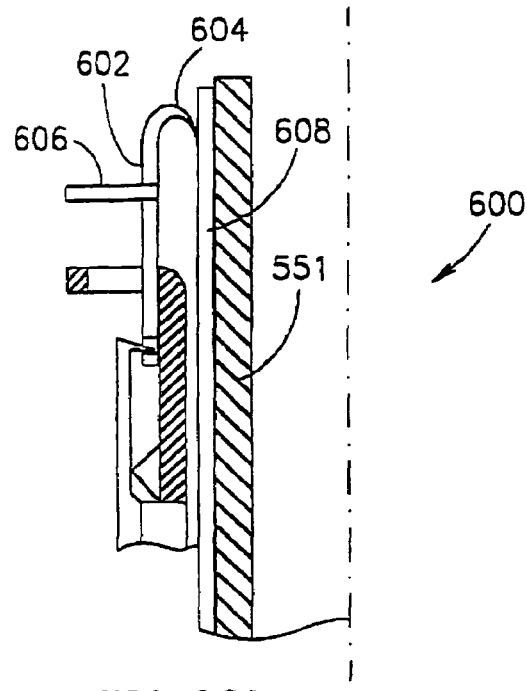

In FIG. 23B, graft 551 is inserted into the graft holder, under sleeve 608.

Figure 23C:
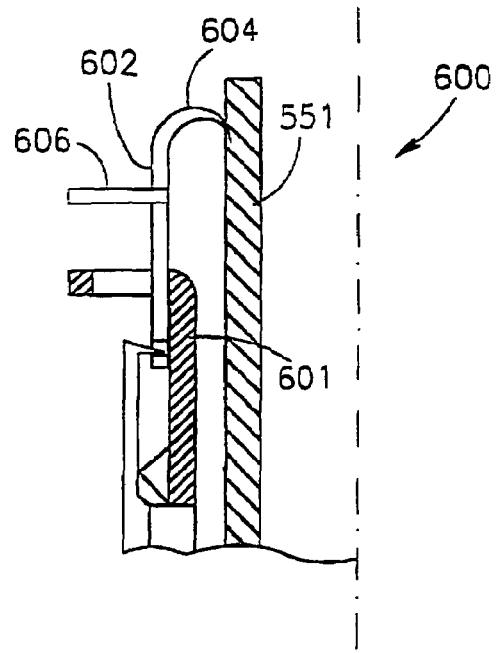

In FIG. 23C, sleeve 608 is removed, allowing contact between graft 551 and tips 604.

Figure 23D:
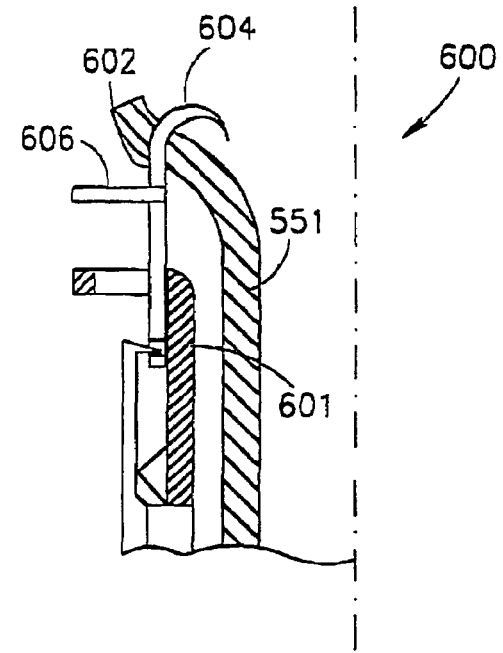

In FIG. 23D, graft 551 is transfixed by tips 604. In one method, graft 551 is pulled forward out of the graft holder and/or stretched, for example using a device such as shown in FIG. 21. In another example, connector 600 is retracted, possibly while inflating a balloon or other expandable element inside graft 551, to prevent its motion and/or control the transfixing.

Figure 23E:
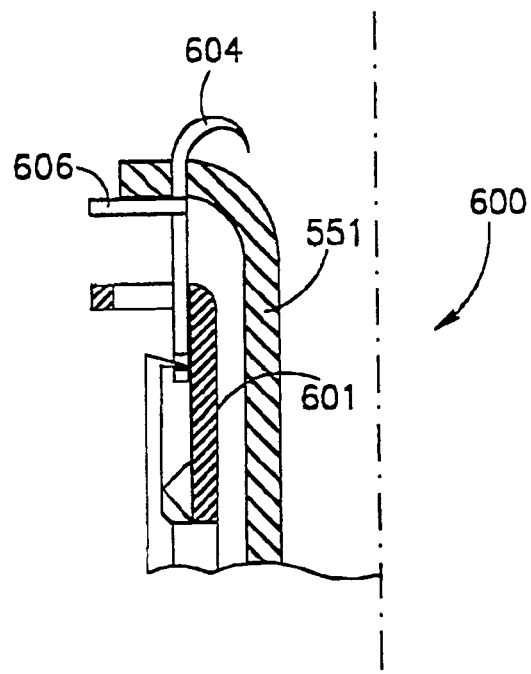

In FIG. 23E, an optional step of advancing the spike relative to the everted portion of graft 551 is shown. This step may also be performed later, or may be omitted.

Figure 23F:
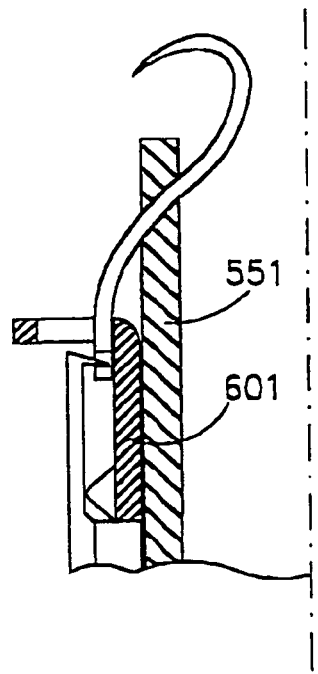

In FIG. 23F, twist maintainer 606 is removed (or the spikes twisted) so that the spikes twist and tips 604 point out.

Figure 23G:
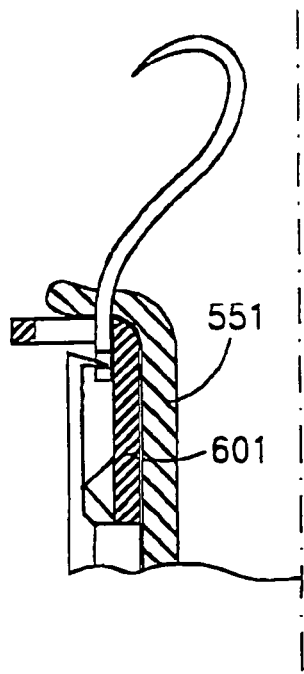

FIG. 23G shows the completed transfixing process, after an optional step of retracting the graft over the spikes.

It should be noted that rotation of spikes to achieve an easier transfixing and/or eversion may also be practiced in staple embodiments, where the anastomosis is performed using a plurality of individual staples, each of which can be rotated around its long axis, similarly to the twist of spike 602 as shown.

Simulated Eversion

Mammary arteries, in general, are relatively thick and difficult to evert. Applicants have discovered, surprisingly, that the mammary artery can be manipulated to have an effective everted area, without actually everting the artery and while applying a relatively low amount of stress to the artery.

FIGS. 24A–24D illustrate a method of simulating an eversion, especially for a mammary artery, in accordance with a preferred embodiment of the invention.

Figure 24A:
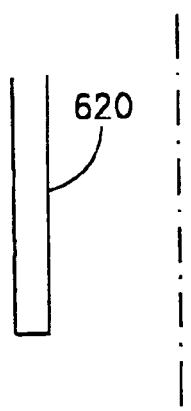
FIGS. 24A–24E illustrate a method of simulating an eversion, especially for a mammary artery, in accordance with a preferred embodiment of the invention

FIG. 24A shows one wall of a mammary artery 620. It is noted that other types of blood vessels and graft materials may be used instead.

Figure 24B:
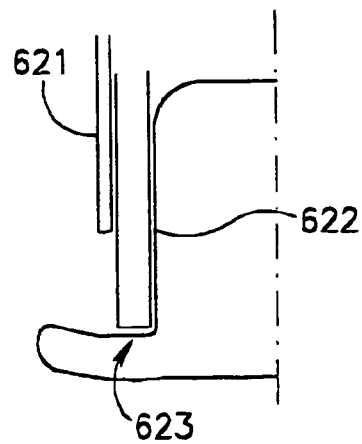

In FIG. 24B, an internal mold 622 and a vessel engaging external framework 621 are provided, to engage artery 620. The engaging means may be any known in the art, for example a friction surface or small barbs.

Figure 24C:
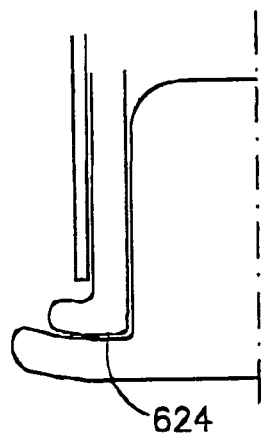

In FIG. 24C, framework 621 is advanced so that the end of artery 220 is pushed against a shaping portion 623 of mold 622 and widens. By suitable selection of the geometry of mold 622, shaping portion 623 and external framework 621, the size and type of distortion can be controlled.

Optionally, framework 621 and/or mold 622 are ridged, to cause a ripple in artery 620. Although a perpendicular mold is shown, an oblique mold or a mold that otherwise shapes the end of artery 620, for example into a saddle shape, may be used.

Figure 24D:
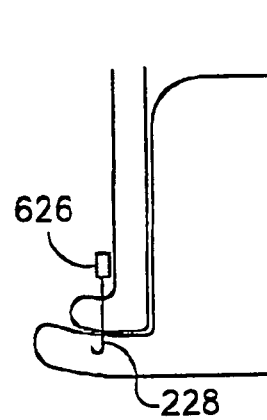

In FIG. 24D, the thickened part of artery 620 is transfixed by a spike 228 of a connector 626, for example using methods described herein. Mold 622 may include apertures so that it does not damage spike 228.

In an exemplary embodiment, a LIMA is compressed as much as 1 cm. It should be noted that the end location of the intima and the adventizia of artery 620 can also be controlled by mold 622 and framework 621.

Figure 24E:
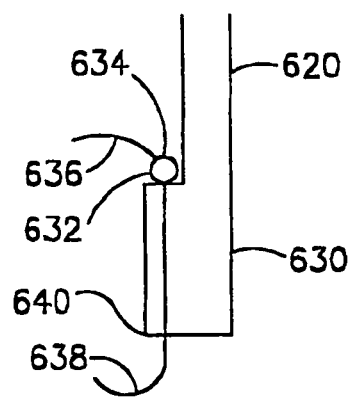

FIG. 24E illustrates an alternative embodiment in which a connector 632, for example an aortic connector transfixes a thickened portion 630 of artery 620. A ring portion 634 is outside the thickening. By proper shaping of mold 622, there can be a portion of intima also at a location 640 outside the thickening 630, allowing an intima-to-intima connection. Possibly, dissection of artery 620 and maintaining thickening 630 is by the transfixing by a forward spike 638 of connector 632.

In an alternative embodiment of the invention, a blood vessel or graft is shaped by compressing it to have thickenings (not only at its end) and inserting one or more spikes or a connector through the thickening, to maintain the shaping effect.

Inserting the Connector

Once the graft is everted and transfixed by the connector, the connector and graft are to be attached to target vessel 422, in the punched hole. Once the connection is completed, the tools must be removed from the graft.

Figure 25A:
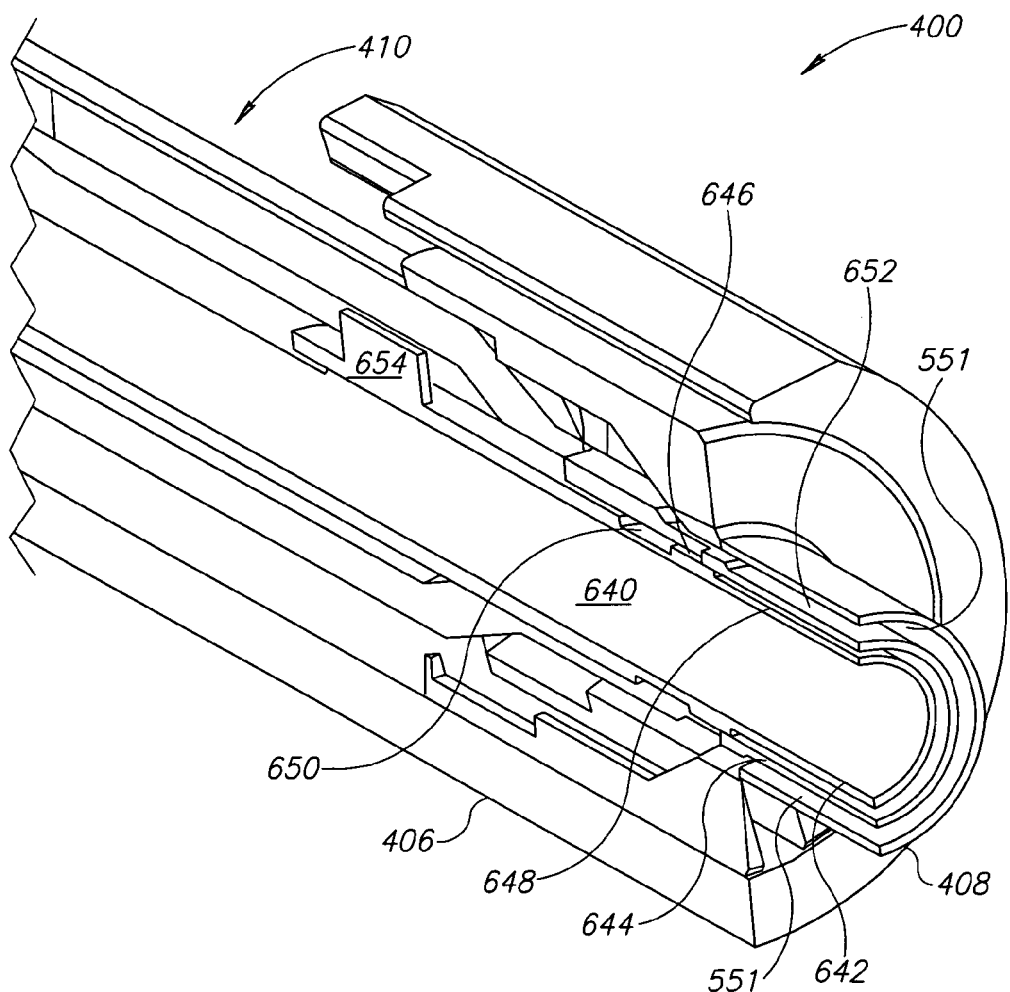
FIG. 25A is a close-up of the scaffold tool of FIG. 11 when a combination graft holder and connector holder is inserted therein, in accordance with a preferred embodiment of the invention.
Figure 25B:
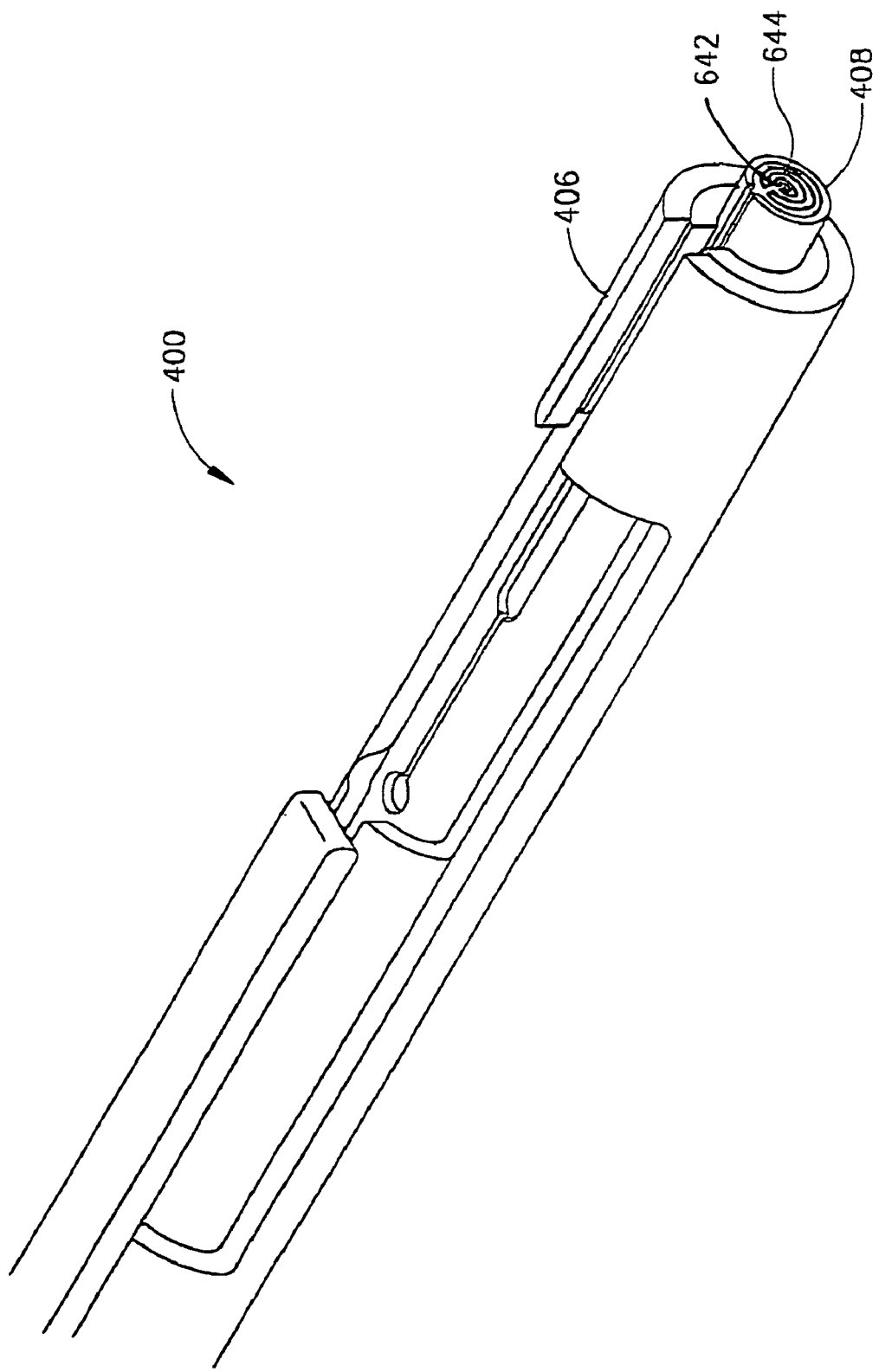
FIG. 25B is a perspective view of FIG. 25A.

FIG. 25A is a cut-through close-up of scaffold tool 400 when a combination graft holder and connector holder 640 is inserted therein, showing graft 551 schematically, but not showing a connector. FIG. 25B is a perspective view of FIG. 25A. Holder 640 preferably comprises two layers, an inner layer 642, which preferably holds a connector (not shown) on its surface and an outer layer 644 which assists in inserting the device into the aorta (or other target vessel) and protects the everted part of graft 551. Alternatively or additionally, layer 644 maintains the straight configuration of the spikes. The everted part of graft 551 is preferably between layer 644 and tip 408, however, it may also be between layers 642 and 644.

Layer 642 preferably includes protrusions to grasp the connector by thickening on it (FIG. 7). For example, the tines of the spikes of FIG. 7 can be located in an area 650 of the layer, while the body of the connector is in an area 640 of the layer. A ring of protrusion 646 prevent motion of the connector. A similar configuration can be used to hold a two part device, such as described in FIG. 2. In such a case, layer 642 may include notches at its tips to allow the bent spikes to be bent inwards.

A knife blade 654 is preferably provided to rip apart layer 644, as described below in more detail.

In operation, either tip 408 is retracted or layers 642 and 644 advanced, so that the target vessel is in contact with an area 652 on the outside of layer 644.

Layer 644 is retracted, such that the forward spikes of the connector can bend. Scaffold 400 (or layer 642) is then preferably retracted so that the bent spikes engage target vessel 422 (not shown).

Figure 26:
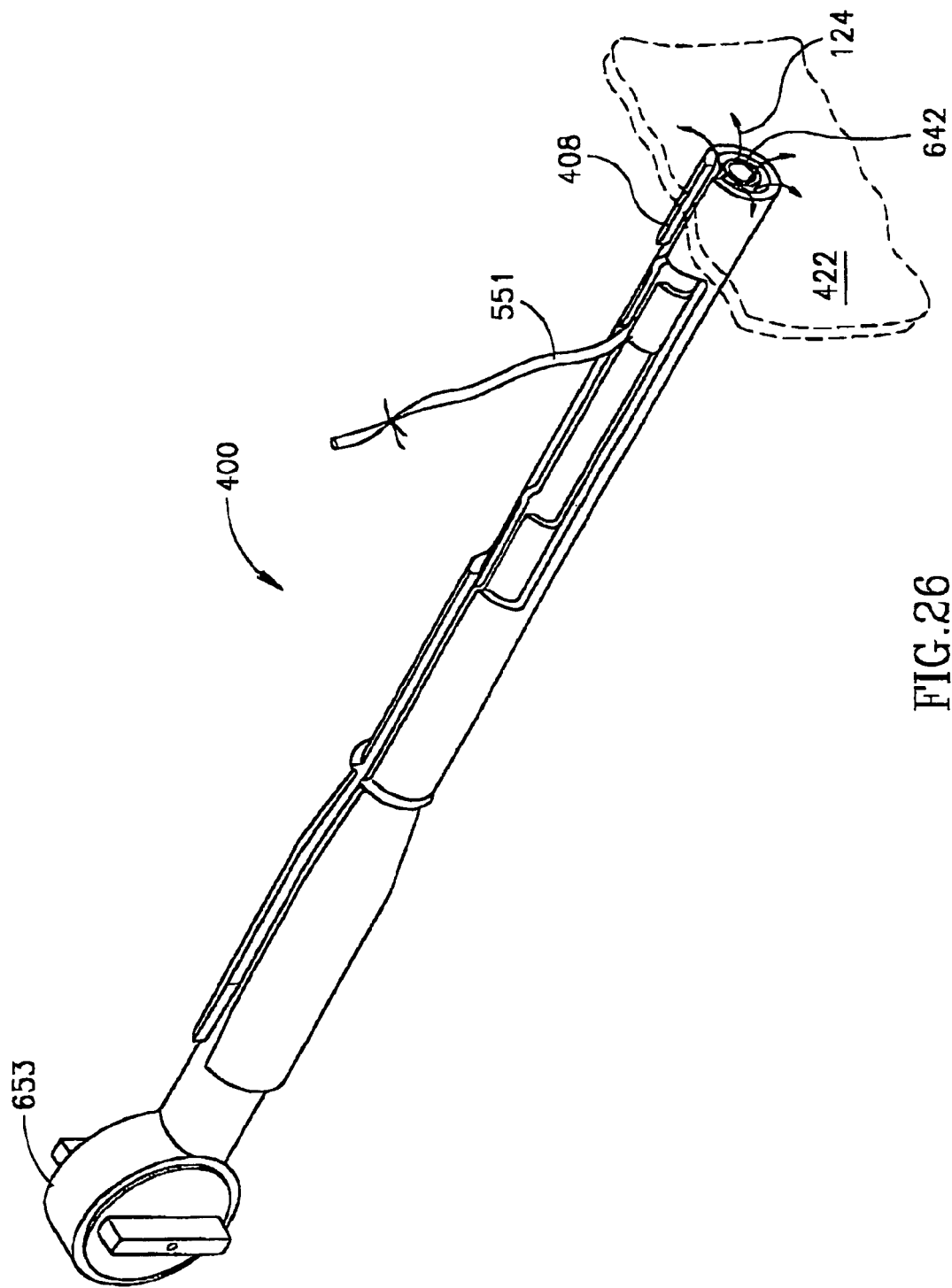
FIG. 26 shows the situation after a tip the scaffold of FIG. 11 is retracted, showing spikes that engage the target vessel.

FIG. 26 shows the situation after tip 408 is retracted, showing spikes 124 that engage target vessel 422.

Further retraction of layer 644 releases the radial constraint on the back spikes of the connector, allowing then to bend out of area 650 (FIG. 25A) and close on vessel 422. At this point also layer 642 can be retracted from the anastomosis.

In a preferred embodiment of the invention, the relative movement of the various layers and tubes is provided by a mechanism in the handle of the tool, preferably operated by a simple control, such as knob 653.

Loading the Connector on the Delivery System

The connector may be mounted between layers 642 and 644, for example, by placing the relaxed graft on layer 642 and then bending back the back spikes so that they can be covered with layer 644. The bending back may be, for example using a forceps or using a dedicated tool.

Alternatively or additionally, the connector is cooled, for example using liquid Nitrogen, so that it becomes pliable.

Alternatively, the connector may be mounted in the following manner.

(a) The connector, in its relaxed state is mounted on a mandrel;

(b) A notched over tube is brought over the mandrel, so that the notch engages one of the back spikes of the connector.

(c) The notched tube is rotated, causing the engaged spike to be captured between the over tube and the mandrel, in a substantially straight configuration.

(d) Step (c) is repeated for all the spikes.

(e) Layer 644 is brought over the mandrel and the notched tube.

(f) The connector and mandrel are pulled through a notched cone. The notches are aligned so that the forward spikes are not affected by the cone. The body of the connector, on the other hand, is compressed by the cone, so that it fits inside outer layer 644, which is advanced to cover the body of the connector.

(g) The mandrel is removed and replaced with layer 642. Alternatively, the mandrel is layer 642.

Removing the Tools

When tip 408 and layer 644 are retracted, they are preferably slit by knife 654 of layer 642. Thus, they can be removed by retraction without damaging graft 551. Alternatively, the layers may be pre-split and removed using a peg or cone which splits tip 408 and/or layer 644. Although knife 654 is shown somewhat distal from the end of the device, it can be closer.

Figure 27:
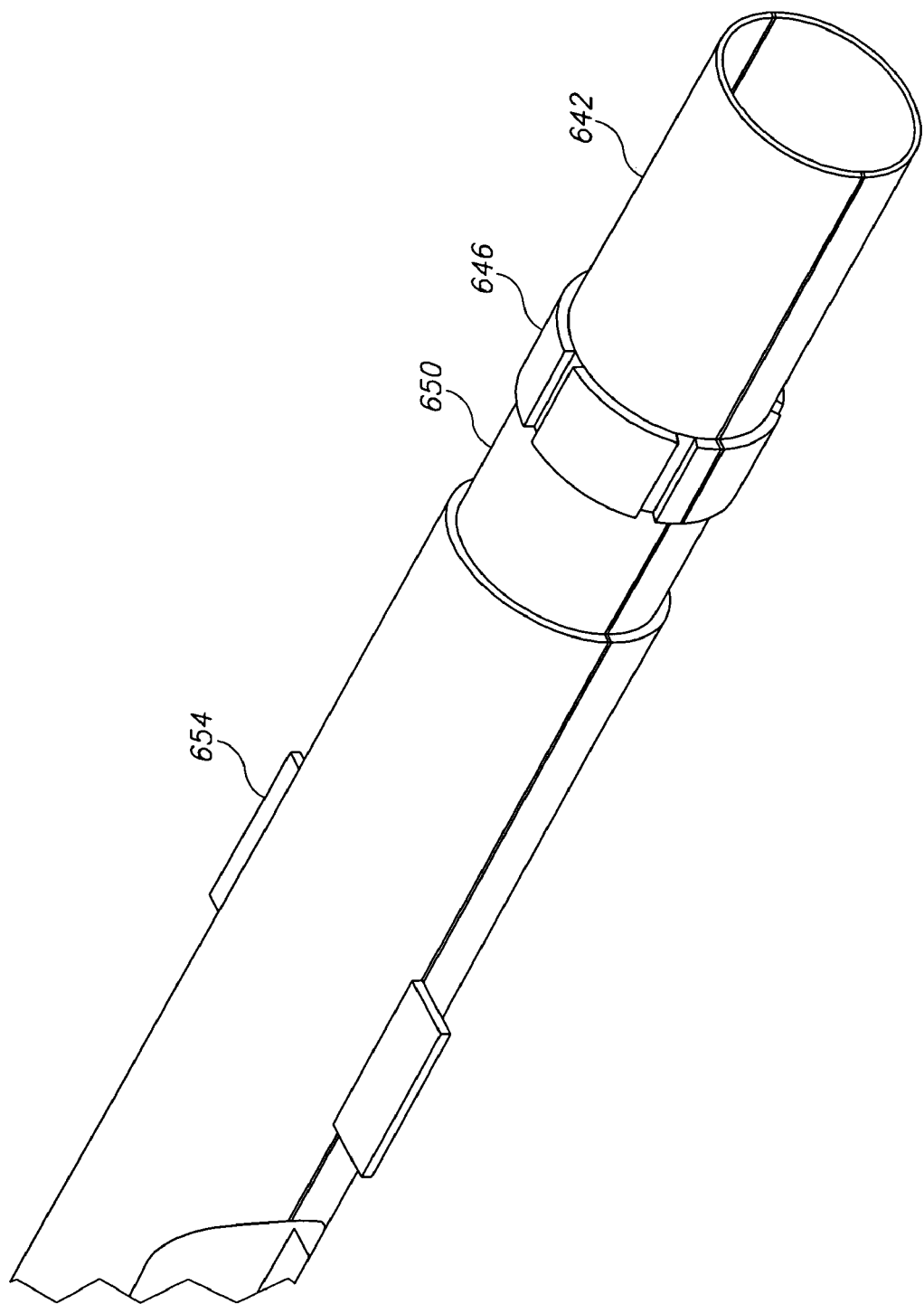
FIG. 27 shows only one layer of the combination of FIG. 25A, emphasizing a pre-formed slit in the layer, a knife and protrusions.

FIG. 27 shows only layer 642, emphasizing a pre-formed slit in the layer, knife 654 and protrusions 646.

Figure 28:
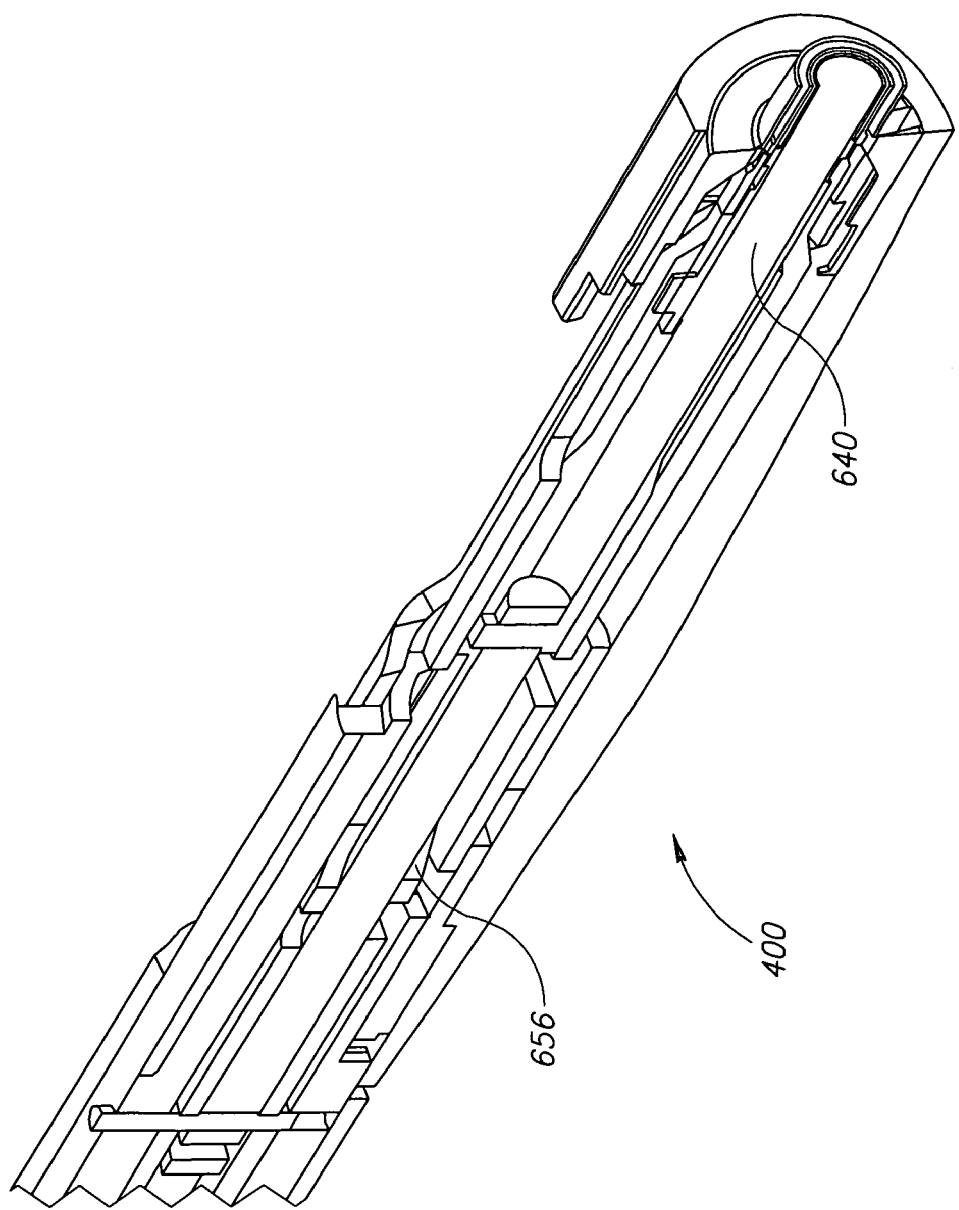
FIG. 28 is a cut-through view of the scaffold of FIG. 11, showing a peg or a cone which splits apart the layer of FIG. 27 when the layer is retracted sufficiently.

FIG. 28 is a cut-through view of tools 400 and 640, showing a peg or a cone 656 which splits apart layer 642 when layer 642 is retracted sufficiently. In alternative embodiments, peg 656 may be closer to the tip of scaffold 400 and/or it may be movable into position, when required.

Alternative Splitting Method

FIGS. 29A–29F illustrate an alternative connector delivery system 700 having an outside 703 and a distal end 711, in accordance with a preferred embodiment of the invention. System 700 also includes a body 701 and a handle 702.

Figure 29A:
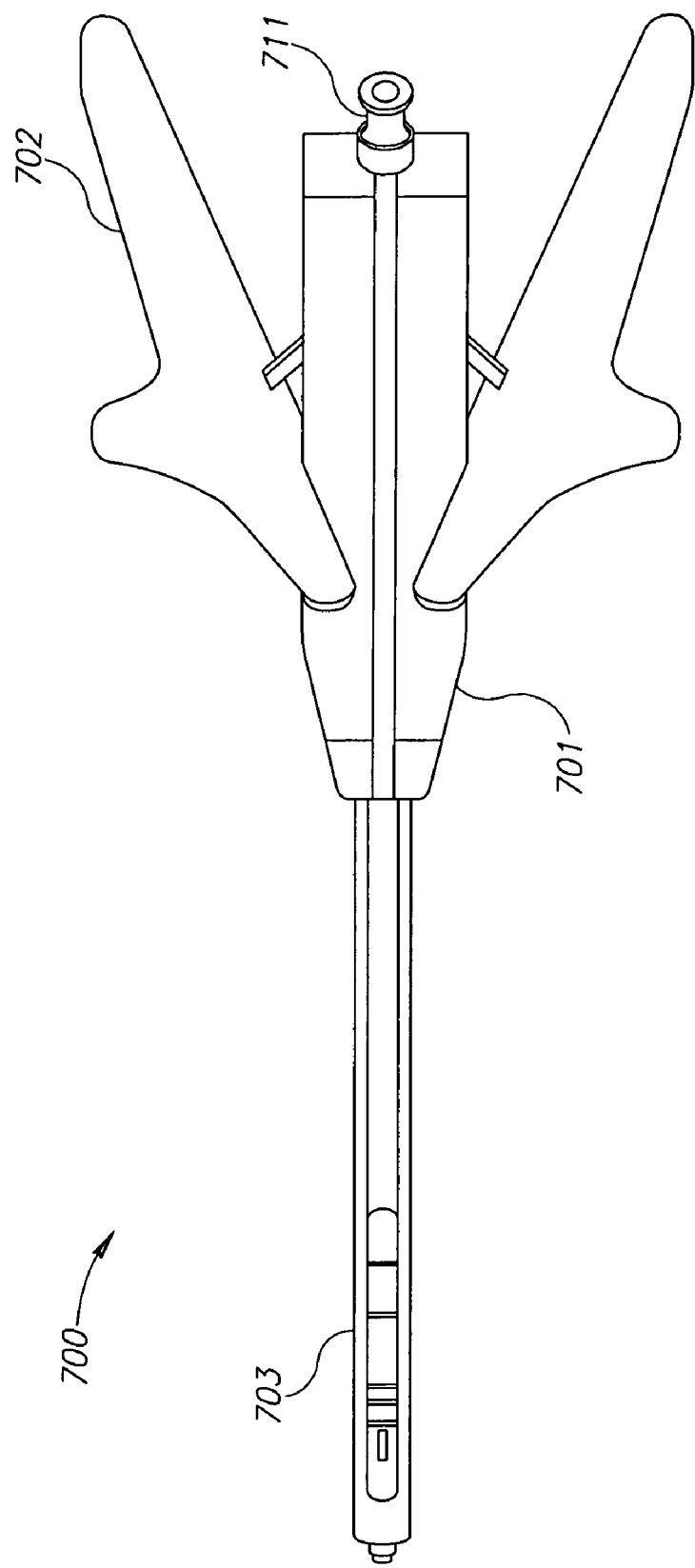
FIGS. 29A–29F illustrate an alternative connector delivery system using a peg-based splitting mechanism, in accordance with a preferred embodiment of the invention.
Figure 29B:
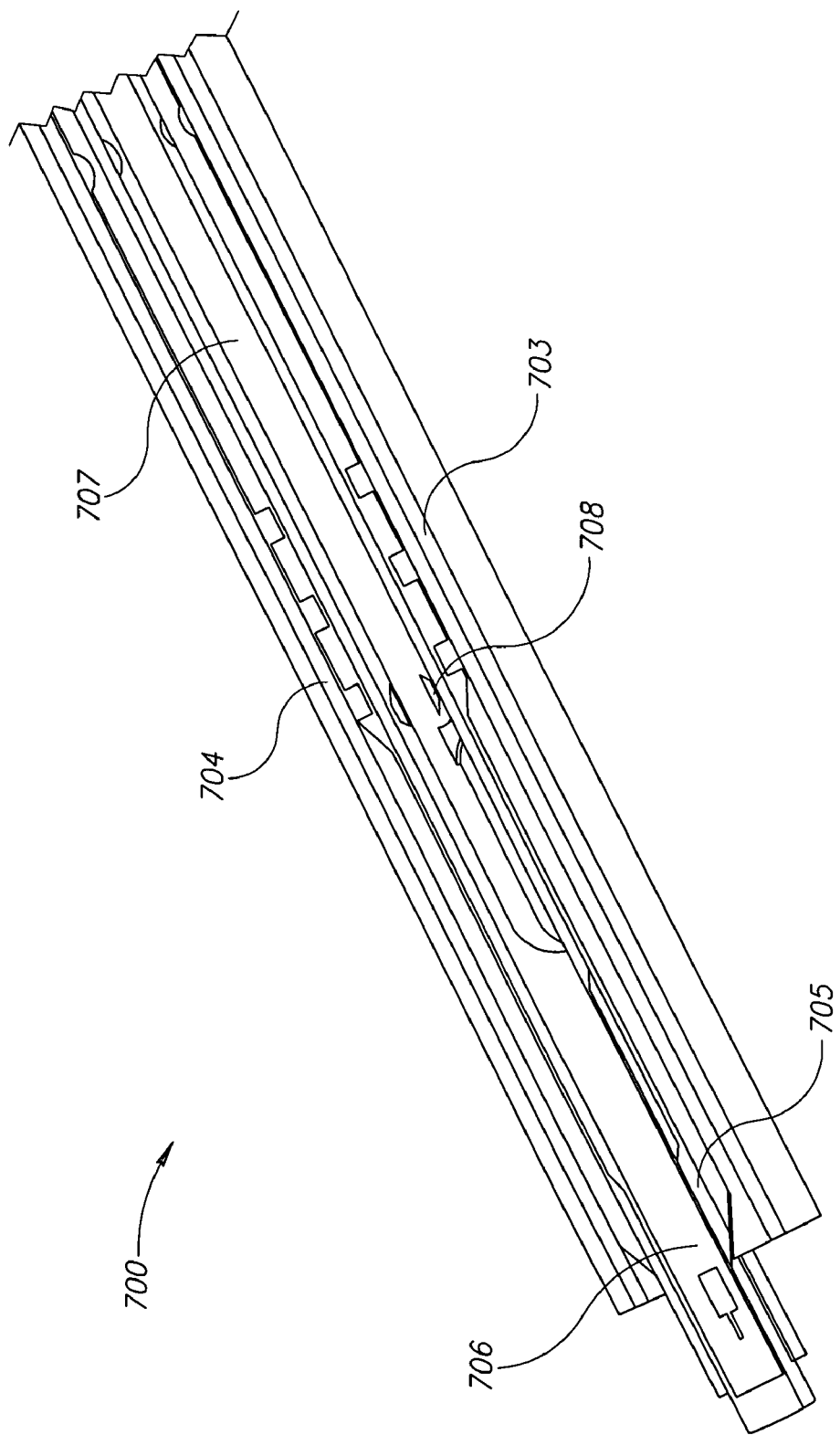

FIG. 29B is a cut-through view showing a magazine 705, a connector holder 706 and a splitting pin 708 attached to a rod 707. When rod 707 is retracted, pin 708 splits apart the layers it is in contact with, for example holder 706 and magazine 705. Alternatively or additionally, a retracting knife may be used.

Figure 29C:
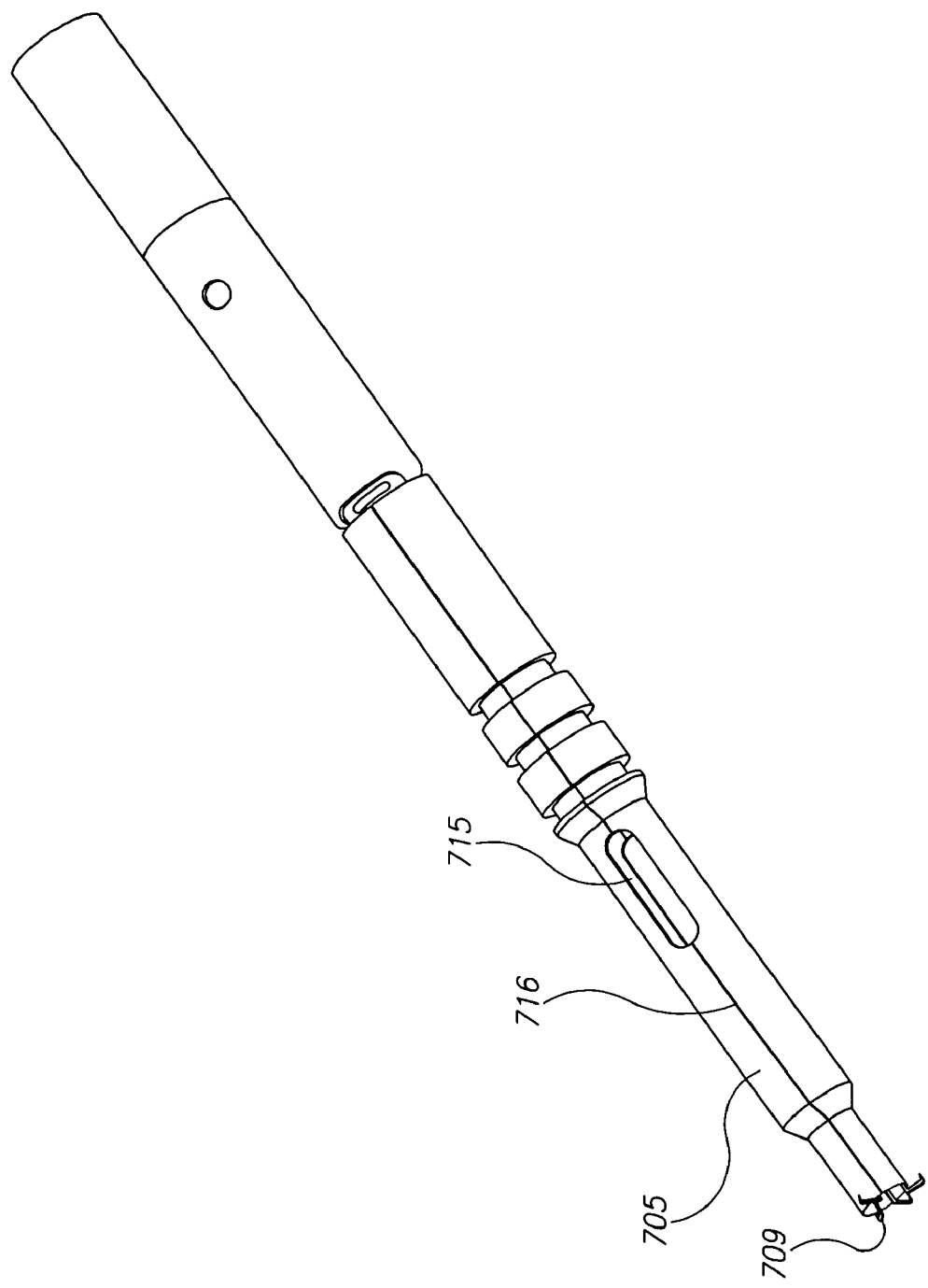

FIG. 29C shows only magazine 705 with a connector 709 poking out at its tip. A hollow 715 and a slit 716 for peg 708 to operate are shown as well.

Figure 29D:
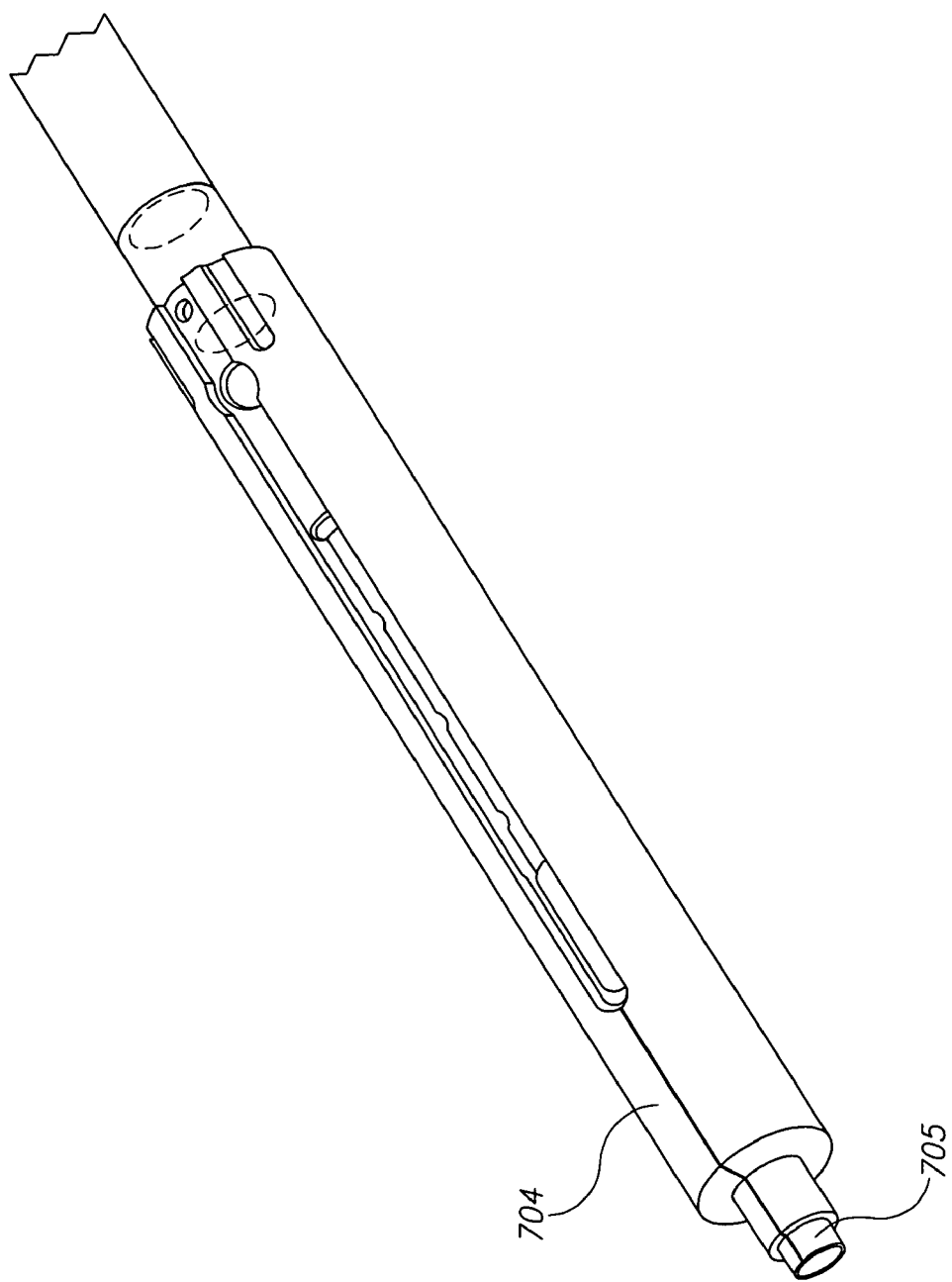

FIG. 29D shows an over-tube 704, used to seal the hole in the target vessel after the hole is punched in it. Again, a slot and a slit for peg 708 to operate are shown. Outside 703 preferably engages over-tube 704 snugly enough to prevent blood leakage through the slit. Alternatively or additionally, the slit area may comprise clot enhancing material. Alternatively or additionally, the slit area may be coated with a flexible material, such as rubber.

Figure 29E:
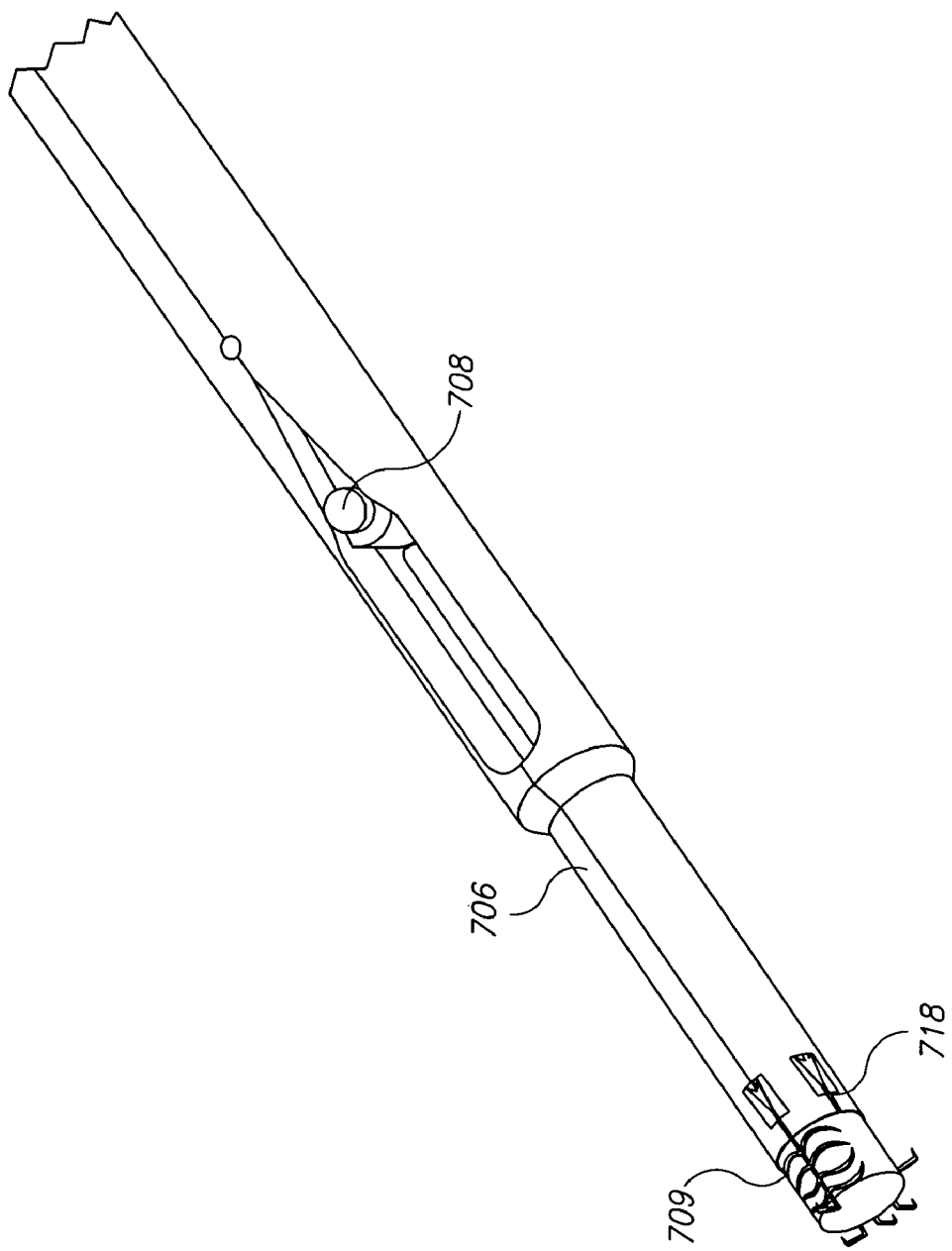

FIG. 29E illustrates device holder 706 and device 709, illustrating a slit and a slot in holder 706 and illustrating an protrusion based connector engaging element 718.

Figure 29F:
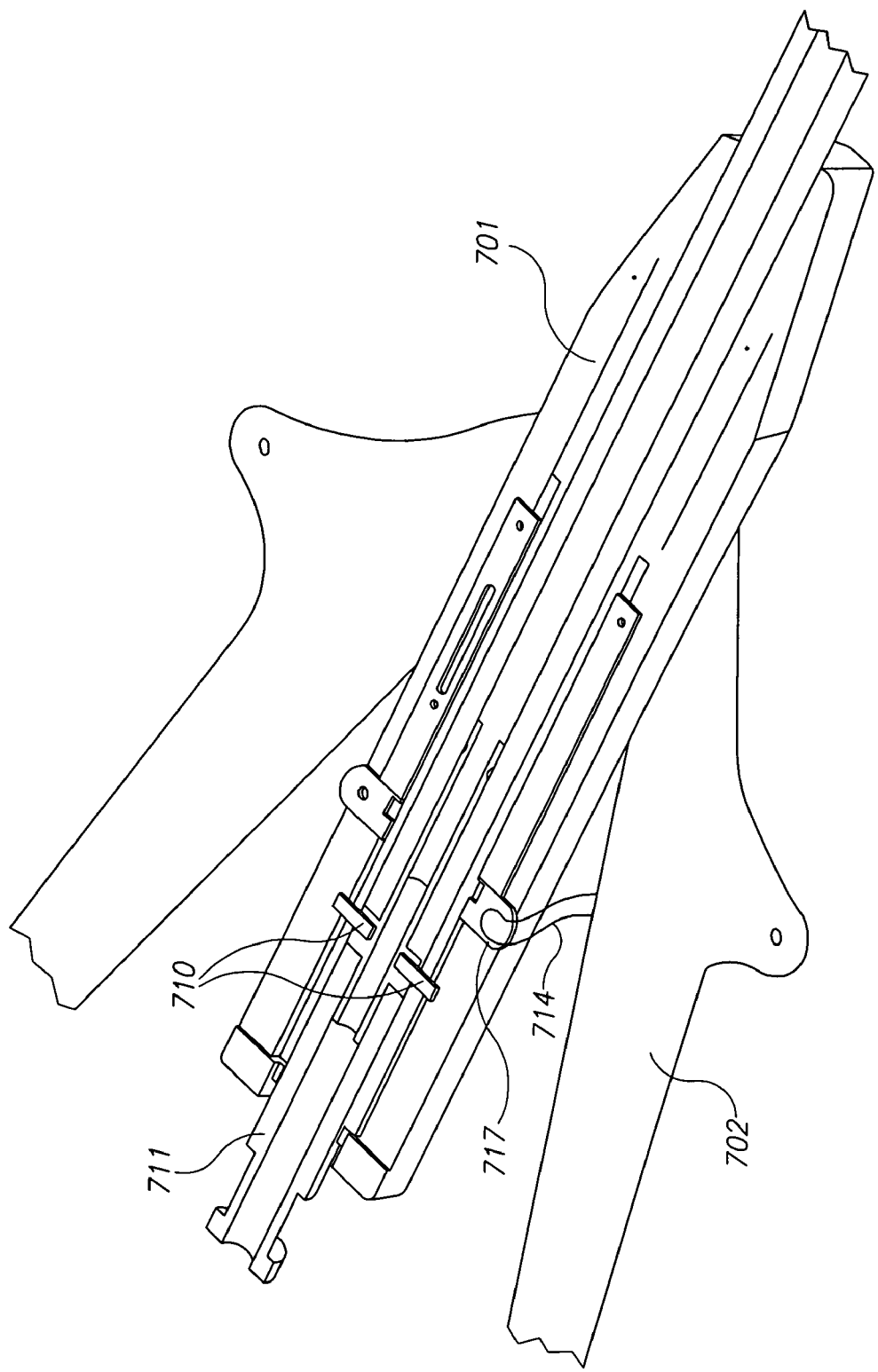
Figure 30A:
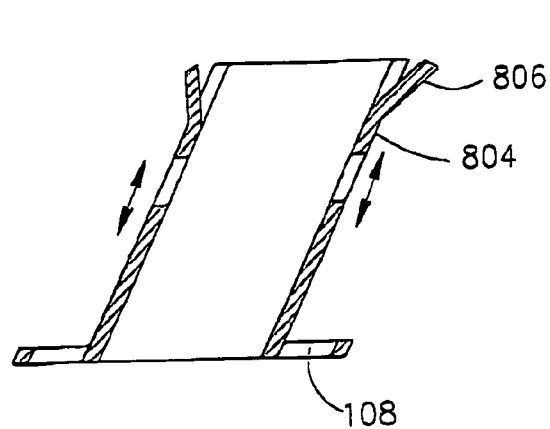
FIGS. 30A–30D, which correspond to FIGS. 1A–1D illustrate an anastomosis connector adapted for oblique connections, in accordance with a preferred embodiment of the invention.
Figure 30B:
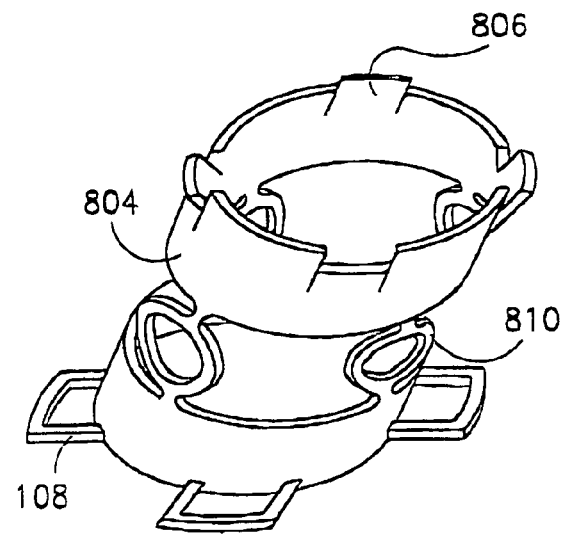
Figure 30C:
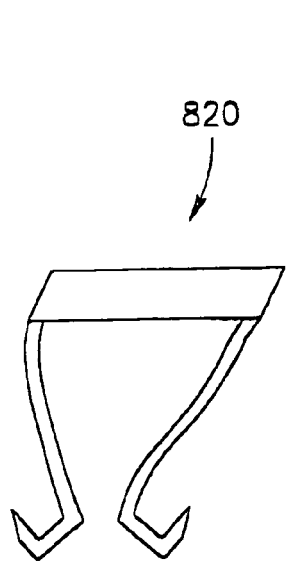
Figure 30D:
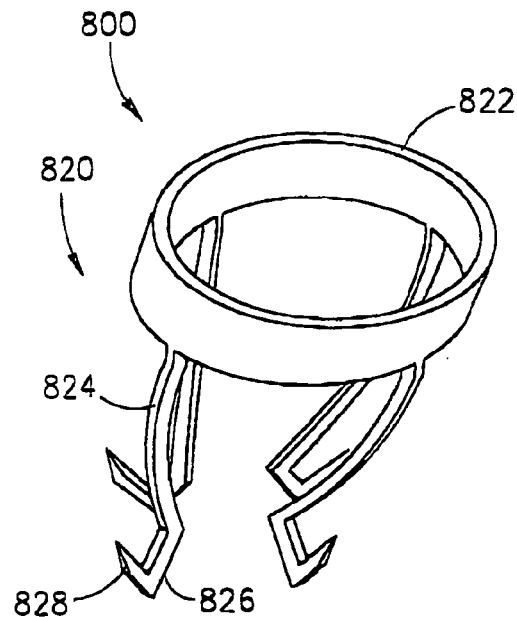

FIG. 29F is a cut-through view of the handle area of system 100, showing a mechanism for retracting portions of the system by squeezing a pair of handles 702. The squeezing is transmitted by a lever 714 to a pair of sliders 717. When sliders 717 are retracted enough, they retract holder 706 and magazine 705, via a pair of coupling pins 710. This retraction causes the forward spikes of device 709 to engage the target blood vessel. once the target blood vessel is engaged, only magazine 705 continues its retraction. As magazine 705 retracts, device 709 is freed and engages the target vessel using its backward spikes As the squeezing of handles 702 continues, rod 707 is retracted and causes holder 706 to be split, thereby splitting the outer layers and allowing the graft to be removed.

Oblique Anastomosis Connector

FIGS. 30A–30D, which correspond to FIGS. 1A–1D illustrate an anastomosis connector 800 adapted for oblique connections, in accordance with a preferred embodiment of the invention. the element numbers correspond to those of FIGS. 1A–1D, except that they are all "800" numbers rather than "100" numbers. Using an oblique connector allows connections geometries which can be more useful than a perpendicular geometry, for example to accommodate the angle of arrival of a graft, to accommodate nearby structures and/or for better blood flow. The connection may be oblique with respect to the axis of the target vessel or its transaxial direction. Exemplary oblique angles include, between 10° and 80°, more preferably between 30° and 70° and in an exemplary embodiment, about 45°.

Figure 31B:
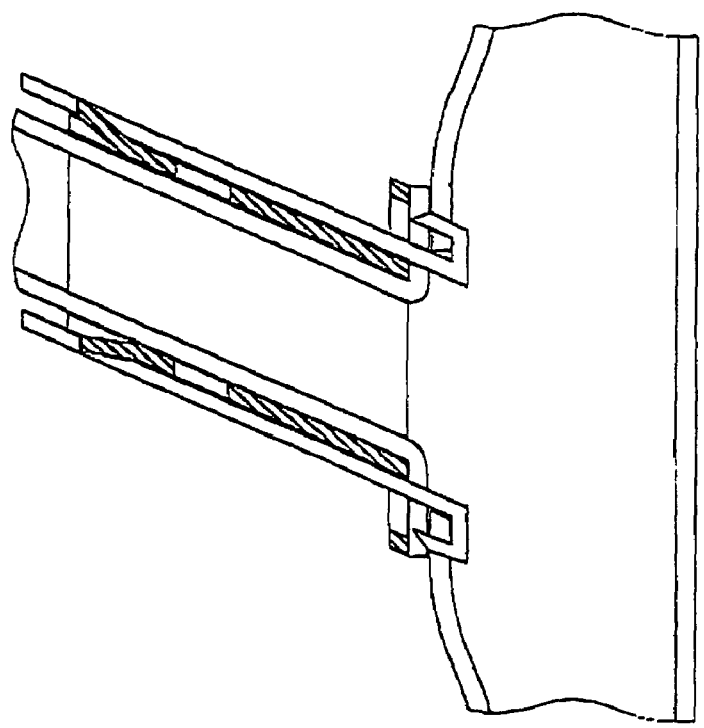
FIG. 31B, which corresponds to FIG. 2D, shows a completed oblique anastomosis, in accordance with a preferred embodiment of the invention.
Figure 31A:
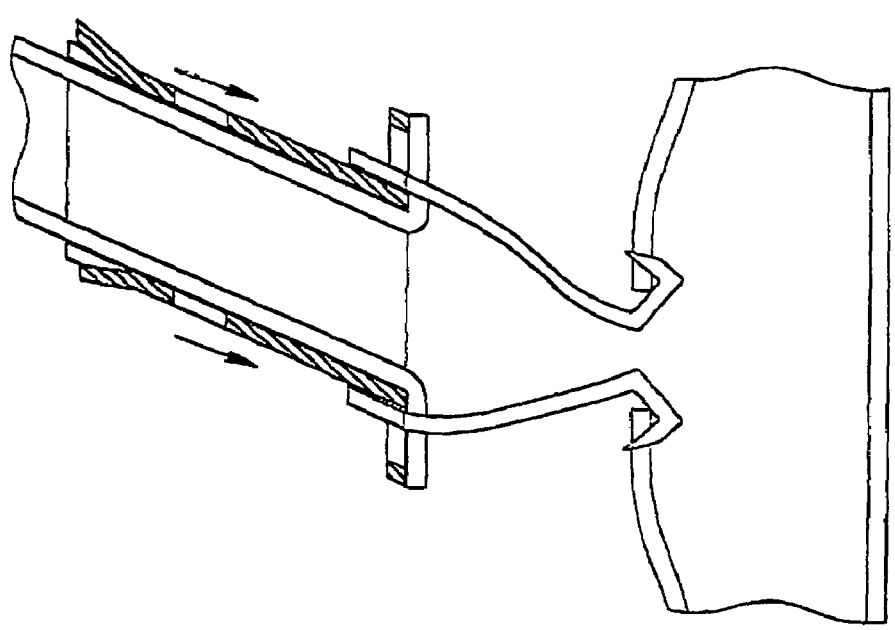
FIG. 31A, which corresponds to FIG. 2F shows the connector of FIGS. 30A–30D, during deployment, in accordance with a preferred embodiment of the invention.

FIG. 31A, which corresponds to FIG. 2F shows connector 800 during deployment. FIG. 30311B, which corresponds to FIG. 2D, shows a completed oblique anastomosis.

Figure 32A:
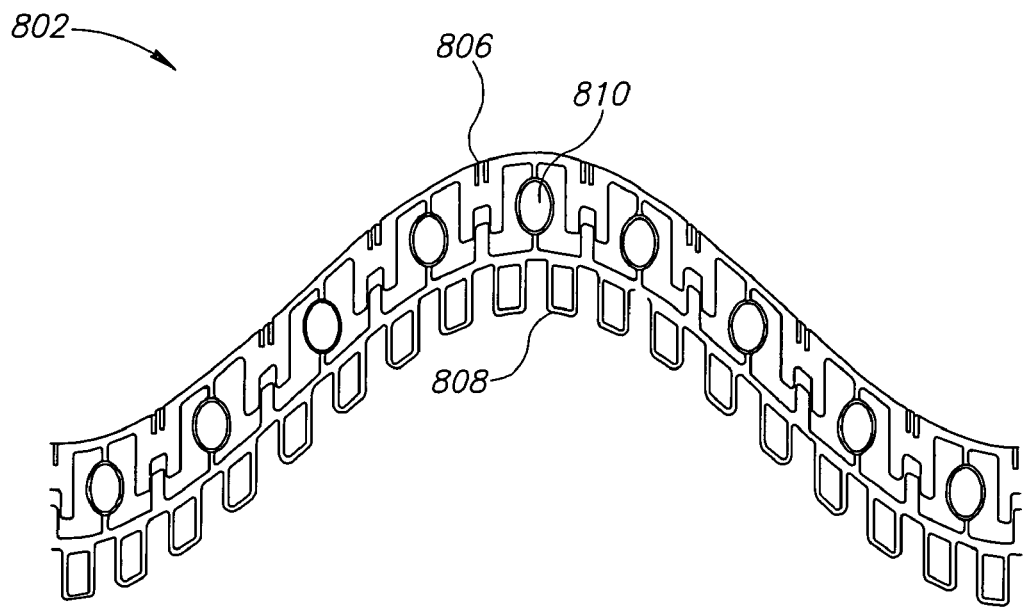
FIGS. 32A and 32B, which correspond to FIGS. 3A and 3B show a layout view of the connector of FIGS. 30A–30D.
Figure 32B:
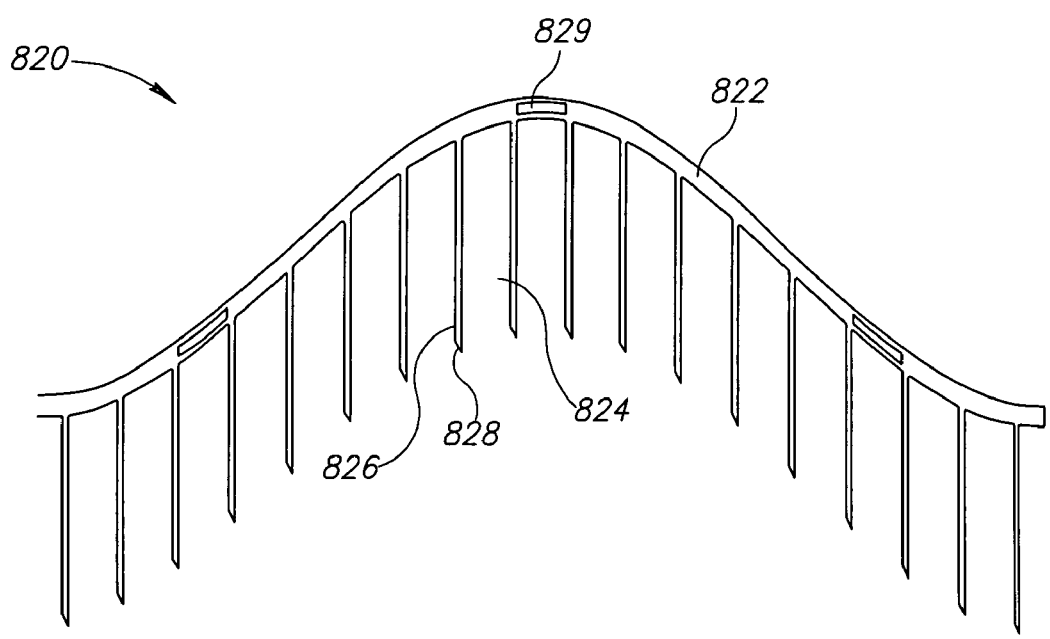

FIGS. 32A and 32B, which correspond to FIGS. 3A and 3B show a layout view of connector 800 of FIGS. 30A–30D. In both FIG. 32 and FIG. 3, the actual device may be shorter than the device shown, for example having only five spikes.

Although a generally tubular connector is shown, oval geometries or other geometries are provided in other preferred embodiments of the invention.

Everting an oblique graft is generally more difficult than everting a regular graft. Generally, one side of the graft, at the wider angle of the connector, is more easily everted, while the graft portion at the narrow angle, is less easily everted.

Figure 33A:
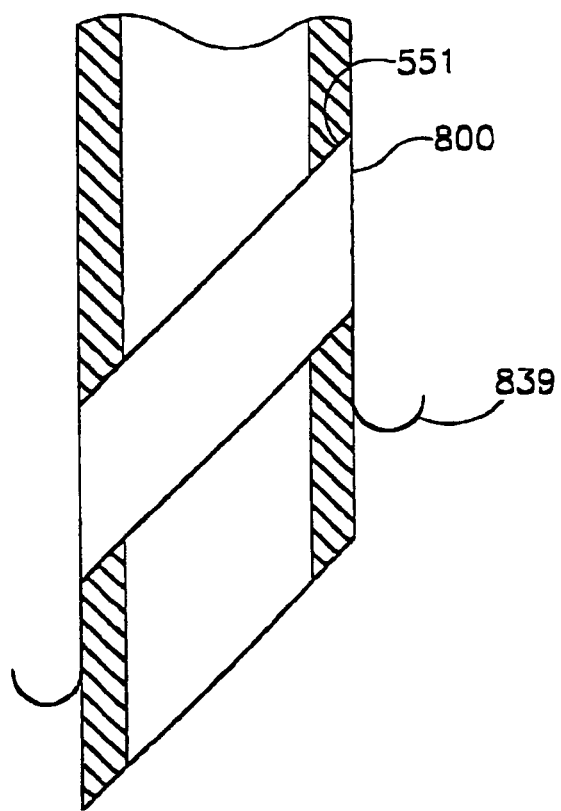
FIGS. 33A and 33B illustrate a method of mounting an oblique connector on a graft, in accordance with a preferred embodiment of the invention.
Figure 33B:
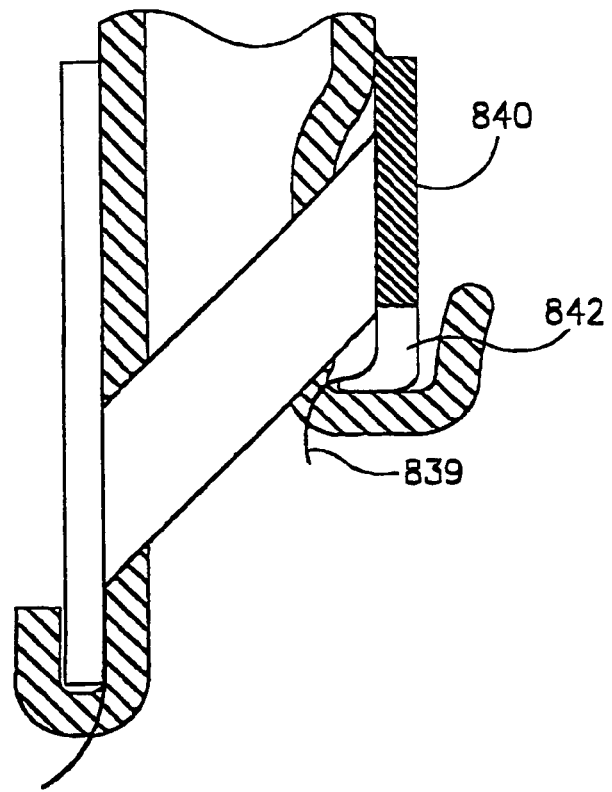

FIGS. 33A and 33B illustrate a variation in the eversion devices to assist in this difficulty. A device 800 on a graft 551 has a tip 839 at the narrow angle side of the graft. As shown in FIG. 33B, a holder 840 which is provided to hold connector 800, preferably also bends tip 839 inward using a protrusion 842, so that it can more easily transfix graft 551, using any of the techniques described above. Preferably, protrusion 842 is bend out of shape, for example by connector 800 when holder 840 is retracted.

Self Everting Connector

Figure 34A:
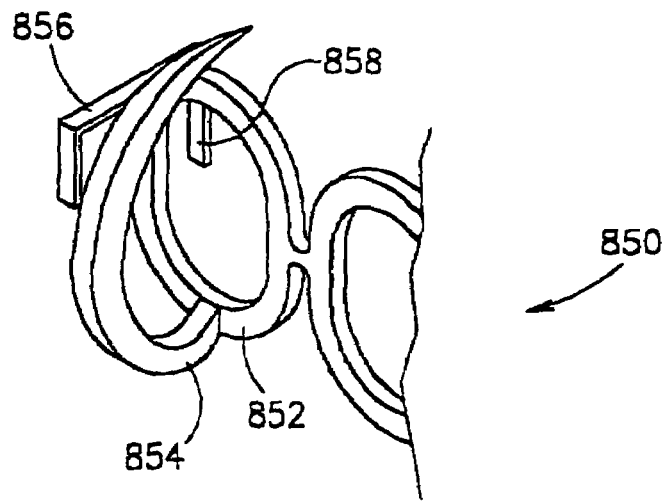
FIGS. 34A–34F illustrate a self-everting connector and a method of deploying such a connector, in accordance with a preferred embodiment of the invention.

FIGS. 34A–34F illustrate a self-everting connector 850 and a method of deploying such a connector, in accordance with a preferred embodiment of the invention. FIG. 34A shows one segment of connector 850, including a body section 858, a back spike 854, a forward spike 856 and a manipulation tab 858.

Figure 34B:
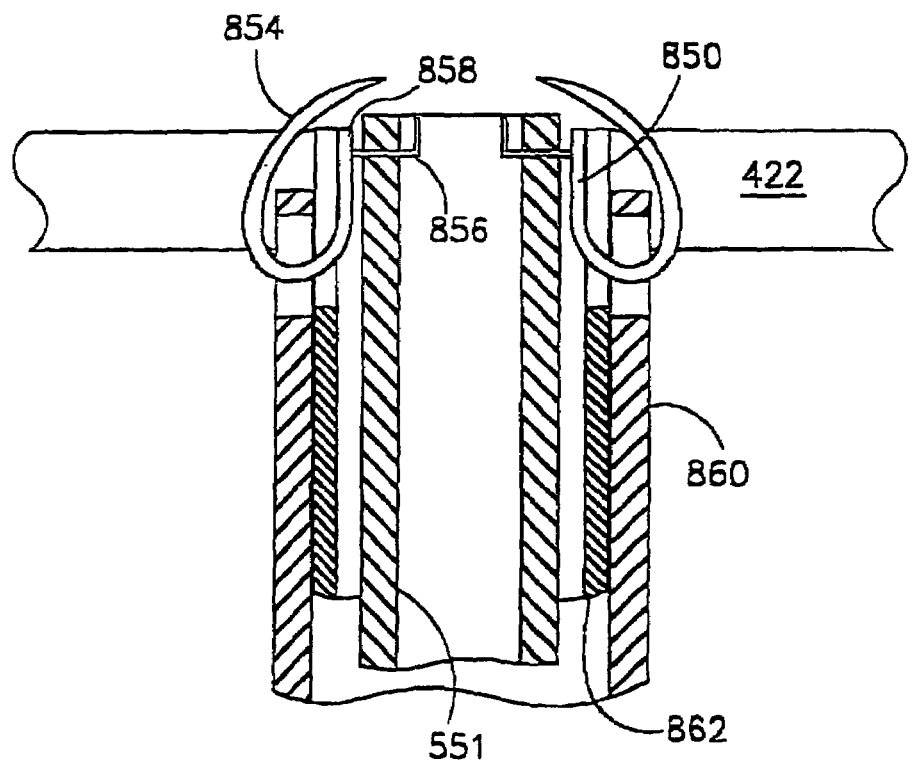

As shown in FIG. 34B, connector 850 is inserted into a vessel 422 and is mounted on a graft 551, such that forward spikes 856 are rotated into the graft lumen. This unnatural (in a super-elastic, elastic or shape-memory connector) position is preferably maintained by a tab holder 862 that presses against tabs 858. Alternatively, plastic deformation methods are used. Spikes 854 are preferably curved in to assist insertion into vessel 422, however this is not required. An over tube 860 is preferably provided outside of holder 862.

Figure 34C:
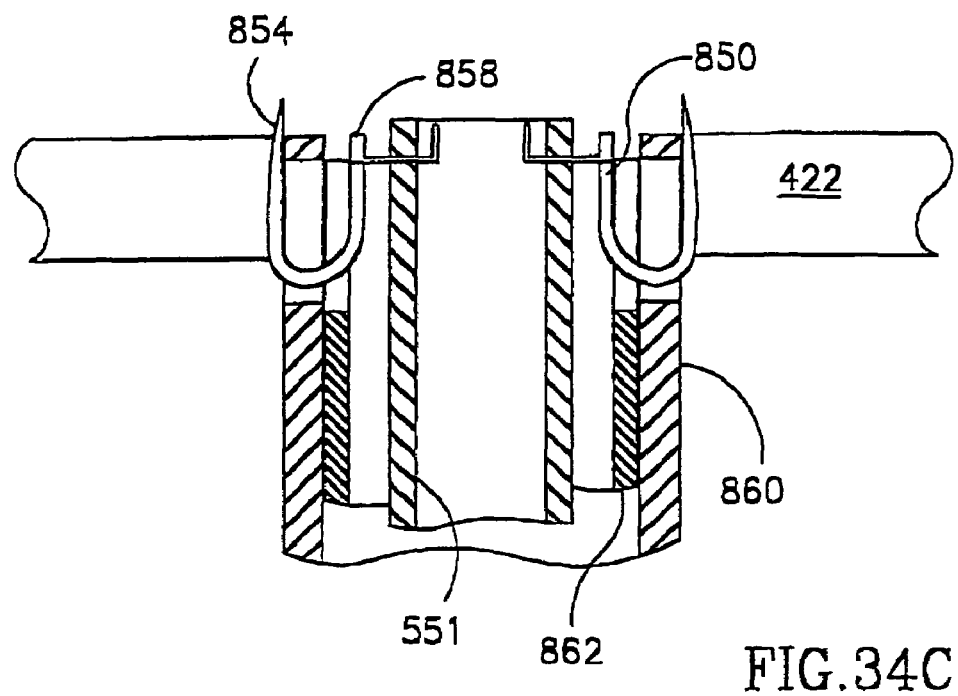

In FIG. 34C, over tube 860 is preferably advanced, to push vessel 422 away from the device and allow space for the eversion. The eversion may also be performed deeper into vessel 422 if space allows.

Figure 34D:
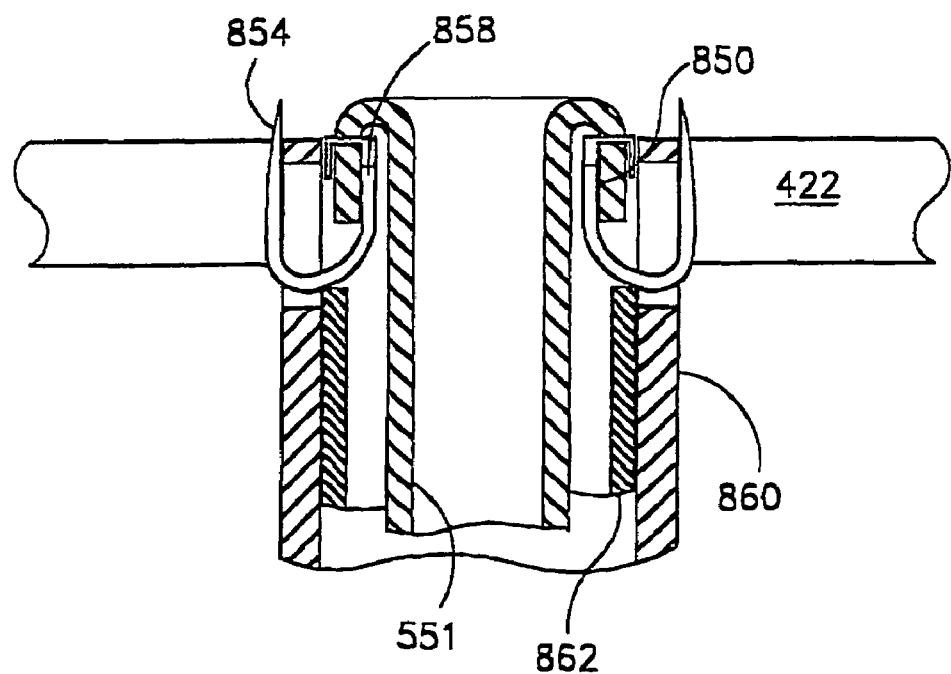

In FIG. 34D, holder 862 is retracted, releasing tabs 858 and allowing spikes 856 to twist back to their relaxed position, thereby everting graft 551.

Figure 34E:
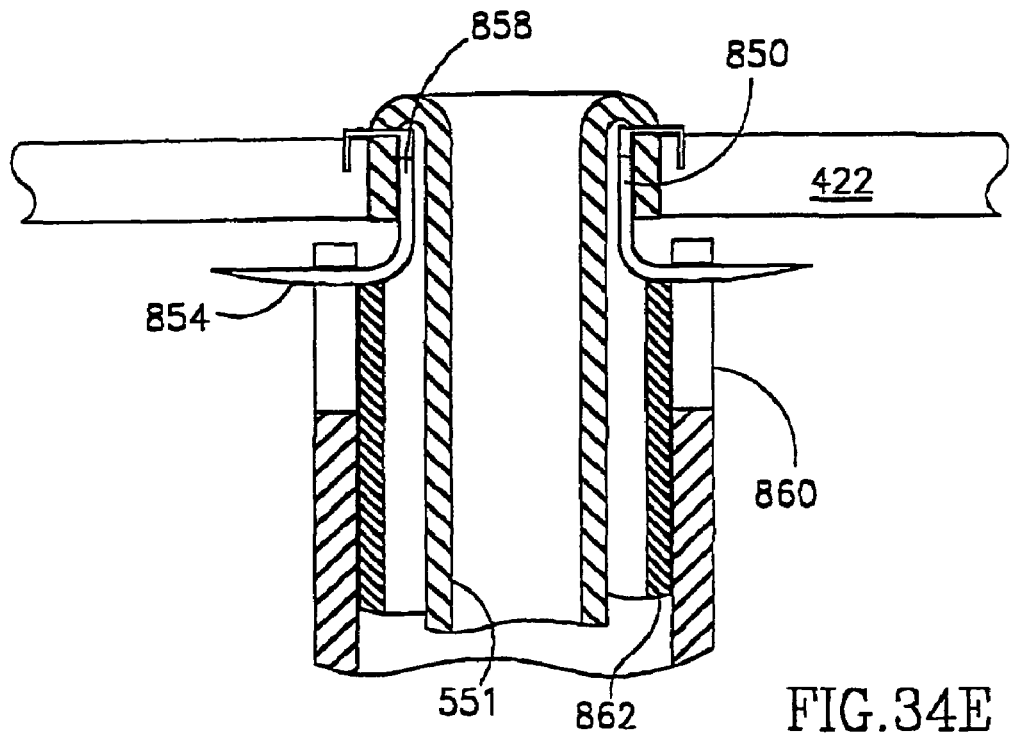

In FIG. 34E, over tube 860 is retracted, allowing vessel 422 to contact connector 850. Retraction of device 850 transfixes vessel 422 using spikes 856. Then, over tube 860 is retracted further, freeing spikes 864 to engage vessel 422 from the other side. As shown in the Fig., retraction of over tube 860 may be impeded by spikes 854. In one embodiment, a small amount of space is provided between over tube 860 and holder 862 to allow for spike 854. Alternatively, axial slots may be defined in over tube 860, allowing spikes 854 to be released by axially rotating over tube 860 relative to connector 850.

Figure 34F:
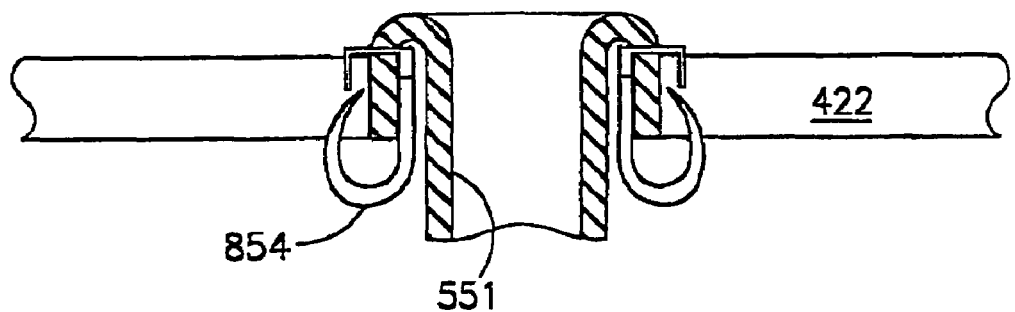

FIG. 34F shows a completed anastomosis.

Peripheral Kit

The description of the above procedures and devices have been directed especially towards coronary bypass procedures. However, by pass procedures may be performed in other parts of the body, such as the head, the brain, the abdomen or the extremities, for example, to perform an aorto-femoral bypass or other bypasses of vessels that provide blood to the lower limbs. The above described anastomotic connectors can be modified for the other locations. Preferably approximately one spike per mm perimeter is provided. Thus, a femoral device may have seven spikes.

Figure 35:
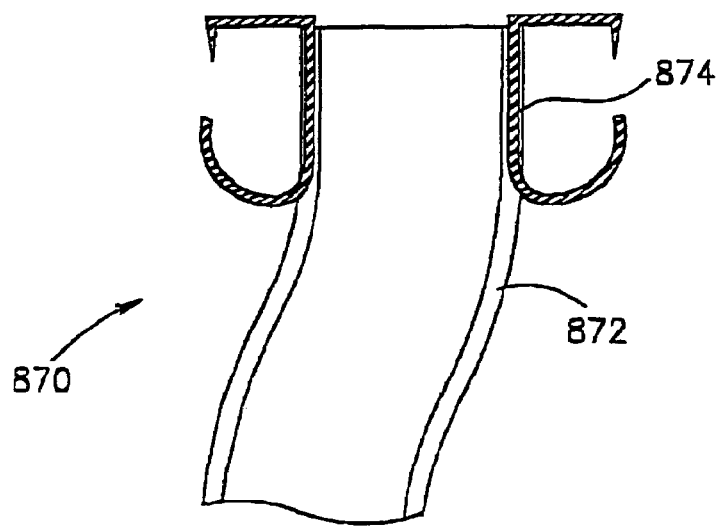
FIG. 35 illustrates a graft having an anastomosis connector embedded therein, in accordance with a preferred embodiment of the invention.

In many applications, a kit is provided, including a graft. Preferably, the connectors are pre-mounted on the graft, at one or both ends (possibly more if the graft has additional openings or splits). FIG. 35 shows a preferred method of mounting a connector 874 on a graft 872, to provide a ready to use graft-combination 870. Preferably, the connector is embedded in the wall of the graft, for example during its manufacture or by inserting the device after the graft is completed. Preferably, at least part of the graft overlaying the connector is adapted to bond well to a blood vessel to which it will be attached. The very end of the graft may optionally be manufactured to not cause coagulation if it is in contact with blood. The more distal portions may be manufactured to enhance coagulation. Although an end-connector is shown, a similar embedding may be performed for a side-type connector.

U.S. Pat. Nos. 5,641,373, 5,843,173, 5,415,619, 4,883,453, 4,552,707, 4,096,227, 5,861,033, 5,628,786, 4,957,669, 4,909,979 and 3,945,052, the disclosures of which are incorporated herein by reference, describe grafts and methods of manufacturing them that may be used in some preferred embodiments of the invention.

In an exemplary embodiment, a kit for performing a bypass procedure includes a graft and a guide wire or other guide for guiding the graft between the anastomosis locations.

Figure 36:
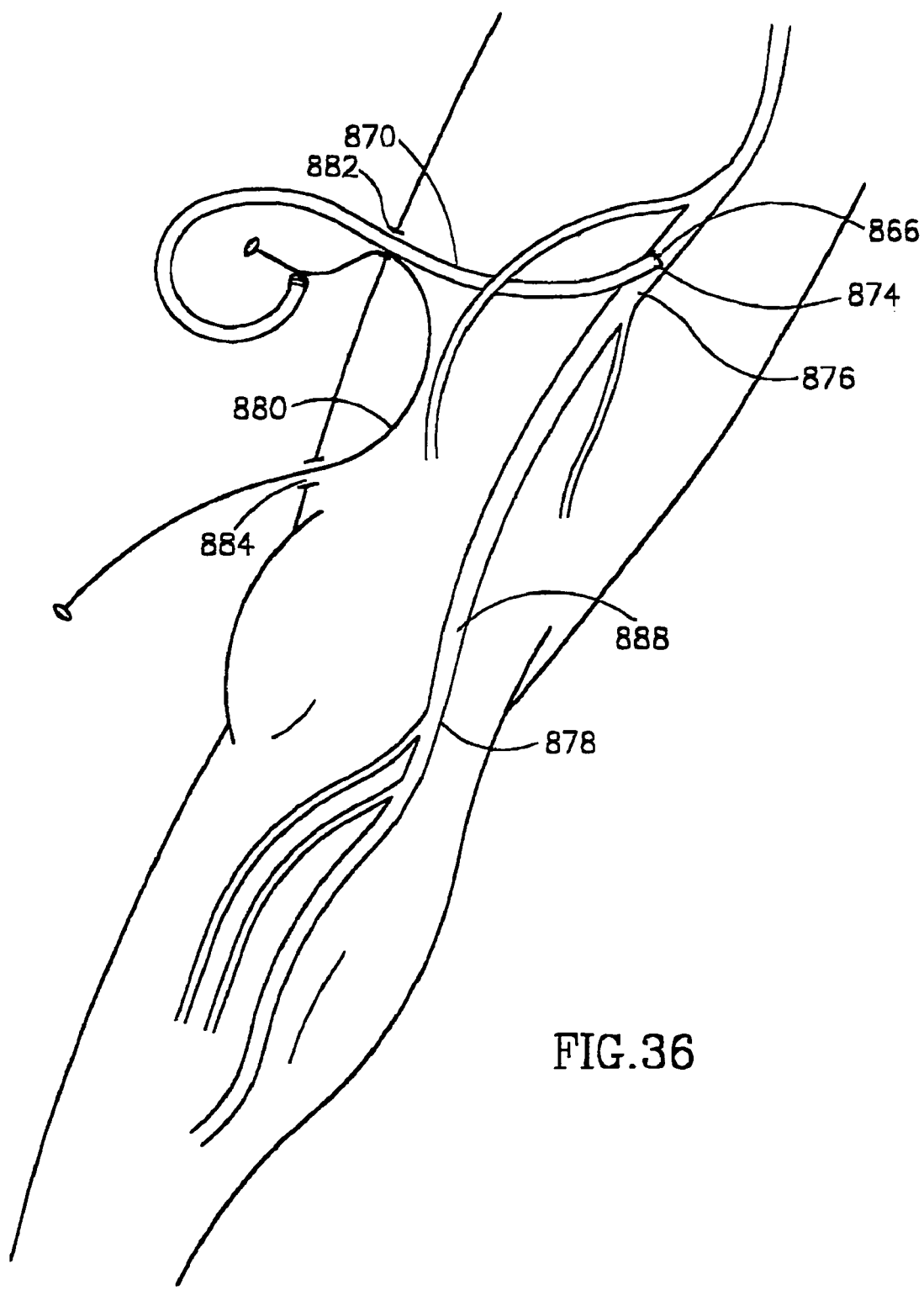
FIG. 36 illustrates a femoral-popliteal bypass procedure, in accordance with a preferred embodiment of the invention.

FIG. 36 illustrates an exemplary femoral-popliteal bypass procedure, in accordance with a preferred embodiment of the invention. A bypass using graft 870 is to be performed between a point 886 on a superficial femoral artery 876 and a point 888 on a popliteal artery 878. Preferably, keyhole openings 882 and 884 are made over points 886 and 888. Device 874 on one end of graft 870 is attached at point 886, for example as described above. Then a guide wire 880 is used to pull graft 870 through the body to the area of keyhole 884. In a preferred embodiment of the invention, guide wire 880 is rigid or includes a rigid guide member to more easily navigate between the two keyholes. Guide wire 880 is preferably attached to graft 880 using a suture. In an alternative embodiment, the anastomosis and navigation between the two points is performed endoscopicly, or transvascularly (at least providing the graft).

It should be appreciated that the above method sand device scan be adapted for use in many kinds of surgery, for example endoscopic, transvascular keyhole and open surgery. In particular it is noted that the manipulation of blood vessels and grafts may be performed completely inside the body, for example everting a LIMA through a keyhole.

It will be appreciated that the above described methods of vascular surgery may be varied in many ways, including, changing the order of steps, which steps are performed inside the body and which outside, the order of making the anastomosis connections, the order of steps inside each anastomosis, the exact materials used for the anastomotic connectors and/or which vessel is a "side" side and which vessel (or graft) is an "end" side of an end-to-side anastomosis. Further, in the mechanical embodiments, the location of various elements may be switched, without exceeding the sprit of the disclosure, for example, switching the anvil for the cutting edge in the hole-punching devices and switching the moving elements for non-moving elements where relative motion is required. In addition, a multiplicity of various features, both of method and of devices have been described. It should be appreciated that different features may be combined in different ways. In particular, not all the features shown above in a particular embodiment are necessary in every similar preferred embodiment of the invention. Further, combinations of the above features are also considered to be within the scope of some preferred embodiments of the invention. In addition, some of the features of the invention described herein may be adapted for use with prior art devices, in accordance with other preferred embodiments of the invention. The particular geometric forms used to illustrate the invention should not be considered limiting the invention in its broadest aspect to only those forms, for example, where a circular lumen is shown, in other embodiments an oval lumen may be used.

Also within the scope of the invention are surgical kits which include sets of medical devices suitable for making a single or a small number of anastomosis connections. Section headers are provided only to assist in navigating the application and should not be construed as necessarily limiting the contents described in a certain section, to that section. Measurements are provided to serve only as exemplary measurements for particular cases, the exact measurements applied will vary depending on the application. When used in the following claims, the terms "comprises", "comprising", "includes", "including" or the like means "including but not limited to".

It will be appreciated by a person skilled in the art that the present invention is not limited by what has thus far been described. Rather, the scope of the present invention is limited only by the following claims.

What is claimed is:

1. An anastomotic connector for connecting a graft to a target vessel, comprising:
    a radially-thin collar section, adapted to surround a portion of the graft; and
    a separate spike section, adapted to mount on said collar section and comprising a plurality of spikes, each of said spikes adapted to first transfix said graft and then penetrate said target vessel,
    wherein the separate spike section comprises a ring to which the plurality of spikes are attached and wherein the graft is not caught between the ring and the collar section.

2. A connector according to claim 1, comprising at least one locking element for interlocking said spike section and said collar section.

3. A connector according to claim 2, wherein said locking element is formed on said collar portion.

4. A connector according to claim 3, wherein said locking element mates with an aperture defined by said spike section.

5. A connector according to claim 2, wherein said locking element provides a spring-action, which action relative axial motion between at least part of said spike section and at least part of said collar section, with a force dependent on the range of motion.

6. A connector according to claim 1, wherein said spike section comprises a super-elastic material.

7. A connector according to claim 1, wherein said spikes are pre-bent in a hook shape, such that said hook shape is adapted to engage the target vessel.

8. A connector according to claim 1, wherein said collar element connects to a plurality of flange elements proximal to said target vessel.

9. A connector according to claim 8, wherein said flange elements define apertures for said spikes to pass through.

10. A connector according to claim 9, wherein said flange elements include at least one opening in their perimeter, wide enough for one of said spikes to be brought in through.

11. A connector according to claim 1, wherein said collar section defines a cylindrical volume.

12. A connector according to claim 1, wherein said collar section is adapted to form a perpendicular anastomosis.

13. A connector according to claim 1, wherein said collar section is adapted to form an oblique anastomosis.

14. A connector according to claim 1, wherein the thin collar section does not fasten the graft on its own.

15. A connector according to claim 1, wherein the thin collar section engages the graft.

16. An anastomotic connector for connecting a graft to a target vessel, comprising:
    a base for surrounding said graft;
    a plurality of spikes for transfixing said graft and engaging said target vessel; and
    at least one spring element attached to at least one of said spikes, which spring element couples a connection between said spike and said base and allows resilient motion of said spike along an axis of said base.

17. A connector according to claim 16, wherein said spikes and said base form a single element.

18. A connector according to claim 16, wherein said spikes and said base form two separate elements.

19. A connector according to claim 16, wherein said spring comprises a flat coil spring.

20. A connector according to claim 16, wherein said spring comprises a leaf spring.

21. A connector according to claim 16, wherein said at least one spring comprises at least two springs in series.

22. A connector according to claim 16, wherein said connector is configured for performing an oblique anastomosis.

23. A connector according to claim 16, comprising at least one tab associated with one spike of said spikes, for moving said spike.

24. A connector according to claim 23, wherein said tab is adapted for retracting said spike.

25. A connector according to claim 23, wherein said tab is adapted for advancing said spike.

26. A connector according to claim 16, wherein, each of said spikes has at least one independent associated spring.

27. An anastomosis connector, comprising:
a ring shaped base having an axis;
at least one plurality of spikes on one side of said ring wherein said spikes are adapted to not penetrate a graft on which said connector is mounted prior to being attached to a target vessel; and
at least one transaxial thickening in at least one of said spikes, distanced from said ring.

28. A connector according to claim 27, comprising a second plurality of spikes pointing in an opposite direction from said first set of spikes.

29. A connector according to claim 27, wherein said thickening comprises a point where said spike splits into tines.

30. A connector according to claim 29, wherein said tines are shorter than a thickness of a target blood vessel for which the connector is designed.

31. A connector according to claim 27, wherein said at least one plurality of spikes do not apply radial pressure towards or away from said ring, once deployed.

32. A method of containing and releasing an anastomotic connector having a thickening, comprising:
containing said connector between two tubes, said thickening being constrained from axial motion by at least one protrusion defined on at least one of said tubes; and
removing an outer one of said tubes, such that the connector deforms and the thickening is not constrained by said at least one protrusion.

33. A method of performing an anastomosis between a graft and a target vessel, comprising:
inserting an anastomosis connector into the target vessel;
releasing at least one forward spike of said connector;
retracting said connector such that said forward spike engages said target vessel; and
completing said anastomosis.

34. A method according to claim 33, wherein completing said anastomosis comprises releasing at least one backward spike of said connector to engage said target vessel.

35. A method according to claim 33, wherein completing said anastomosis comprises locking said spike to a part of said connector other than said spike.

36. A method according to claim 33, wherein completing said anastomosis comprises releasing said spike to retract towards a part of said connector other than said spike.

37. A method of heat-treating an anastomosis connector, comprising:
fitting a cut connector into a mold;
fixing said mold to bend both forward and backwards spikes of said connector into a desired configuration; and
heat-treating said fixed connector, thereby training it to said configuration.

38. A method of connecting a graft to a target vessel, comprising:
surrounding a portion of the graft with a thin collar section;
mounting a separate spike section on the collar section, such that the spikes of the spike section transfix the graft and penetrate the target vessel; and
retracting the spike section relative to the graft, so as to connect the vessel to the graft.

39. A method according to claim 38, wherein retracting the spike section comprises moving relative to the collar section.

40. An anastomotic connector for connecting a graft to a target vessel, comprising:
a plurality of spikes adapted to transfix a graft and penetrate a blood vessel;
a plurality of aperture elements defining apertures adapted to receive the spikes; and
at least one lock element which locks against at least one of the spikes, so as to limit movement of the spike relative to at least one of the aperture elements, while the spike transfixes the graft and penetrates the blood vessel
wherein the at least one lock element comprises an elastic material.

41. A connector according to claim 40, wherein the at least one lock element comprises a lock element corresponding to each aperture.

42. A connector according to claim 40, wherein the at least one lock element is mounted on a collar section connecting the aperture elements.

43. A connector according to claim 42, wherein the collar section has an open structure which substantially reduces the amount of material of the connector.

44. A connector according to claim 40, wherein at least one of the lock elements is mounted on an aperture element.

45. A connector according to claim 40, wherein the locking of the at least one lock element allows some movement of the spikes relative to each other.

46. A connector according to claim 40, wherein the locking of the at least one lock element allows some motion of the spikes relative to the aperture elements.

47. A connector according to claim 46, wherein the motion of the spikes relative to the aperture elements can accommodate variations in tissue geometry of the target vessel.

48. A connector according to claim 40, wherein the spikes are axially elastic.

49. A connector according to claim 40, wherein the at least one lock element locks by mating with an aperture.

50. A connector according to claim 40, wherein once the lock element is locked it does not open by itself.

51. A connector according to claim 40, wherein the locking of the locking element is achieved by retraction of the spikes.

52. An anastomotic connector for connecting a graft to a target vessel, comprising:
a plurality of spikes adapted to transfix a graft and penetrate a blood vessel;
a plurality of aperture elements defining apertures adapted to receive the spikes; and
at least one lock element on at least one of the aperture elements, which, when locked, limits movement of at least one of the spikes relative to at least one of the aperture elements, while the spikes transfix the graft and penetrate the blood vessel,
wherein the lock elements lock against the spikes.

53. A connector according to claim 52, wherein the at least one lock element comprises a lock element corresponding to each aperture.

54. A connector according to claim 52, wherein the locking of the at least one lock element allows some motion of the spikes relative to the aperture elements.

55. A connector according to claim 54, wherein the locking of the at least one lock element allows some axial motion of the spikes relative to the aperture elements.

56. A connector according to claim 54, wherein the motion of the spikes relative to the aperture elements can accommodate variations in tissue geometry of the target vessel.

57. A connector according to claim 52, wherein the at least one lock element comprises an elastic material.

58. A connector according to claim 52, wherein the spikes are axially elastic.

59. A connector according to claim 52, wherein the at least one lock element locks by mating with an aperture associated with at least one of the spikes.

60. A connector according to claim 52, wherein once the lock element is locked it does not open by itself.

61. A connector according to claim 52, wherein the locking of the lock element is achieved by retraction of the spikes.

62. An anastomotic connector for connecting a graft to a target vessel, comprising:
a plurality of spikes adapted to transfix a graft and penetrate a blood vessel;
a plurality of aperture elements defining apertures adapted to receive the spikes; and
a plurality of lock elements, each lock element corresponding to an aperture element in a 1:1 correspondence, which, when locked, limit movement of at least one of the spikes relative to the corresponding aperture element, while the spikes transfix the graft and penetrate the blood vessel,
wherein the locking of the lock element is achieved by retraction of the spikes.

63. A connector according to claim 62, wherein the lock elements lock against the spikes.

64. A connector according to claim 62, wherein the locking of the plurality of lock elements allows some motion of the spikes relative to the aperture elements.

65. A connector according to claim 64, wherein the locking of the plurality of lock elements allows some axial motion of the spikes relative to the aperture elements.

66. A connector according to claim 64, wherein the motion of the spikes relative to the aperture elements can accommodate variations in tissue geometry of the target vessel.

67. A connector according to claim 62, wherein the spikes are axially elastic.

68. A connector according to claim 62, wherein once the lock element is locked it does not open by itself.

69. A method of connecting a graft to a target vessel, comprising:
inserting a plurality of spikes through a plurality of apertures defined by aperture elements;
transfixing a graft by the plurality of spikes;
penetrating a blood vessel by the spikes; and
locking at least one lock element against one of the spikes, so as to limit movement of the at least one spike relative to at least one of the aperture elements.

70. A method according to claim 69, wherein the locking of the at least one lock element is achieved by retracting the at least one of the spikes.

71. A method according to claim 69, wherein the locking of the at least one lock element allows some movement of the relative to each other.

72. A method according to claim 69, wherein the at least one lock element is mounted on a collar section connecting the aperture elements.

73. A method according to claim 72, wherein the collar section has an open structure which substantially reduces the amount of material of the connector.

74. A method according to claim 69, wherein the spikes penetrate the blood vessel, after the spikes are inserted into the apertures.

75. A method of connecting a graft to a target vessel, comprising:
inserting a plurality of spikes through a plurality of apertures defined by aperture elements;
transfixing a graft by the plurality of spikes;
penetrating a blood vessel by the spikes; and
locking at least one lock element which is situated on at least one of the aperture elements, so as to limit movement of at least one of the spikes relative to at least one of the aperture elements.

76. A method according to claim 75, wherein the locking of the at least one lock element is achieved by retracting the at least one of the spikes.

77. A method according to claim 75, wherein the locking of the at least one lock element allows some movement of the spikes relative to each other.

78. A method according to claim 75, wherein the locking of the at least one lock element allows some motion of the spikes relative to the aperture elements.

79. A method according to claim 75, wherein the at least one lock elements is elongate.

80. A connector according to claim 75, wherein the at least one lock element locks by mating with an aperture associated with at least one of the spikes.

81. A method according to claim 75, wherein the spikes penetrate the blood vessel, after the spikes are inserted into the apertures.

82. A method of connecting a graft to a target vessel, comprising:
inserting a plurality of spikes through a plurality of apertures defined by aperture elements;
transfixing a graft by the plurality of spikes;
penetrating a blood vessel by the spikes; and
locking at least one lock element by retracting at least one of the spikes so as to limit movement of at least one of the spikes relative to at least one of the aperture elements.

83. A method according to claim 82, wherein the locking of the at least one lock element allows some movement of the spikes relative to each other.

84. A method according to claim 82, wherein the spikes penetrate the blood vessel, after the spikes are inserted into the apertures.

85. A method of connecting a graft to a target vessel, comprising:
- inserting a plurality of spikes through a plurality of apertures defined by aperture elements;
- transfixing a graft by the plurality of spikes;
- penetrating a blood vessel by the spikes, after the spikes are inserted into the aperture; and
- locking at least one lock element, so as to limit movement of at least one of the spikes relative to at least one of the aperture elements.

86. A method according to claim 85, wherein the locking of the at least one lock element allows some movement of the spikes relative to each other.

87. An anastomotic connector for connecting a graft to a target vessel, comprising:
- a plurality of spikes adapted to transfix a graft and penetrate a blood vessel;
- a plurality of aperture elements defining apertures adapted to receive the spikes, while they transfix the graft and penetrate the blood vessel; and
- at least one movement restricting element which is adapted to be moved into a fixation state after the spikes transfix the graft and penetrate the blood vessel,
- wherein, in the fixation state, the movement of at least one of the spikes is limited relative to at least one of the aperture elements, while some movement of the spikes relative to each other is allowed in the fixation state.

88. A connector according to claim 87, wherein the movement restricting element comprises a lock element.

89. A connector according to claim 87, wherein the connector has an open structure.

90. A connector according to claim 87, wherein in the fixation state, the movement restricting element allows some motion of the spikes relative to the aperture elements.

91. A connector according to claim 87, wherein in the fixation state, the movement restricting element allows some axial motion of the spikes relative to the aperture elements.

92. An anastomotic connector for connecting a graft to a target vessel, comprising:
- a plurality of spikes adapted to first transfix a graft and then penetrate a blood vessel; and
- a plurality of aperture elements defining apertures adapted to receive the spikes, while they transfix the graft and penetrate the blood vessel,
- wherein the connector has an open structure, which substantially reduces the amount of material of the connector, between the aperture elements.

93. A connector according to claim 92, wherein the connector has a mesh construction between the aperture elements.

94. A connector according to claim 92, wherein the aperture elements are included in a two-dimensional annular ring shape which has free space between each two adjacent aperture elements.

95. A connector according to claim 92, wherein the plurality of aperture elements include radial openings.

96. A connector according to claim 95, wherein the radial openings comprise side openings.

97. A connector according to claim 92, wherein the spikes have tips adapted to lock against the aperture elements.

98. A method of connecting a graft to a target vessel, comprising:
- providing a plurality of apertures defined by aperture elements in an annular ring shaped two-dimensional space around a graft, which has free space between each two adjacent aperture elements;
- inserting a plurality of spikes through the apertures;
- transfixing the graft by the plurality of spikes; and
- penetrating a blood vessel by the spikes.

99. A method according to claim 98, comprising locking at least one lock element which, when locked, limits movement of the plurality of spikes relative to at least one of the aperture elements.

100. An anastomotic connector for connecting a graft to a target vessel, comprising:
- a plurality of spikes adapted to transfix a graft and penetrate a blood vessel;
- a plurality of aperture elements defining apertures adapted to receive the spikes; and
- a plurality of lock elements, each lock element corresponding to an aperture element, which, when locked, limit movement of at least one of the spikes relative to the corresponding aperture element, while the spikes transfix the graft and penetrates the blood vessel,
- wherein the lock elements lock against the spikes.

101. An anastomotic connector for connecting a graft to a target vessel, comprising:
- a plurality of axially elastic spikes adapted to transfix a graft and penetrate a blood vessel;
- a plurality of aperture elements defining apertures adapted to receive the spikes; and
- a plurality of lock elements, each lock element corresponding to an aperture element, which, when locked, limit movement of at least one of the spikes relative to the corresponding aperture element, while the spikes transfix the graft penetrate the blood vessel.

102. An anastomotic connector for connecting a graft to a target vessel comprising:
- a radially-thin collar section, adapted to surround a portion of the graft; and
- a separate spike section, adapted to mount on said collar section and comprising a plurality of spikes, each of said spikes adapted to transfix said graft and penetrate said target vessel,
- wherein said spikes are pre-bent in a hook shape, such that said hook shape is adapted to engage the target vessel.

103. An anastomotic connector for connecting a graft to a target vessel, comprising:
- a plurality of spikes adapted to transfix a graft and penetrate a blood vessel; and
- a plurality of aperture elements defining apertures adapted to receive the spikes while the spikes transfix the graft and penetrate the blood vessel,
- wherein the connector has an open structure, which substantially reduces the amount of material of the connector, between the aperture elements,
- and wherein the connector has a mesh construction between the aperture elements.

104. An anastomotic connector for connecting a graft to a target vessel, comprising:
- a plurality of spikes adapted to transfix a graft and penetrate a blood vessel; and
- a plurality of aperture elements defining apertures adapted to receive the spikes while the spikes transfix the graft and penetrate the blood vessel,
- wherein the connector has an open structure, which substantially reduces the amount of material of the connector, between the aperture elements,
- and wherein the aperture elements are included in a two-dimensional annular ring shape which has free space between each two adjacent aperture elements.

105. An anastomotic connector for connecting a graft to a target vessel, comprising:

a plurality of spikes adapted to transfix a graft and penetrate a blood vessel; and a plurality of aperture elements defining apertures adapted to receive the spikes while the spikes transfix the graft and penetrate the blood vessel, wherein the connector has an open structure, which substantially reduces the amount of material of the connector, between the aperture elements, and wherein the plurality of aperture elements include radial openings.

106. A connector according to claim 105, wherein the radial openings comprise side openings.

107. An anastomotic connector for connecting a graft to a target vessel, comprising:

a plurality of spikes adapted to transfix a graft and penetrate a blood vessel;

a plurality of aperture elements defining apertures adapted to receive the spikes; and at least one lock element which locks against at least one of the spikes, so as to limit movement of the spike relative to at least one of the aperture elements while the spike transfixes the graft and penetrates the blood vessel, wherein the locking of the locking element is achieved by retraction of the spikes.

* * * * *